US007501127B2

(12) United States Patent
Howley et al.

(10) Patent No.: US 7,501,127 B2
(45) Date of Patent: Mar. 10, 2009

(54) INTERGENIC REGIONS AS NOVEL SITES FOR INSERTION OF HIV DNA SEQUENCES IN THE GENOME OF MODIFIED VACCINIA VIRUS ANKARA

(75) Inventors: Paul Howley, Glen Waverly (AU); Sonja Leyrer, München (DE); Paul Chaplin, München (DE); Eva Felder, München (DE)

(73) Assignee: Bavarian Nordic A/S, Kvistgaard (DK)

( * ) Notice: Subject to any disclaimer, the term of this patent is extended or adjusted under 35 U.S.C. 154(b) by 353 days.

(21) Appl. No.: 11/355,948

(22) Filed: Feb. 17, 2006

(65) Prior Publication Data

US 2006/0188961 A1     Aug. 24, 2006

Related U.S. Application Data

(63) Continuation-in-part of application No. 10/514,761, filed as application No. PCT/EP03/05045 on May 14, 2003.

(30) Foreign Application Priority Data

| May 16, 2002 | (DK) | ............................. | 2002 00752 |
| May 16, 2002 | (DK) | ............................. | 2002 00753 |
| Feb. 24, 2005 | (EP) | ................................. | 05004012 |

(51) Int. Cl.
*A61K 39/12* (2006.01)
*A61K 39/21* (2006.01)
*A61K 39/275* (2006.01)

(52) U.S. Cl. ............... 424/199.1; 424/208.1; 424/232.1

(58) Field of Classification Search ........................ None
See application file for complete search history.

(56) References Cited

U.S. PATENT DOCUMENTS

| 5,185,146 A | 2/1993 | Altenburger |
| 6,596,279 B1 * | 7/2003 | Paoletti et al. ........... 424/199.1 |
| 6,682,742 B1 * | 1/2004 | Wintersperger et al. .. 424/199.1 |

FOREIGN PATENT DOCUMENTS

| EP | 0 753 581 | 1/1997 |
| EP | 1 146 125 | 10/2001 |
| EP | 1 288 304 | 3/2003 |
| EP | 03/05045 | 5/2003 |
| WO | WO 97/02355 | 1/1997 |
| WO | WO 01/68820 | 9/2001 |
| WO | WO 02/42480 | 5/2002 |
| WO | WO 03/053463 | 7/2003 |
| WO | WO 03/097675 | 11/2003 |
| WO | WO 03/097844 | 11/2003 |
| WO | WO 2004/015118 | 2/2004 |
| WO | WO 2004/048582 | 6/2004 |

OTHER PUBLICATIONS

Antoine, G., et al., 1998, The complete genomic sequence of the modified vaccinia Ankara strain: comparison with other orthopoxviruses, Virol. 244:365-396.*
Scheiflinger, F., et al., 1996, Evaluation of the thymidine kinase (tk) locus as an insertion site in the highly attenuated vaccinia MVA strain, Arch. Virol. 141:663-669.*
Spehner, D., et al., 1990, Construction of fowlpox virus vectors with intergenic insertions: expression of the beta-galactosidase gene and the measles virus fusion gene, J. Virol. 64(2):527-533.*
Meyer et al., Mapping of Delections in the Genome of the Highly Attenuated Vaccinia Virus MVA and Their Influence on Virulence, *J Gen Virol.*, vol. 72 (Pt 5), pp. 1031-1038, (1991).
Francis et al., "Advancing AIDSVAX™ to Phase 3. Safety, Immunogenicity, and Plans for Phase 3," *AIDS Res. Hum. Retroviruses*, vol. 14 (Suppl. 3) No. 5, pp. S325-31 (1998).
Scheiflinger et al., "Evaluation of the Thymidine Kinase (tk) Locus as an Insertion Site in the Highly Attenuated Vaccinia MVA Strain", *Arch Virol.*, vol. 141 No. 3-4, pp. 663-669, (1996).
Goebel et al., "The Complete DNA Sequence of Vaccinia Virus", *Viroloy*, vol. 179 No. 1, pp. 247-266 and 517-563 (1990).
Massung et al., "Analysis of the Complete Genome of Smallpox Variola major Virus Strain Bangladesh-1975", *Virology*, vol. 201 No. 2, pp. 215-240 (1994).
Needleman et al., "A General Method Applicable to the Search for Similarities in the Amino Acid Sequence of Two Proteins", *J. Mol. Biol.*, vol. 48 No. 3, pp. 443-453 (1970).
Davison et al., "Structure of Vaccinia Virus Late promoters", *J. Mol. Biol.*, vol. 210 No. 4, pp. 771-784, (1989).
Agostini et al., "Phosphorylation of Vpr Regulates HIV Type 1 Nuclear Import and Macrophage Infection", *AIDS Res Hum Retroviruses*, vol. 18 No. 4, pp. 283-288, (2002).
Vanitharani et al., "HIV-1 Vpr Transactivates LTR-directed Expression Through Sequences Present Within-278 to-176 and increases Virus Replication In Vitro", *Virology*, vol. 289 No. 2, pp. 334-342, (2001).
Luo et al., "Molecular Determinants of Nef Function", *J. Biomed Sci.*, vol. 4 No. 4, pp. 132-138 (1997).
Preusser et al., "Presence of a Helix in Human CD4 Cytoplasmic domain Promotes Binding to HIV-1 Nef Protein", *Biochem Biophys Res Commun.*, vol. 292 No. 3, pp. 734-740, (2002).
Iwai et al., "Recognition of the High Affinity Binding Site in Revresponse Element RNA by the Human Immunodeficiency Virus Type-1 rev Protein", *Nucleic Acids Res.*, vol. 20 No. 24, pp. 6465-6472, (1992).
Sutter et al., "Nonreplicating Vaccinia Vector Efficiently Expresses Recombinant Genes", *Proc Natl Acad Sci.*, vol. 89 No. 22, pp. 10847-10851, (1992).
Mackett et al., "Vaccinia Virus: A Selectable Eukaryotic Cloning and Expression Vector", *Proc Natl Acad Sci*, vol. 79 No. 23, pp. 7415-7419, (1982).
Devereux et al., "A Comprehensive Set of Sequence Analysis Programs for the VAX", *Nucleic Acids Res.*, vol. 12 No. Pt 1, pp. 387-395, (1984).

(Continued)

*Primary Examiner*—Jeffrey S. Parkin
(74) *Attorney, Agent, or Firm*—Law Office of Salvatore Arrigo

(57) ABSTRACT

The invention relates to novel insertion sites useful for the integration of HIV DNA sequences into the MVA genome, and to the resulting recombinant MVA derivatives.

19 Claims, 31 Drawing Sheets

OTHER PUBLICATIONS

Gribskov et al., "Sigma Factors From *E. coli*, B. Subtilis, Phage SP01, and Phage T4 are Homologous Proteins", *Nucleic Acids Res.*, vol. 14 No. 16, pp. 6745-6763, (1986).

Yang et al., "The Multimeriziation of Human Immunodeficiency Virus Type I Vif Protein: A Requirement for Vif Function in the Viral Life Cycle", *J. Biol. Chem.*, vol. 276 No. 7, pp. 4889-4893, (2001).

Khan et al., "Human Immunodeficiency Virus Type 1 Vif Protein is Packaged into the Nucleoprotein Complex Through an Interaction with Viral Genomic RNA", *J. Virol.*, vol. 75 No. 16, pp. 7252-7265, (2001).

Mahalingam et al., "Functional Analysis of the Simian Immunodeficiency Virus Vpx Protein: Identification of Packaging Determinants and a Novel Nuclear Targeting Domain", *J. Virol.*, vol. 75 No. 1, pp. 362-374, (2001).

Bour et al., "The Human Immunodeficiency Virus Type 1 Vpu Protein Specifically Binds to the Cytoplasmic domain of CD4: Implications for the Mechanism of Degradation", *J. Virol.*, vol. 69 No. 3, pp. 1510-1520, (1995).

Han et al., "Transactivation of Heterologous Promoters by HIV-1", *Nucleic Acids Res.*, vol. 19 No. 25, pp. 7225-7229, (1991).

Smith et al., "Comparison of Biosequences", *Adv. Appl. Math* 2, pp. 482-489, (1981).

Schwartz et al., "Matrices for Detecting Distant Relationship", *Atlas of Protein Sequences*, pp. 353-358, (1979).

Wilson et al., "Development of a DNA Vaccine Designed to Induce Cytotoxic T Lymphocyte Responses to Multiple Conserved Epitopes in HIV-1", *J Immuno.*, vol. 171 No. 10, pp. 5611-5623, (2003).

Woodberry et al., "Immunogenicity of a Human Immunodeficiency Virus HIV Polytope Vaccine Containing Multiple HLA A2 HIV CD8+ Cytotoxic T-cell Epitopes", *Virology*, vol. 73, No. 7, pp. 5320-5325, (1999).

Didierlaurent et al., "Attenuated Poxviruses Expressing a Synthetic HIV Protein Stimulate HLA-A2-restricted Cytotoxic T-cell Responses", *Vaccine*, vol. 22 No. 25-26, pp. 3395-3403, (2004).

Kmieciak et al., "Enhancement of Cellular and Humoral Immune Responses to Human Immunodeficiency Virus Type 1 Gag and Pol by a G/P-92 Fusion Protein Expressing Highly Immunogenic Gag p17/p24 and Pol p51 Antigens", *Virology*, vol. 4, No. 6, pp. 306-316, (2001).

Fang et al., "Expression of Vaccinia E3L and K3L Genes by a Novel Recombinant Canarypox HIV Vaccine Vector Enhances HIV-1 Pseudovirion Production and Inhibits Apoptosis in Human Cells", *Virology*, vol. 291, pp. 272-284, (2001).

Antoine et al., "The Complete Genomic Sequence of the Modified Vaccinia Ankara Strain: Comparison with Other Orthopoxviruses", *Virology*, vol. 244, No. 2, pp. 365-396, (1998).

\* cited by examiner

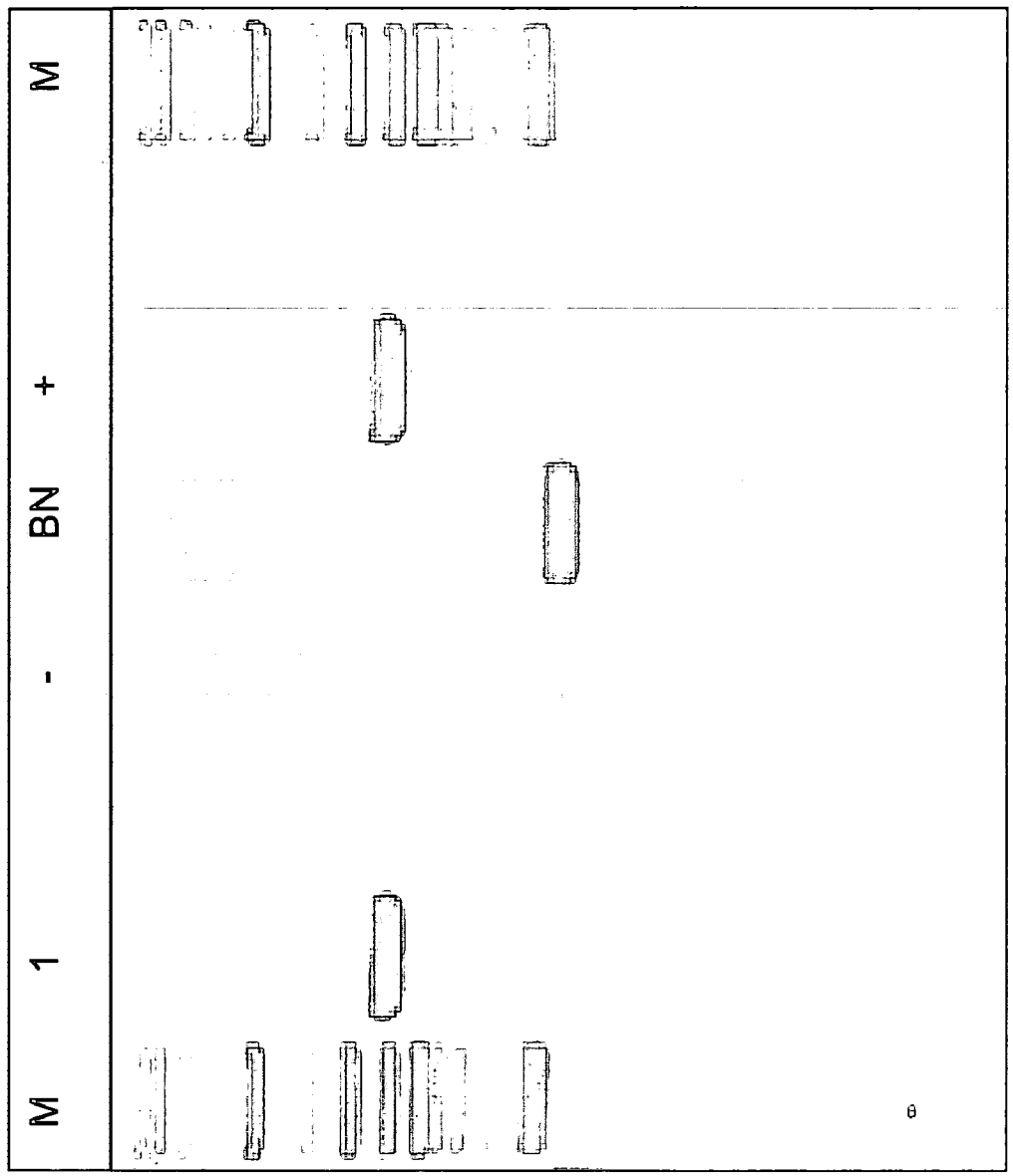

INTERGENIC REGIONS AS NOVEL SITES FOR INSERTION OF HIV DNA SEQUENCES IN THE GENOME OF MODIFIED VACCINIA VIRUS ANKARA

CROSS-REFERENCE TO RELATED APPLICATIONS

The present application is a continuation-in-part of U.S. patent application Ser. No. 10/514,761, filed Nov. 16, 2004, which is the U.S. National Phase of International Application No. PCT/EP03/05045, filed May 14, 2003. The contents of these applications are hereby incorporated herein by reference in their entireties.

FIELD OF THE INVENTION

The invention relates to novel insertion sites useful for the integration of HIV DNA sequences into the Modified Vaccinia Ankara ("MVA") virus genome, and to the resulting recombinant MVA derivatives.

BACKGROUND OF THE INVENTION

Modified Vaccinia Ankara (MVA) virus is a member of the Orthopoxvirus family and has been generated by about 570 serial passages on chicken embryo fibroblasts of the Ankara strain of Vaccinia virus (CVA) (for review see Mayr, A., et al., Infection 3, 6-14 [1975]). As a consequence of these passages, the resulting MVA virus contains 31 kilobases less genomic information compared to CVA, and is highly host-cell restricted (Meyer, H. et al., J. Gen. Virol. 72, 1031-1038 [1991]). MVA is characterized by its extreme attenuation, namely, by a diminished virulence or infectious ability, but still holds an excellent immunogenicity. When tested in a variety of animal models, MVA was proven to be avirulent, even in immuno-suppressed individuals.

The Human Immunodeficiency virus (HIV) is the causative agent of the Acquired Immunodeficiency Syndrome (AIDS). Like all retroviruses, the HIV genome encodes the Gag, Pol and Env proteins. In addition, the HIV genome encodes further regulatory proteins, for example, Tat and Rev, as well as accessory proteins, such as Vpr, Vpx, Vpu, Vif and Nef.

Despite public health efforts to control the spread of the AIDS epidemic, the number of new infections is still increasing. The World Health Organization estimated the global epidemic at 37.8 million infected individuals at the end of the year 2003, and 36.1 million infected individuals at the end of the year 2000, 50% higher than what was predicted on the basis of the data about a decade ago (WHO & UNAIDS. UNAIDS, 2004). Without further improvements on comprehensive prevention mechanisms, the number of new HIV infections to occur, globally, this decade is projected to be 45 million (2004 Report on The Global AIDS Epidemic, UNAIDS and WHO).

Given the steady spread of the epidemic, a number of different HIV-1 vaccine delivery strategies, such as novel vectors or adjuvant systems, have now been developed and evaluated in different pre-clinical settings, as well as in clinical trials. The first vaccine candidate that entered a phase-III clinical trial is based on envelope gp 120 protein in alum formulations (Francis et al., AIDS Res. Hum. Retroviruses 14 (Suppl 3)(5): S325-31 [1998]). The results of the first clinical studies were discouraging.

The viral vaccines that were tested for efficacy in the past are usually based on single HIV proteins, such as Env. However, even if an immune response was generated against such a single protein, for example, Env, the immune response proved ineffective. One reason for the ineffectiveness is the high mutation rate of HIV, in particular with respect to the Env protein, reportedly resulting in viruses, in which the proteins are not recognized by the immune response induced by the vaccine. Since no effective prophylactic treatment is available, there is still a need to bring an effective vaccine to the clinic.

Several excellent properties of the MVA strain pertinent to its use in vaccine development have been demonstrated in extensive clinical trials (Mayr et al., Zbl. Bakt. Hyg. I, Abt. Org. B 167, 375-390 [1987]). During these studies, performed in over 120,000 humans, including high-risk patients, no side effects were seen (Sticki et al., Dtsch. med. Wschr. 99, 2386-2392 [1974]).

It has been further found that MVA is blocked in the late stage of the virus replication cycle in mammalian cells (Sutter, G. and Moss, B., Proc. Natl. Acad. Sci. USA 89, 10847-10851 [1992]). Accordingly, MVA fully replicates its DNA, synthesizes early, intermediate, and late gene products, but is not able to assemble mature infectious virions, which could be released from an infected cell. For this reason, namely, its replication-restricted nature, MVA serves as a gene expression vector.

More recently, MVA was used to generate recombinant vaccines, expressing antigenic sequences inserted either at the site of the thymidine-kinase (tk) gene (U.S. Pat. No. 5,185,146), or at the site of a naturally occurring deletion within the MVA genome (PCT/EP96/02926).

However, although the tk insertion locus is widely used for the generation of recombinant poxviruses, particularly for the generation of recombinant Vaccinia viruses (Mackett, et al. P.N.A.S. USA 79, 7415-7419 [1982]), use of this technology in MVA has several drawbacks. It was reported by Scheiflinger et al. that MVA is much more sensitive to modifications of the genome, when compared to other poxviruses, which can be used for the generation of recombinant poxviruses. Scheiflinger et al. reported, in particular, that one of the most commonly used sites for the integration of heterologous DNA into poxviral genomes, namely, the thymidine kinase (tk) gene locus, cannot be used to generate stable recombinant MVA. Any resulting tk(−) recombinant MVA proved to be highly unstable and, upon purification, immediately deleted the inserted DNA, together with parts of the genomic DNA of MVA (Scheiflinger et al., Arch Virol 141: pp 663-669 [1996]).

Instability and, thus, high probability of genomic recombination is a known problem within pox virology, and a drawback for vaccine production. Actually, MVA was established during long-term passages exploiting the fact that the viral genome of CVA is unstable when propagated in vitro in tissue cultured cells. Several thousands of nucleotides (31 kb) had been deleted in the MVA genome, which, therefore, is characterized by 6 major deletions, and numerous small deletions, in comparison to the original CVA genome.

The genomic organization of the MVA genome has been described recently (Antoine et al., Virology 244, 365-396 [1998]). The 178 kb genome of MVA is densely packed and comprises 193 individual open reading frames (ORFs), which code for proteins of at least 63 amino acids in length. In comparison with the highly infectious Variola virus, and also with the prototype of Vaccinia virus, namely the strain Copenhagen, the majority of ORFs of MVA are fragmented or truncated (Antoine et al., Virology 244, 365-396 [1998]). However, with very few exceptions, all ORFs, including the fragmented and truncated ORFs, get transcribed and translated into proteins. In the following description of the invention, the nomenclature of Antoine et al. (supra) is used and, where appropriate, the nomenclature based on HindIII restriction enzyme digest is also indicated.

To date, only the insertion of exogenous DNA into the naturally occurring deletion sites of the MVA genome reportedly led to stable recombinant MVAs (PCT/EP96/02926). Unfortunately, there are only a restricted number of naturally occurring deletion sites in the MVA genome. Thus, a need exists for the identification of additional stable insertion sites, particularly those that can be useful for generation of MVA-based vaccines for treatment and/or prevention of AIDS.

SUMMARY OF THE INVENTION

Accordingly, this invention provides further insertion sites of the MVA genome, and provides insertion vectors that direct the stable insertion of exogenous DNA sequences into these newly identified insertion sites of the MVA genome.

Furthermore, with the recombinant MVA according to the invention it is now possible to stably express multiple HIV proteins per recombinant MVA virus. The expression of multiple proteins, instead of one HIV protein per virus, is able to induce a wide range of immune responses. Thus, the likelihood is increased that a protective immune response is generated that is effective against different HIV isolates.

To achieve the objects in accordance with the purpose of the invention, as embodied and broadly described herein, the invention comprises the following elements.

A recombinant Modified Vaccinia Ankara (MVA) virus comprising one or more human immunodeficiency virus DNA coding sequences inserted into one or more of newly described intergenic regions (IGRs) of the viral genome.

A recombinant MVA virus wherein the HIV coding sequences are inserted under the transcriptional control of one or more poxviral transcription control elements, such as, for example, the ATI promoter, or the p7.5 promoter.

A method for inducing an immune response comprising: (a) providing a composition comprising a recombinant MVA virus of the invention; and (b) administering the composition to a subject animal, for example, to a human.

A method of producing an HIV-1 protein, polypeptide, peptide, antigen, or epitope in vitro comprising the steps of: (a) infection of a host cell with the recombinant MVA virus of the invention; and (b) cultivation of the infected host cell under suitable conditions to produce the polypeptide, protein, peptide, antigen, or epitope.

A method of introducing an HIV DNA sequence into a cell ex vivo comprising: (a) infecting the cell with a recombinant MVA virus of the invention; and, optionally, (b) administering the infected cell to a subject animal, for example, to a human.

A method of introducing an HIV DNA sequence into a subject, said method comprising administering a recombinant MVA of the invention to a subject animal.

A host cell comprising a recombinant MVA of the invention, wherein the host cell is chosen from a prokaryotic cell and a eukaryotic cell, such as, for example, a human cell, a non-human mammalian cell, an insect cell, a fish cell, a plant cell, or a fungal cell.

Additional objects and advantages of the invention will be set forth in part in the description that follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The invention is more thouroughly understood in view of the drawings, in which:

FIGS. 1A-1C illustrate restriction maps of the vector constructs pBNX39 (FIG. 1A), pBNX70 (FIG. 1B), and pBN84 (FIG. 1C), comprising about 600 bp of MVA sequences flanking the insertion site after the I4L ORF. The plasmids additionally comprise exogenous DNA (Ecogpt and hBFP) under the transcriptional control of a poxvirus promoter (P or Ps) between the flanking sequences: Flank 1 (F1 I4L-I5L) and Flank 2 (F2 I4L-I5L). F1rpt stands for a repetitive sequence of Flank 1 to allow deletion of the reporter cassette from a resulting recombinant virus. pBN84 (FIG. 1C) additionally codes for the Dengue virus NS1 protein (NS1 DEN). Further abbreviations: AmpR=Ampicilin resistance gene; bps=base pairs; Ecogpt=phosphoribosyltransferase gene isolated from *E. coli;* and hBFP=sequence for blue fluorescence protein.

FIGS. 2A-2C illustrate restriction maps of the vector constructs pBNX51 (FIG. 2A), pBNX67 (FIG. 2B), and pBN27 (FIG. 2C), comprising about 600 bp of MVA sequences flanking the insertion site after the ORF 137L (Flank 1: F1 136-137 corresponds to position 129340-129930 of the MVA genome; Flank 2: F2 136-137 corresponds to position 129931-130540 of the MVA genome).

Additionally, the vector pBNX67 (FIG. 2B) comprises exogenous DNA (NPT II gene=neomycin resistance) under the transcriptional control of a poxvirus promoter (P or Ps) between the flanking sequences. F2rpt stands for a repetitive sequence of Flank 2 to allow deletion of the reporter cassette from a resulting recombinant virus. pBN27 (FIG. 2C) additionally codes for the Dengue virus PrM4 under control of a poxvirus promoter. Further abbreviations: AmpR=Ampicilin resistance gene; bps=base pairs; IRES=internal ribosomal entry site; EGFP=gene for the enhanced green fluorescent protein.

FIGS. 3A-3E illustrate restriction maps of the vector constructs pBNX79 (FIG. 3A), pBNX86 (FIG. 3B), pBNX88, (FIG. 3C), pBN34 (FIG. 3D), and pBN56 (FIG. 3D), comprising about 600 bps of MVA sequences flanking the insertion site between the ORF 007R and 008L (Flank 1: F1 IGR 07-08 starts at position 12200 of the MVA genome; Flank 2: F2 IGR 07-08 stops at position 13400 of the MVA genome). F2rpt stands for a repetitive sequence of Flank 2 to allow deletion of the reporter cassette from a resulting recombinant virus. Additionally, the vectors pBNX88 (FIG. 3C) and pBNX86 (FIG. 3B) comprise exogenous DNA (BFP+gpt and NPT II+EGFP, respectively) under the transcriptional control of a poxvirus promoter (P) between the flanking sequences. F2rpt stands for a repetitive sequence of Flank 2 to allow deletion of the reporter cassette from a resulting recombinant virus. pBN56 (FIG. 3E) additionally codes for the HIV-1 env protein, and pBN34 (FIG. 3D) contains the Dengue virus PrM2 coding sequence, env and PrM2 being under control of the poxvirus promoters prATI and p7.5, respectively. Further abbreviations: AmpR=Ampicilin resistance gene; bps=base pairs.

FIGS. 4A-4C illustrate the restriction maps of the vector constructs pBNX80 (FIG. 4A), pBNX87 (FIG. 4B), and pBN47 (FIG. 4C) comprising about 600/640 bps of MVA sequences flanking the insertion site between the ORF 044L and 045L (Flank 1: F1 IGR44-45 starts at position 36730 of the MVA genome; Flank 2: F2 IGR44-45 stops at position 37970 of the MVA genome). Additionally the vector pBNX87 (FIG. 4B) comprises exogenous DNA (NPT II gene+EGFP) under the transcriptional control of a poxvirus promoter (P) between the flanking sequences. F2rpt stands for a repetitive sequence of Flank 2 to allow deletion of the reporter cassette from a resulting recombinant virus. pBN47 (FIG. 4C) additionally codes for the Dengue virus PrM3 under the control of a poxvirus promoter (pr7.5). Further abbreviations: AmpR=Ampicilin resistance gene; bps=base pairs.

FIGS. 5A-5C illustrate the restriction maps of the vector constructs pBNX90 (FIG. 5A), pBNX92 (FIG. 5B), and pBN54 (FIG. 5C), comprising about 596/604 bps of MVA sequences flanking the insertion site between the ORF 148R and 149L (Flank 1: F1 IGR148-149 starts at position 136900 of the MVA genome; Flank 2: F2 IGR148-149 stops at position 138100 of the MVA genome). Additionally the vector pBNX92 (FIG. 5B) comprises exogenous DNA (Ecogpt+hBFP) under the transcriptional control of a poxvirus promoter (P) between the flanking sequences. pBN54 (FIG. 5C) additionally codes for the Dengue virus PrM1 under the control of the poxvirus promoter pr7.5. F2rpt stands for a repetitive sequence of Flank 2 to allow deletion of the reporter cassette from a resulting recombinant virus. Further abbreviations: AmpR=Ampicilin resistance gene; bps=base pairs.

FIG. 6 shows a schematic presentation of the intergenic insertion sites of MVA (GenBank Accession No. U94848).

FIG. 7 illustrates the results of the PCR analysis of IGR I4L-I5L in recombinant MVA with the Dengue virus NS1 inserted in the IGR I4L-I5L. Lane "BN" shows the PCR product using MVA-BN empty vector. Using the NS1 recombinant MVA, a fragment of bigger size is detectable (1, 2, 3, 4: different concentrations of DNA). M=Molecular weight marker, −=water negative control.

FIG. 8A illustrates the results of the PCR analysis of IGR 136-137 in recombinant MVA with the Dengue virus PrM4 inserted in the IGR 136-137. Lane "BN" shows the PCR product using MVA-BN empty vector. Using the PrM4 recombinant MVA, a fragment of bigger size is detectable (mBN23, 1/10, 1/100: different concentrations of DNA). 1 kb=Molecular weight marker, H2O=water negative control, pBN27=plasmid positive control.

FIG. 8B shows the multiple step growth curve for MVA-BN empty vector and the recombinant MVA with PrM4 inserted in IGR 136-137 (MVA-mBN23).

FIG. 9A illustrates the results of the PCR analysis of IGR 07-08 in recombinant MVA with the Dengue virus PrM2 inserted in the IGR 07-08. Lane 3 shows the PCR product using MVA-BN empty vector. Using the PrM2 recombinant MVA, a fragment of bigger size is detectable (lane 2). M=Molecular weight marker, lane 1=water negative control.

FIG. 9B shows the multiple step growth curve for MVA-BN empty vector and the recombinant MVA with PrM2 inserted in IGR 07-08 (MVA-mBN25).

FIG. 10 illustrates the results of the PCR analysis of IGR 07-08 in recombinant MVA, with the HIV env inserted in the IGR 07-08. Lane BN shows the PCR product using MVA-BN empty vector. Using the PrM2 recombinant MVA, a fragment of bigger size is detectable (lane 1, 2, 3). M=Molecular weight marker, −=water negative control, +=plasmid positive control.

FIG. 11A illustrates the results of the PCR analysis of IGR 44-45 in recombinant MVA with the Dengue virus PrM3 inserted in the IGR 44-45. Lane BN shows the PCR product using MVA-BN empty vector. Using the PrM3 recombinant MVA, a fragment of bigger size is detectable (lane 1-4, different concentrations of DNA). M=Molecular weight marker, −=water negative control.

FIG. 11B shows the multiple step growth curve for MVA-BN empty vector and the recombinant MVA with PrM3 inserted in IGR 44-45 (MVA-mBN28).

FIG. 12A illustrates the results of the PCR analysis of IGR 148-149 in recombinant MVA with the Dengue virus PrM1 inserted in the IGR 148-149. Lane BN shows the PCR product using MVA-BN empty vector. Using the PrM1 recombinant MVA, a fragment of bigger size is detectable (lane 1). M=Molecular weight marker, −=water negative control, +=plasmid positive control.

Figure 13A:
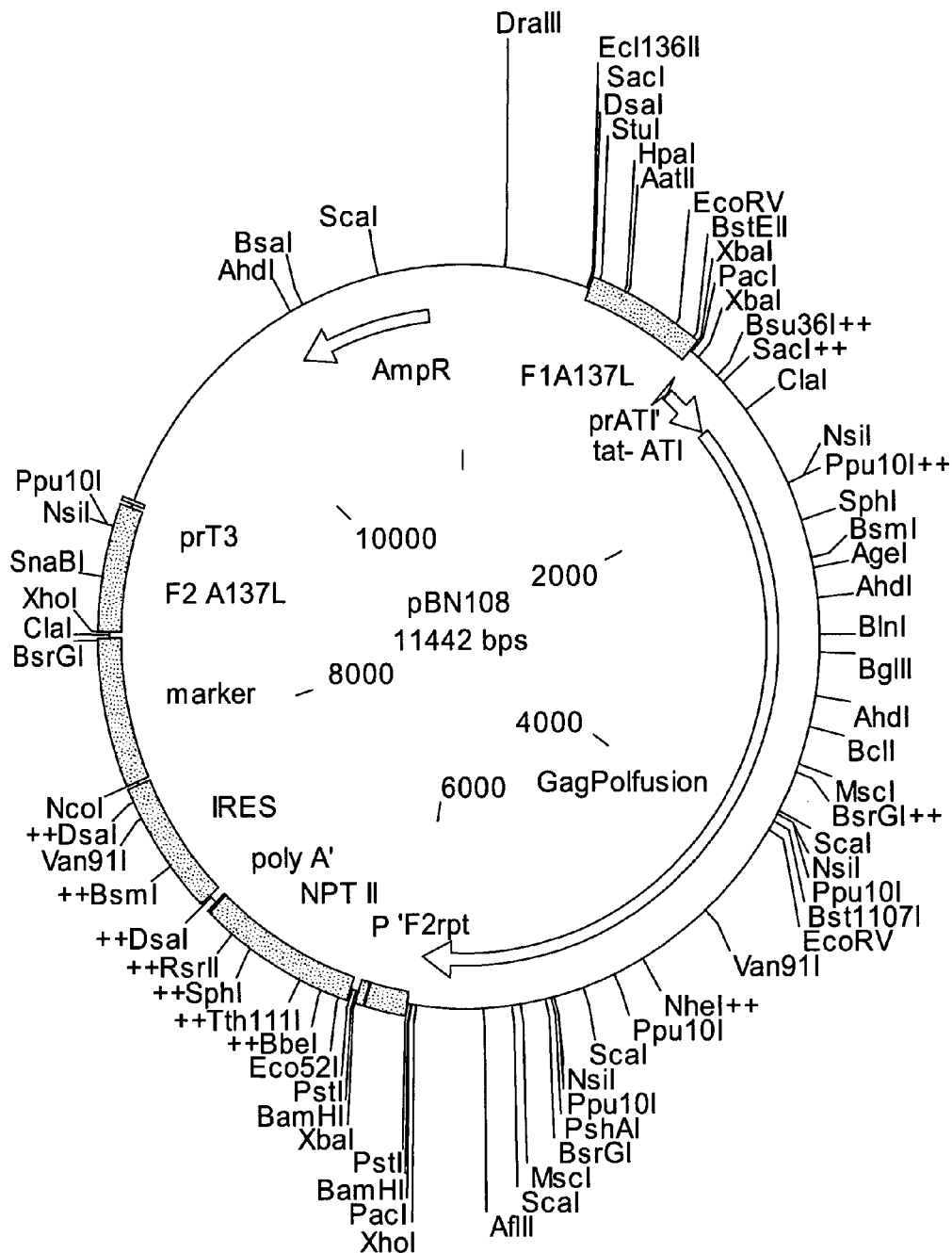
FIGS. 13A-13C illustrate the restriction maps of the recombination vectors pBN108 (td tat-gag/pol) (FIG. 13A), pBN131 (truncated nef) (FIG. 13B), and pBN175 (vif-vpr-vpu-rev) (FIG. 13C).

FIG. 13A illustrates the recombination vector pBN108, which was created by insertion of expression cassettes for transdominant tat and GagPol fusion protein, each under control of the ATI promoter (prATI), in the PacI site of pBNX67 (see FIG. 2B), and expresses the transdominant tat and gag/pol in the IGR 136-137 of the MVA genome. The resulting vector, pBN108, also contains the NPTII gene for selection.

Figure 13B:
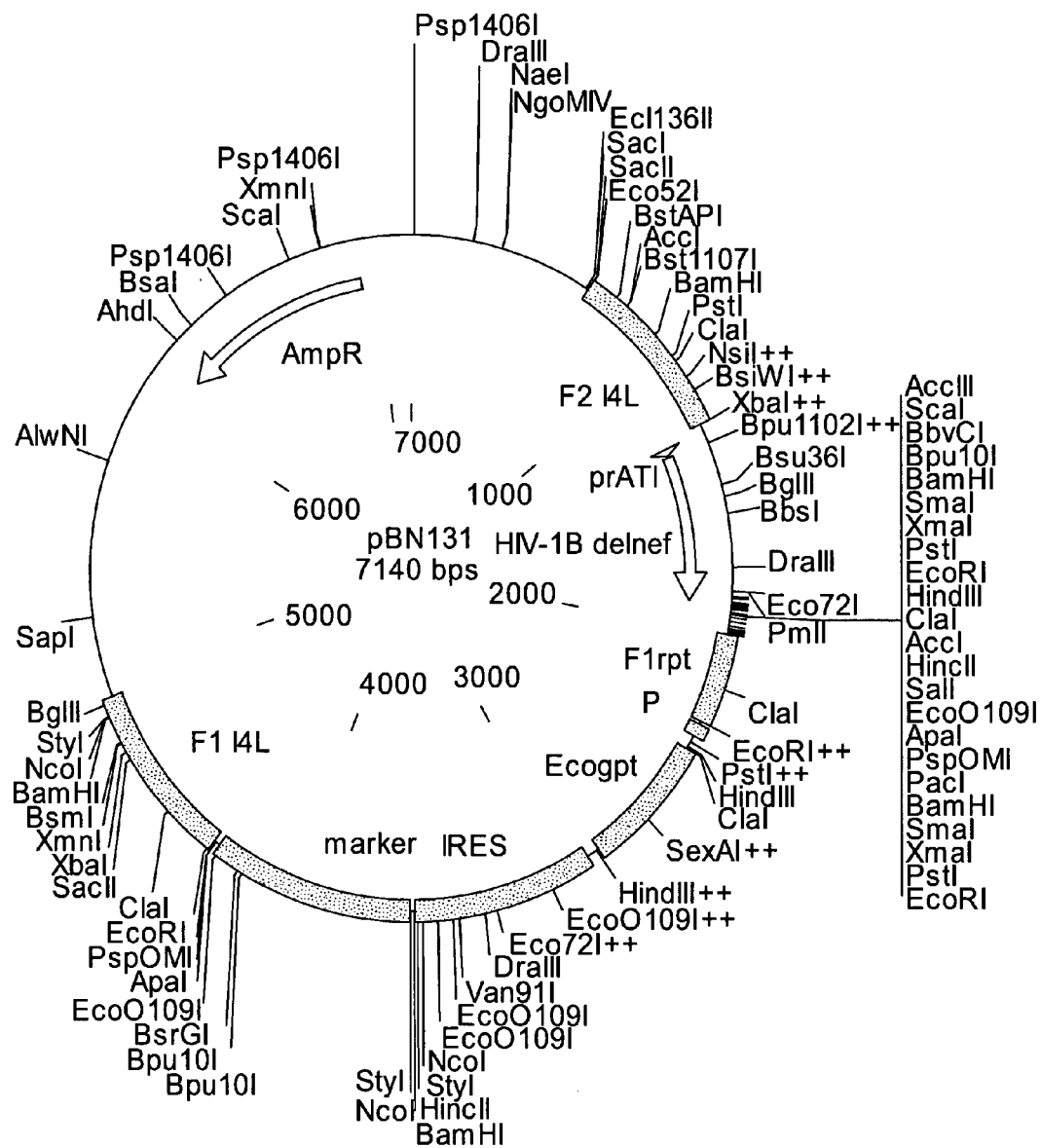

FIG. 13B illustrates the recombination vector pBN131, created for insertion of the truncated nef (HIV-IBdelnef) in the IGR I4L-I5L of the MVA genome. pBN131 was created by insertion of an expression cassette comprising a truncated nef under the control of an ATI promoter in the PacI restriction site of the vector pBNX59.

Figure 3A:
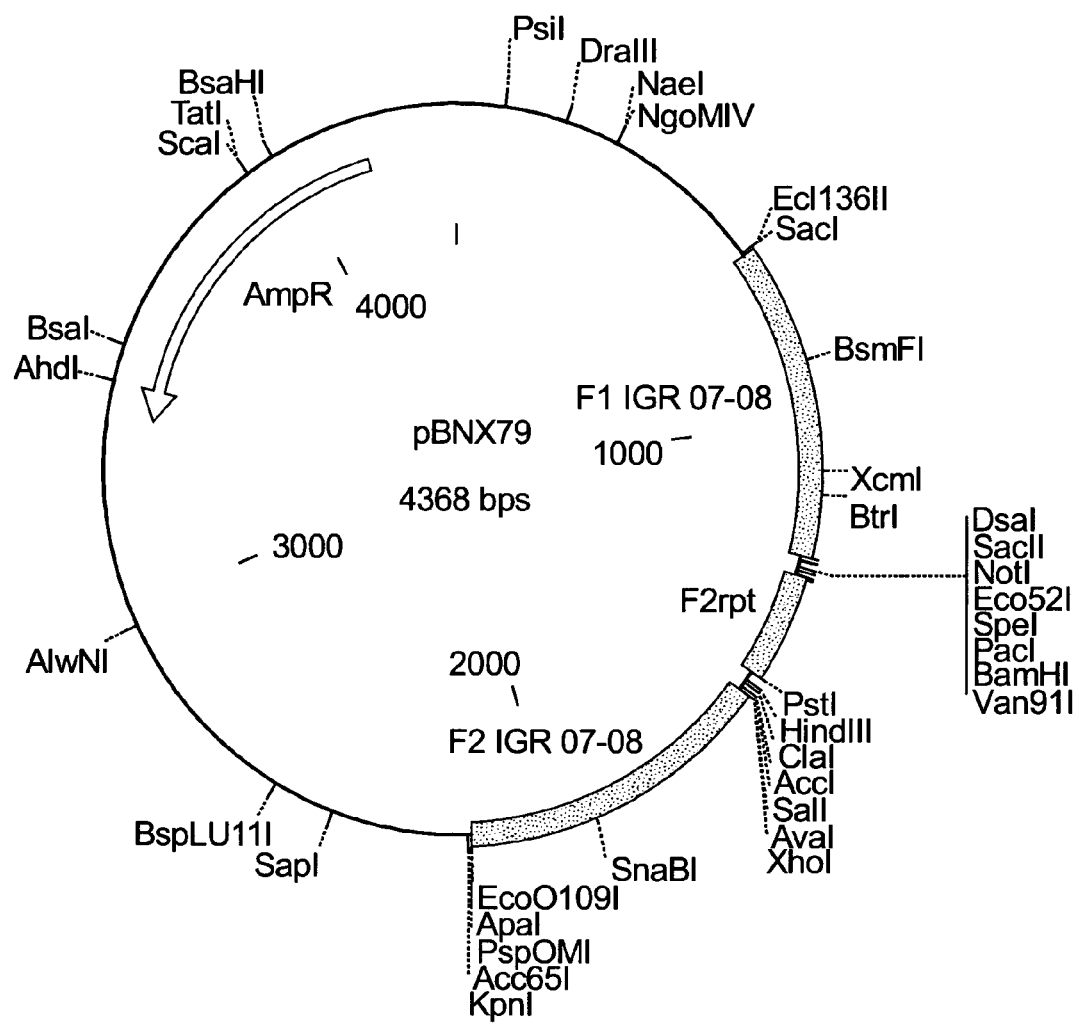
Figure 3B:
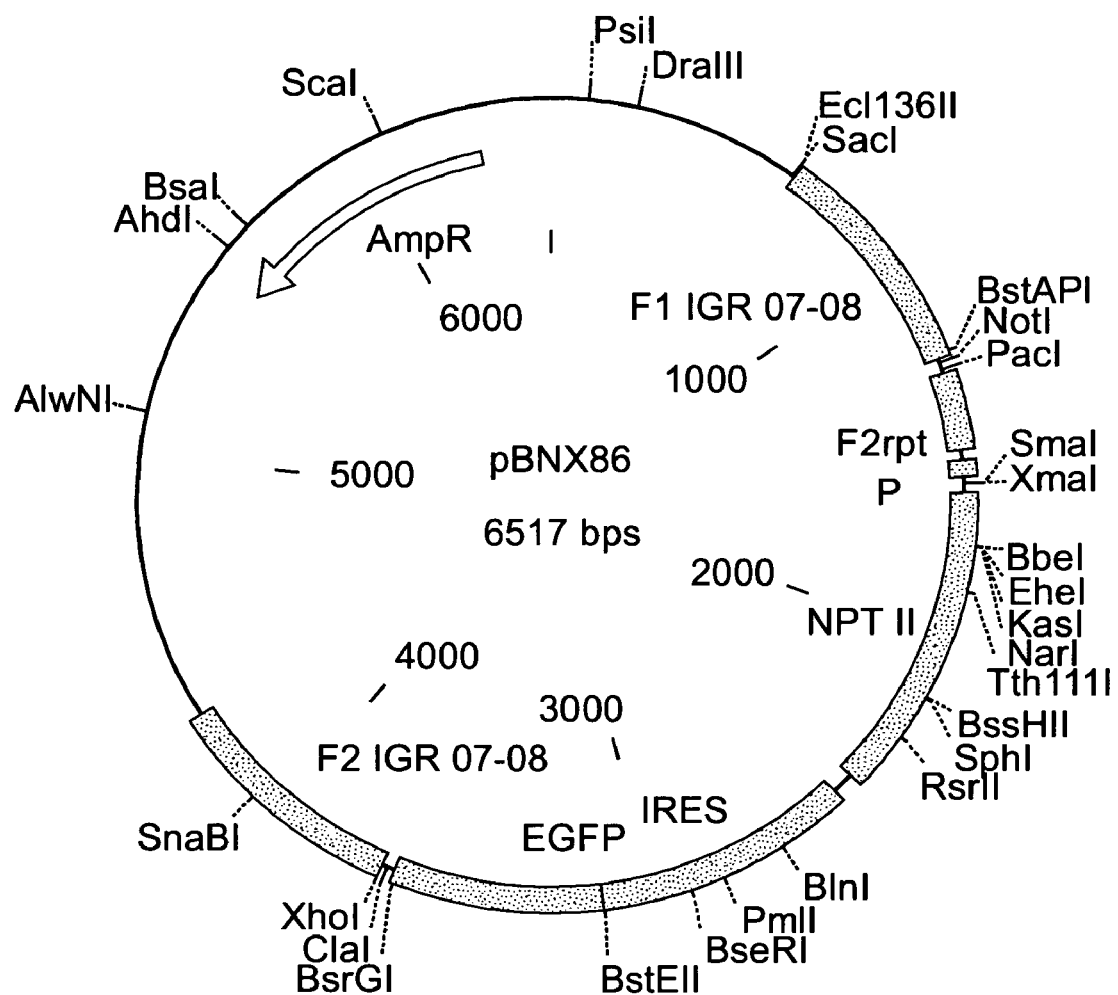
Figure 13C:
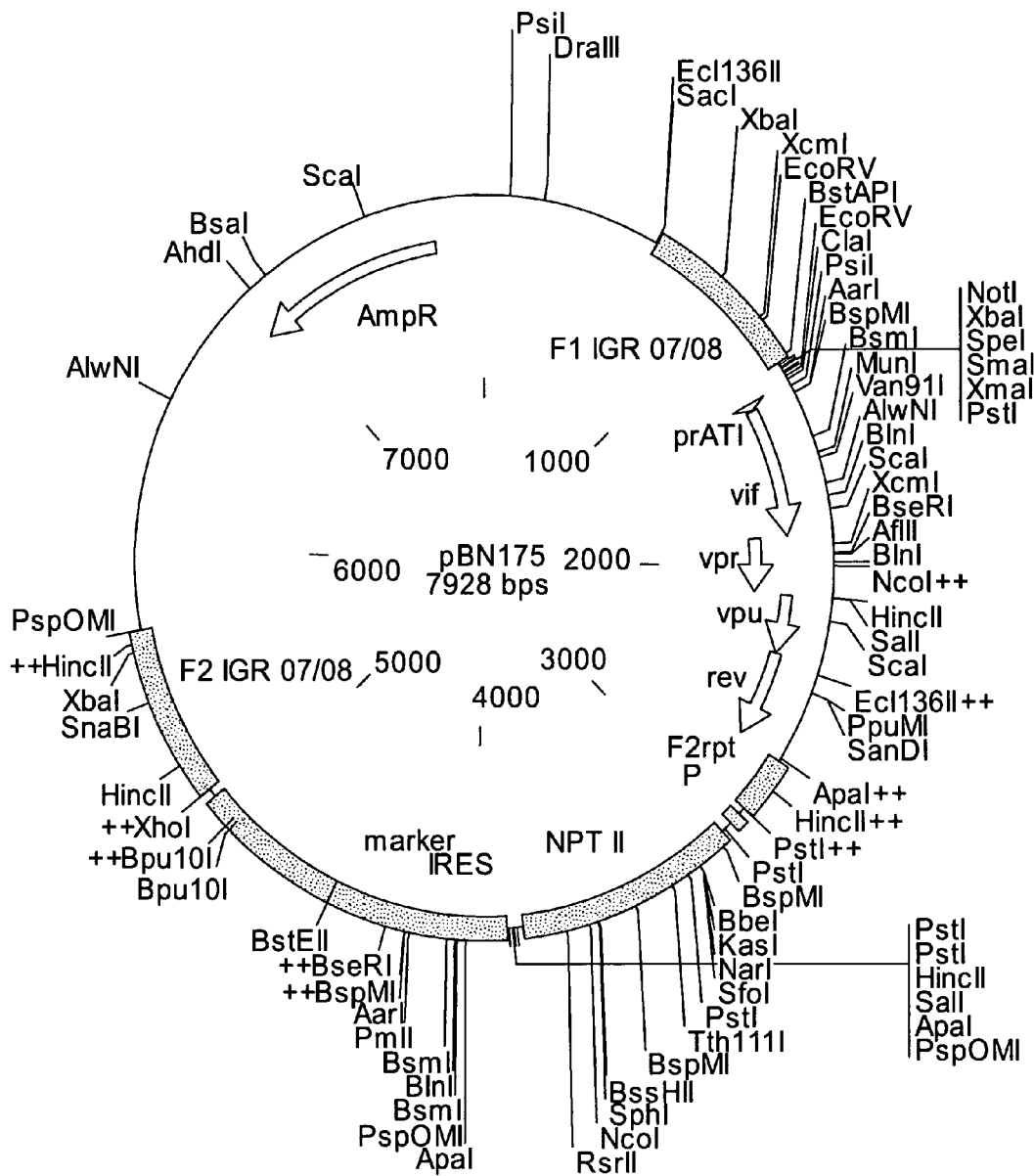

FIG. 13C illustrates the recombination vector pBN17, created for insertion of the vif-vpr-vpu-rev fusion protein in the IGR 07-08 of the MVA genome. pBN17 was created by insertion of an expression cassette comprising the vif-vpr-vpu-rev coding sequence under the control of the ATI promoter in the NotI restriction site of the vector pBNX86 (see FIG. 3B). Additional abbreviations: marker=EGFP.

DETAILED DESCRIPTION OF THE INVENTION

Reference will now be made in detail to various embodiments of the invention, examples of which are illustrated in the accompanying drawings.

The term "intergenic regions" (IGRs) of the viral genome refers to regions of the MVA viral genome, wherein the regions are, in turn, located between or, in certain embodiments, are flanked by two adjacent open reading frames (ORFs) of the MVA genome. For example, if the IGR comprises a sequence that is not part of either ORF but exists between the two adjacent ORFs, then the IGR is said to be "located between" two adjacent ORFs. On the other hand, there are situations in which there is no additional sequence that exists between the two adjacent ORFs. In other words, the two adjacent ORFs abut. In the latter situations then, the IGR does not have a corresponding sequence in itself; rather, the IGR refers to the site, or genomic position, whereby an heterologous sequence can be inserted between the two ORFs, thus enlarging the distance separating the otherwise abutting ORFs. In this case, the IGR is said to be "flanked by" two adjacent ORFs.

"ORFs of the MVA genome" occur in two coding directions: forward and reverse (for detailed description, see for example, Antoine et al., Virology 244, 365-396 [1998]), incorporated herein by reference). Consequently, the polymerase activity occurs from left to right, i.e., forward direction and, correspondingly, from right to left, reverse direction. In certain embodiments of the invention, ORFs occuring in the forward coding direction are referred to as 5'ORF3', whereas ORFs occurring in the reverse coding direction are referred to as 3'FRO5' to facilitate the understanding of their orientation in the MVA genome.

It is common practice in poxvirology, and it became a standard classification for Vaccinia viruses, to identify ORFs by their orientation and their position on the different HindIII restriction digest fragments of the genome (see for example, Goebel et al., Virology 179, 247-266 and 517-563, [1990]; and Massung, R. F. et al., Virology 201, 215-240 [1994], incorporated herein by reference). For the common practice nomenclature, the different HindIII fragments are named by descending capital letters corresponding with their descending size. The ORFs are numbered from left to right on each HindIII fragment and the orientation of the ORF is indicated by a capital L (standing for transcription from right to Left) or R (standing for transcription from left to Right).

Additionally, there is a more recent publication of the MVA genome structure, which uses a different nomenclature, simply numbering the ORF from the left to the right end of the genome, and indicating their orientation with a capital L or R (Antoine et al., Virology 244, 365-396 [1998]). As an example the I4L ORF, according to the old nomenclature, corresponds to the 064L ORF according to Antoine et al. If not indicated differently, the invention uses the nomenclature according to Antoine et al.

Accordingly, herein, the IGRs are referred to in one of two ways, depending on the nomenclature used to name the ORFs. For example, an IGR located between the two adjacent ORFs, ORF 001L and ORF 002L, is said to be IGR 001L-002L. An IGR located between the two adjacent ORFs, ORF I4L and ORF I5L, is said to be IGR I4L-I5L.

Herein, and according to the old nomenclature, ORF 006L corresponds to C10L, 019L corresponds to C6L, 020L to N1L, 021L to N2L, 023L to K2L, 028R to K7R, 029L to F1L, 037L to F8L, 045L to F15L, 050L to E3L, 052R to E5R, 054L to E7R, 055R to E8R, 056L to E9L, 062L to I1L, 064L to I4L, 065L to I5L, 081R to L2R, 082L to L3L, 086R to J2R, 088R to J4R, 089L to J5L, 092R to H2R, 095R to H5R, 107R to D10R, 108L to D11L, 122R to A11R, 123L to A12L, 125L to A14L, 126L to A15L, 135R to A24R, 136L to A25L, 137L to A26L, 141L to A30L, 148R to A37R, 149L to A38L, 152R to A40R, 153L to A41L, 154R to A42R, 157L to A44L, 159R to A46R, 160L to A47L, 165R to A56R, 166R to A57R, 167R to B1R, 170R to B3R, 176R to B8R, 180R to B12R, 184R to B16R, 185L to B17L, and 187R to B19R.

Accordingly, IGR I4L-I5L (old nomenclature) corresponds to IGR 064L-065L (new nomenclature), and refers to the intergenic region located between, or flanked by, ORFs I4L and I5L.

Furthermore, unless immediately preceeded by the term "IGR" and thus specified as referring to an IGR, the use of the term I4L-I5L refers to the pair of ORFs I4L and I5L; it is not to be confused with IGR I4L-I5L, which refers to the region located in between, or flanked by, the ORFs I4L and I5L. By analogy, the use of the expression, for example, "a group of ORFs selected from 001L-002L, 002L-003L, 005R-006R," is synonymous with the use of the expression, and refers to, "a group of pairs of ORFs selected from the pair 001L and 002L; the pair 002L and 003L; and the pair 005R and 006R."

In one embodiment, reference is made to the various HIV sequences as disclosed in the GenBank database, in particular to the sequence of the HIV-1 isolate HXB2R having the GenBank accession number K03455.

The term "derivative of the amino acid sequence of an HIV protein," as used in the present specification, refers to HIV proteins that have an altered amino acid sequence compared to the corresponding naturally occurring HIV protein. An altered amino acid sequence may be a sequence in which one or more amino acids of the sequence of the HIV protein are substituted, inserted, or deleted; for example, the derivative can have one or more conservative amino acid substitutions. More particularly, a "derivative of the amino acid sequence of an HIV protein" is an amino acid sequence showing an identity of at least 50%, such as of at least 70%, of at least 80%, or even of at least 90%, when the corresponding part of the amino acid sequence in the fusion protein is compared to the amino acid sequence of the respective HIV protein of known HIV isolates.

According to the invention, an amino acid sequence is regarded as having the above indicated sequence identity even if the identity is found for the corresponding protein of only one HIV isolate, irrespective of the fact that there might be corresponding proteins in other isolates showing a lower identity. By way of example, if a Vpr derivative in the fusion protein shows an identity of 95% to the Vpr sequence of one HIV isolate, but only an identity of 50-70% to (all) other HIV isolates, the identity of said Vpr derivative is regarded as being of at least 90%.

In a preferred embodiment, the term "derivative of an HIV protein" refers to an amino acid sequence showing an identity of at least 50%, 70%, 80%, or 90% to the respective HIV protein in the HIV-1 isolate HXB2R (GenBank accession number K03455).

The percent identity may be determined, for example, by comparing sequence information using the GAP computer program, version 6.0 described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482,1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745,1986, as described by Schwartz and Dayhoff, eds., *Atlas of Protein Sequence and Structure*, National Biomedical Research Foundation, pp. 353-358,1979; (2) a penalty of 3.0 for each gap and an additional 0.10 penalty for each symbol in each gap; and (3) no penalty for end gaps. Other programs used by one skilled in the art of sequence comparison may also be used.

New Sites for Insertion of Exogenous DNA Sequences into the MVA Genome

In one embodiment, the invention encompasses new sites for the insertion of exogenous DNA sequences into the genome of Modified Vaccinia Ankara (MVA) virus. The new insertion sites are located in the intergenic regions (IGRs) of the viral genome, wherein the IGRs are, in turn, either located between, or are flanked by, two adjacent open reading frames (ORFs) of the MVA genome.

Accordingly, in certain embodiments, the invention relates to recombinant MVA viruses comprising one or more HIV DNA sequences inserted into one or more of the IGRs of the invention.

It was surprisingly found that exogenous DNA sequences remain stable when inserted into IGRs of the MVA genome. These results were unexpected because, as already indicated above, the genome of MVA reportedly is unstable. Reportedly, genes or DNA sequences non-essential for propagation of the virus are deleted or fragmented. Indeed, whereas it has also been reported that stable recombinant MVAs are obtained when heterologous DNA sequences are inserted into the naturally occurring deletion sites of the MVA genome (PCT/EP96/02926), which was another surprising observation in itself. Typically, host range genes are not suitable insertion sites in MVAs. Such is the case of, for example, the tk-locus widely used for the generation of other recombinant poxviruses. The fact that Vero-MVA has one extra genomic deletion (PCT/EP01/02703) also suggests that the genome is dynamic, in the sense that it readily deletes genes that are not required for propagation. Therefore, and contrary to the results of the invention, one skilled in the art would have reasonably expected that heterologous DNA sequences non-essential for viral propagation, when inserted into spaces between ORFs, would be deleted by the MVA virus as well.

While the nucleotide sequence of an ORF encodes an amino acid sequence forming a peptide, polypeptide, or protein, the IGRs between two ORFs have no coding capacity. Accordingly, in certain embodiments, the IGRs may comprise regulatory elements, binding sites, promoter and/or enhancer sequences essential for, or involved in, the transcriptional control of the viral gene expression. Thus, the IGR may be involved in the regulatory control of the viral life cycle.

In further embodiments, however, the inventors of the invention have also found that the newly identified insertion sites have the unexpected advantage that exogenous DNA sequences can be stably inserted into the MVA genome, and furthermore, have such capability without influencing or changing the typical characteristics and gene expression of MVA (for example, see FIGS. 6 through 12). The new insertion sites also are especially useful because no ORF or coding sequence of MVA is altered by the process of insertion.

Moreover, it was surprisingly found that the expression level of a foreign gene inserted into an IGR is higher than the expression level of a foreign gene inserted into a deletion site of the MVA genome (see also Example 1).

According to the invention, the nucleotide sequence of an ORF should start with a start codon and end with a stop codon. Depending on the orientation of the two adjacent ORFs, the IGR, i.e., the region in between these ORFs, is flanked by one of the following: the two stop codons of the two adjacent ORFs; the two start codons of the two adjacent ORFs; the stop codon of the first ORF and the start codon of the second ORF; or the start codon of the first ORF and the stop codon of the second ORF.

Accordingly, in one embodiment, the site for insertion of the exogenous DNA sequence into the IGR is downstream, i.e. 3', of the stop codon of a first ORF; and, in case the adjacent ORF, also termed second ORF, has the same orientation as the first ORF, the insertion site further lies upstream, i.e. 5', of the start codon of the second ORF. This arrangement can be represented as: 5'ORF3'-IGR-5'ORF3'.

In a further embodiment, the site for insertion of the exogenous DNA sequence into the IGR is downstream, i.e. 3', of the stop codon of a first ORF; and, in case the second ORF has an opposite orientation relative to the first ORF, which means the orientation of the two adjacent ORFs points to each other, the insertion site further lies downstream of the stop codons of both ORFs. This arrangement can be represented as: 5'ORF3'-IGR-3'FRO5'.

In yet a further embodiment, in case the two adjacent ORFs read in the same direction from right to left of the viral genome, which is synonymous with a positioning that is characterized in that the start codon of the first ORF is adjacent to the stop codon of the second ORF, then the exogenous DNA is inserted upstream (or 5') of one start codon and downstream (or 3') from the other. This arrangement can be represented as: 3'FRO5'-IGR-3'FRO5'.

In yet a further embodiment, in case the two adjacent ORFs read in opposite direction, but the orientation of the two adjacent ORFs points away from each other, which is synonymous with a positioning that is characterized in that the start codons of the two ORFs are adjacent to each other, then the exogenous DNA is inserted upstream relative to both start codons. This arrangement can be represented as: 3'FRO5'-IGR-5'ORF3'.

In one embodiment, heterologous DNA sequences can be inserted into one or more IGRs in between two adjacent ORFs, said IGR selected from the group comprising: 001L-002L, 002L-003L, 005R-006R, 006L-007R, 007R-008L, 008L-009L, 017L-018L, 018L-019L, 019L-020L, 020L-021L, 023L-024L, 024L-025L, 025L-026L, 028R-029L, 030L-031L, 031L-032L, 032L-033L, 035L-036L, 036L-037L, 037L-038L, 039L-040L, 043L-044L, 044L-045L, 046L-047R, 049L-050L, 050L-051L, 051L-052R, 052R-053R, 053R-054R, 054R-055R, 055R-056L, 061L-062L, 064L-065L, 065L-066L, 066L-067L, 077L-078R, 078R-079R, 080R-081R, 081R-082R, 082L-083R, 085R-086R, 086R-087R, 088R-089L, 089L-090R, 092R-093L, 094L-095R, 096R-097R, 097R-098R, 101R-102R, 103R-104R, 105L-106R, 107R-108L, 108L-109L, 109L-110L, 110L-111L, 113L-114L, 114L-115L, 115L-116R, 117L-118L, 118L-119R, 122R-123L, 123L-124L, 124L-125L, 125L-126L, 133R-134R, 134R-135R, 136L-137L, 137L-138L, 141L-142R, 143L-144R, 144R-145R, 145R-146R, 146R-147R, 147R-148R, 148R-149L, 152R-153L, 153L-154R, 154R-155R, 156R-157L, 157L-158R, 159R-160L, 160L-161R, 162R-163R, 163R-164R, 164R-165R, 165R-166R, 166R-167R, 167R-168R, 170R-171R, 173R-174R, 175R-176R, 176R-177R, 178R-179R, 179R-180R, 180R-181R, 183R-184R, 184R-185L, 185L-186R, 186R-187R, 187R-188R, 188R-189R, 189R-190R, 192R-193R.

In a preferred embodiment, the heterologous sequence is inserted into an IGR flanked by two adjacent ORFs selected from the group comprising 007R-008L, 018L-019L, 044L-045L, 064L-065L, 136L-137L, 148R-149L.

Recombinant MVA Comprising DNA Sequences Inserted into Novel IGRs MVA Viruses

In a preferred embodiment, the recombinant MVA virus of the invention is replication incompetent in humans and non-human primates. The terms MVA virus that is "replication incompetent" in humans and/or non-human primates, and the synonymous term virus that is "not capable of being replicated to infectious progeny virus" in humans and/or non-human primates, both refer preferably to MVA viruses that do not replicate at all in the cells of the human and/or non-human primate vaccinated with said virus. However, also within the scope of the present application are those viruses that show a minor residual replication activity that is controlled by the immune system of the human and/or non-human primate to which the recombinant MVA virus is administered.

In one embodiment, the replication incompetent recombinant MVA viruses may be viruses that are capable of infecting cells of the human and/or non-human primate in which the virus is used as vaccine. Viruses that are "capable of infecting cells" are viruses that are capable of interacting with the host cells to such an extent that the virus, or at least the viral genome, becomes incorporated into the host cell. Although the viruses used according to the invention are capable of infecting cells of the vaccinated human and/or non human primate, they are not capable of being replicated to infectious progeny virus in the cells of the vaccinated human and/or non-human primate.

According to the invention, it is to be understood, that a virus that is capable of infecting cells of a first animal species, but is not capable of being replicated to infectious progeny virus in said cells, may behave differently in a second animal species. For example, MVA-BN and its derivatives (see below) are viruses that are capable of infecting cells of the human, but that are not capable of being replicated to infectious progeny virus in human cells. However, the same viruses are efficiently replicated in chickens; i.e., in chickens, MVA-BN is a virus that is both capable of infecting cells and capable of being replicated to infectious progeny virus in those cells.

A suitable test that allows one to predict whether a virus is capable or not capable of being replicated in humans is disclosed in WO 02/42480 (incorporated herein by reference) and uses the severely immune compromised AGR129 mice strain. Furthermore, instead of the AGR129 mice, any other mouse strain can be used that is incapable of producing mature B and T cells, and as such is severely immune compromised and highly susceptible to a replicating virus. The results obtained in this mouse model reportedly are indicative for humans and, thus, according to the present application, a virus that is replication incompetent in said mouse model is regarded as a virus that is "replication incompetent in humans."

In other embodiments, the viruses according to the invention are preferably capable of being replicated in at least one type of cells of at least one animal species. Thus, it is possible to amplify the virus prior to its administration to the animal that is to be vaccinated and/or treated. By way of example, reference is made to MVA-BN that can be amplified in CEF (chicken embryo fibroblasts) cells, but that is a virus that is not capable of being replicated to infectious progeny virus in humans.

In further embodiments, Modified Vaccinia virus Ankara (MVA) is suitable for use in humans and several animal species such as mice and non-human primates. MVA is known to be exceptionally safe. MVA has been generated by long-term serial passages of the Ankara strain of Vaccinia virus (CVA) on chicken embryo fibroblasts (for review see Mayr, A., Hochstein-Mintzel, V. and Stickl, H. Infection 3, 6-14 [1975]; Swiss Patent No. 568,392). Examples of MVA virus strains that have been deposited in compliance with the requirements of the Budapest Treaty, and that are useful for the generation of recombinant viruses according to the invention, are strains MVA 572 deposited at the European Collection of Animal Cell Cultures (ECACC), Salisbury (UK) with the deposition number ECACC 94012707 on Jan. 27, 1994; MVA 575 deposited under ECACC 00120707 on Dec. 7, 2000; and MVA-BN deposited with the number 00083008 at the ECACC on Aug. 30, 2000.

In one embodiment, the MVA strain used in generating a recombinant MVA is MVA-575, or a derivative thereof.

In a preferred embodiment, the MVA strain used in generating a recombinant MVA is MVA-572, or a derivative thereof.

In another preferred embodiment, the MVA strain used in generating a recombinant MVA is MVA-Vero, or a derivative thereof. MVA-Vero strains have been deposited at the European Collection of Animal Cell Cultures under the deposition numbers ECACC V99101431 and 01021411. The safety of the MVA-Vero is reflected by its biological, chemical and physical characteristics as described in the International Patent Application PCT/EP01/02703, incorporated herein by reference in its entirety. In comparison to other MVA strains, the Vero-MVA includes one additional genomic deletion.

In a more preferred embodiment, the MVA strain is MVA-BN, or a derivative thereof. MVA-BN has been deposited at the European Collection of Animal Cell Cultures with the deposition number ECACC V00083008. MVA-BN virus is an extremely attenuated virus also derived from Modified Vaccinia Ankara virus. A definition of MVA-BN and its derivatives is given in PCT/EP01/13628, incorporated herein by reference in its entirety.

The term "derivatives" of a virus according to the invention refers to progeny viruses showing the same characteristic features as the parent virus, but showing differences in one or more parts of its genome. The term "derivative of MVA" describes a virus which has the same functional characteristics compared to MVA. For example, a derivative of MVA-BN has the characteristic features of MVA-BN. One of these characteristics of MVA-BN, or of derivatives thereof, is its attenuation and lack of replication in human cell lines, such as the human keratinocyte cell line HaCaT, the human embryo kidney cell line 293, the human bone osteosarcoma cell line 143 B, and the human cervix adenocarcinoma cell line HeLa.

In a preferred embodiment, the virus according to the invention is a virus that has been produced and/or passaged under serum free conditions to reduce the risk of infections with agents contained in serum. One skilled in the art of the invention is familiar with methods for producing and/or passaging virus under serum free conditions.

In certain embodiments, recombinant MVA, or a derivative thereof, according to the invention, is administered in a concentration range of about $10^4$ to about $10^9$ TCID$_{50}$/ml, preferably in a concentration range of about $10^5$ to about $5 \times 10^8$ TCID$_{50}$/ml, most preferably in a concentration range of about $10^6$ to about $10^8$ TCID$_{50}$/ml.

The actual amount used depends on the type of virus and the animal species to be vaccinated. For MVA-BN, a typical vaccination dose for humans comprises about $5 \times 10^7$ TCID$_{50}$ to about $5 \times 10^8$ TCID$_{50}$, such as about $1 \times 10^8$ TCID$_{50}$, administered subcutaneously.

In one embodiment, an immune response is induced with a single administration of the recombinant poxvirus as defined above, in particular with an MVA strain, such as MVA-BN and its derivatives. Accordingly, one may use the MVA virus according to the invention, in particular an MVA strain, such as MVA-BN and its derivatives in homologous prime boost regimes. In these regimes, it is possible to use a recombinant poxvirus such as a recombinant MVA for a first vaccination, and to boost the immune response generated in the first vaccination by further administration of the same virus, or of a related recombinant MVA virus, than the one used in the first vaccination.

In another embodiment, the recombinant poxvirus according to the invention, in particular an MVA strain, such as MVA-BN and its derivatives, may also be used in heterologous prime-boost regimes; these regimes are those in which one or more of the vaccinations is done with a MVA virus as defined above, and one or more of the additional vaccinations is done with another type of vaccine, for example, another virus vaccine, a protein or a nucleic acid vaccine.

According to the invention, the mode of administration may be intravenously, intradermal, intranasal, or subcutaneously. A preferred embodiment is subcutaneous administration. However, any other mode of administration may be used such as, for example, scarification.

In one embodiment, the recombinant MVA according to the invention is useful as a medicament or vaccine.

According to a preferred embodiment, the recombinant MVA is used for the introduction of an exogenous coding sequence into a target cell, said sequence being either homologous or heterologous to the genome of the target cell.

In one embodiment, the introduction of an exogenous coding sequence into a target cell is done in vitro to produce proteins, polypeptides, peptides, antigens or antigenic epitopes.

In a preferred embodiment, the method of introduction of an exogenous coding sequence into a target cell in vitro to produce proteins, polypeptides, peptides, antigens or antigenic epitopes comprises the infection of a host cell with the recombinant MVA according to the invention; cultivation of the infected host cell under suitable conditions; and isolation and/or enrichment of the polypeptide, peptide, protein, antigen, epitope and/or virus produced by said host cell.

In a further embodiment, the method for introduction of exogenous sequences into cells is applied for in vitro and/or in vivo therapy.

In one embodiment, for in vitro therapy, isolated cells that have been previously (ex vivo) infected with the recombinant MVA according to the invention are administered to the living animal body for affecting, preferably for inducing, an immune response.

In another embodiment, for in vivo therapy, the recombinant MVA virus according to the invention is directly administered to the living animal body for affecting, preferably for inducing, an immune response.

In a preferred embodiment, the cells surrounding the site of inoculation, and also cells where the virus is transported to via, for example, the blood stream, are directly infected in vivo by the recombinant MVA according to the invention. After infection, these cells synthesize the proteins, peptides or antigenic epitopes of the therapeutic genes, which are encoded by the exogenous coding sequences, and subsequently, present them or parts thereof on the cellular surface. Subsequently, specialized cells of the immune system recognize the presentation of such heterologous proteins, peptides or epitopes and launch a specific immune response.

Since the MVA is highly growth-restricted and, thus, highly attenuated, it is useful for the treatment of a wide range of mammals including humans, and particularly immune-compromised animals or humans. Thus, in one embodiment, the invention also provides pharmaceutical compositions and vaccines for inducing an immune response in a living animal body, including a human.

In one embodiment, the pharmaceutical composition may generally include one or more pharmaceutical acceptable and/or approved carriers, additives, antibiotics, preservatives, adjuvants, diluents and/or stabilizers. Non-limiting examples of such auxiliary substances are water, saline, glycerol, ethanol, wetting or emulsifying agents, pH buffering substances, or the like. Suitable carriers are typically selected from the group comprising large, slowly metabolized molecules such as, for example, proteins, polysaccharides, polylactic acids, polyglycolitic acids, polymeric amino acids, amino acid copolymers, lipid aggregates, or the like.

In another embodiment, for the preparation of vaccines, the recombinant MVA virus according to the invention is converted into a physiologically acceptable form. This can be done based on the experience in the preparation of poxvirus vaccines used for vaccination against smallpox (as described by Stickl, H. et al. Dtsch. med. Wschr. 99, 2386-2392 [1974]). For example, the purified virus is stored at −80° C. with a titer of $5 \times 10^8$ $TCID_{50}$/ml formulated in 10 mM Tris, 140 mM NaCl pH 7.4.

In one embodiment, the MVA virus according to the invention is used for the preparation of vaccine shots. For example, about $10^2$ to about $10^8$ particles of the virus are lyophilized in 100 ml of phosphate-buffered saline (PBS) in the presence of 2% peptone and 1% human albumin in an ampoule, preferably a glass ampoule. In another non-limiting example, the vaccine shots are produced by stepwise freeze-drying of the virus in a formulation. In certain embodiments, this formulation can contain additional additives such as mannitol, dextran, sugar, glycine, lactose or polyvinylpyrrolidone or other aids, such as antioxidants or inert gas, stabilizers or recombinant proteins (for example, human serum albumin) suitable for in vivo administration. The glass ampoule is then sealed and can be stored between 4° C. and room temperature for several months. However, as long as no immediate need exists, the ampoule is stored preferably at temperatures below −20° C.

In a further embodiment, for vaccination or therapy, the lyophilisate can be dissolved in 0.1 to 0.5 ml of an aqueous solution, preferably physiological saline or Tris buffer, and administered either systemically or locally, i.e. parenterally, subcutaneously, intramuscularly, by scarification or any other path of administration know to the skilled practitioner. The mode of administration, the dose and the number of administrations can be optimized by those skilled in the art in a known manner. However, most commonly, a patient is vaccinated with a second shot about one month to six weeks after the first vaccination shot.

Sequences Derived from the MVA Genome

The invention further relates to plasmid vectors, which can be used to generate recombinant MVA according to the invention, and also relates to certain DNA sequences.

In one embodiment, the IGR located between two adjacent ORFs comprises nucleotide sequences, herein referred to as "IGR-DNA sequences", in which the exogenous DNA sequence of interest can be inserted.

Accordingly, in one embodiment, the plasmid vector according to the invention comprises a DNA sequence derived from, or homologous to, the genome of MVA, wherein said DNA sequence comprises a complete or partial fragment of an IGR-DNA sequence.

In a preferred embodiment, the plasmid vector further comprises, inserted into said IGR-derived sequence, at least one cloning site for (i) the insertion of an exogenous DNA sequence of interest and, preferably, for (ii) the insertion of a poxviral transcription control element operatively linked to said exogenous DNA sequence. Optionally, the plasmid vector further comprises a reporter- and/or selection-gene-cassette.

In a preferred embodiment, the plasmid vector further comprises sequences of the two adjacent ORFs flanking said complete or partial fragment of the IGR-DNA sequence.

In another embodiment, some IGRs have been identified, which do not include nucleotide sequences. As described above (see Definitions), these IGRs are insertion sites flanked by abuting ORFs. Thus, in this embodiment, the plasmid vector comprises DNA sequences of the "IGR flanking sequences", i.e., DNA sequences of the two adjacent ORFs.

In a preferred embodiment, the cloning site for the insertion of the exogenous DNA sequence is inserted into the IGR.

In some embodiments, the DNA of the IGR flanking sequences is used to direct the insertion of exogenous DNA sequences into the corresponding IGR in the MVA genome.

In a more preferred embodiment, such a plasmid vector may additionally include a complete or partial fragment of an IGR sequence which comprises the cloning site for the insertion of the heterologous DNA sequence and, optionally, of the reporter- and/or selection-gene-cassette.

In one embodiment, IGR-DNA sequences are preferably selected from IGRs selected from the group comprising: 001L-002L, 002L-003L, 005R-006R, 006L-007R, 007R-008L, 008L-009L, 017L-018L, 018L-019L, 019L-020L, 020L-021L, 023L-024L, 024L-025L, 025L-026L, 028R-029L, 030L-031L, 031L-032L, 032L-033L, 035L-036L, 036L-037L, 037L-038L, 039L-040L, 043L-044L, 044L-045L, 046L-047R, 049L-050L, 050L-051L, 051L-052R, 052L-053R, 053R-054R, 054R-055R, 055R-056L, 061L-062L, 064L-065L, 065L-066L, 066L-067L, 077L-078R, 078R-079R, 080R-081R, 081R-082L, 082L-083R, 085R-086R, 086L-087R, 088R-089L, 089L-090R, 092R-093L, 094L-095R, 096R-097R, 097R-098R, 101R-102R, 103R-104R, 105L-106R, 107R-108L, 108L-109L, 109L-110L, 110L-111L, 113L-114L, 114L-115L, 115L-116R, 117L-118L, 118L-119R, 122R-123L, 123L-124L, 124L-125L, 125L-126L, 133R-134R, 134R-135R, 136L-137L, 137L-138L, 141L-142R, 143R-144R, 144R-145R, 145R-146R, 146R-147R, 147R-148R, 148R-149L, 152R-153L, 153L-154R, 154R-155R, 156R-157L, 157L-158R, 159R-160L, 160L-161R, 162R-163R, 163R-164R, 164R-165R, 165R-166R, 166R-167R, 167R-168R, 170R-171R, 173R-174R, 175R-176R, 176R-177R, 178R-179R, 179R-180R, 180R-181R, 183R-184R, 184R-185L, 185R-186R, 186R-187R, 187R-188R, 188R-189R, 189R-190R, 192R-193R.

In another embodiment, IGR flanking sequences of the two adjacent ORFs are preferably selected from ORFs selected from the group comprising: 001L-002L, 002L-003L, 005R-006R, 006L-007R, 007R-008L, 008L-009L, 017L-018L, 018L-019L, 019L-020L, 020L-021L, 023L-024L, 024L-025L, 025L-026L, 028R-029L, 030L-031L, 031L-032L, 032L-033L, 035L-036L, 036L-037L, 037L-038L, 039L-040L, 043L-044L, 044L-045L, 046L-047R, 049L-050L, 050L-051L, 051L-052R, 052R-053R, 053R-054R, 054R-055R, 055R-056L, 061L-062L, 064L-065L, 065L-066L, 066L-067L, 077L-078R, 078R-079R, 080R-081R, 081R-082L, 082L-083R, 085R-086R, 086L-087R, 088R-089L, 089L-090R, 092R-093L, 094L-095R, 096R-097R, 097R-098R, 101R-102R, 103R-104R, 105L-106R, 107R-108L, 108L-109L, 109L-110L, 110L-111L, 113L-114L, 114L-115L, 115L-116R, 117L-118L, 118L-119R, 122R-123L, 123L-124L, 124L-125L, 125L-126L, 133R-134R, 134R-135R, 136L-137L, 137L-138L, 141L-142R, 143L-144R, 144R-145R, 145R-146R, 146R-147R, 147R-148R, 148R-149L, 152R-153L, 153L-154R, 154R-155R, 156R-157L, 157L-158R, 159R-160L, 160L-161R, 162R-163R, 163R-164R, 164R-165R, 165R-166R, 166R-167R, 167R-168R, 170R-171R, 173R-174R, 175R-176R, 176R-177R, 178R-179R, 179R-180R, 180R-181R, 183R-184R, 184R-185L, 185R-186R, 186R-187R, 187R-188R, 188R-189R, 189R-190R, 192R-193R.

In a preferred embodiment, IGR-DNA sequences, as well as IGR flanking sequences, are selected from IGRs and ORFs, respectively, selected from the group comprising 007R-008L, 018L-019L, 044L-045L, 064L-065L, 136L-137L, 148L-149L.

In another preferred embodiment, IGR-DNA sequences are selected from the group comprising the nucleotide sequences:
no. 527-608 of SEQ ID NO: 32;
no. 299-883 of SEQ ID NO: 33;
no. 339-852 of SEQ ID NO: 34;
no. 376-647 of SEQ ID NO: 35;
no. 597-855 of SEQ ID NO: 36;
no. 400-607 of SEQ ID NO: 37.

In another preferred embodiment, IGR flanking sequences are selected from the group comprising the nucleotide sequences:
no.1-525 and 609-1190 of SEQ ID NO: 32;
no.101-298 and 884-1198 of SEQ ID NO: 33;
no.1-338 and 853-1200 of SEQ ID NO: 34;
no.1-375 and 648-1200 of SEQ ID NO: 35;
no.1-596 and 856-1200 of SEQ ID NO: 36;
no.1-399 and 608-1081 of SEQ ID NO: 37.

In yet another preferred embodiment, the DNA sequences are preferably derived from, or are homologous to, sequences of the genome of the MVA as deposited at ECACC under deposition number V00083008.

In yet another embodiment, the DNA sequences according to the invention are used to (i) identify or isolate the MVA or its derivatives according to the invention, and/or (ii) identify cells or individuals infected with an MVA according to the invention.

In another embodiment, the DNA sequences according to the invention are used to generate PCR-primers and/or hybridization probes.

In yet another embodiment, the DNA sequences according to the invention are used in array technologies.

Generation of Recombinant MVA

Methods suitable to generate a plasmid vector according to the invention are familiar to those skilled in the art of the invention. For example, to generate a plasmid vector with the sequences of the invention, the sequences can be isolated and cloned into a standard cloning vector, such as pBluescript (Stratagene), wherein they flank the exogenous DNA to be inserted into the MVA genome. Optionally, such a plasmid vector comprises a selection- or reporter-gene cassette, which can be deleted from the final recombinant virus, due to a repetitive sequence included into said cassette.

Methods to introduce exogenous DNA sequences by a plasmid vector into an MVA genome and methods to obtain recombinant MVA are well known to the person skilled in the art and, additionally, can be deduced from the following references:

(i) Molecular Cloning, A Laboratory Manual, Second Edition, by J. Sambrook, E. F. Fritsch and T. Maniatis. Cold Spring Harbor Laboratory Press, 1989: describes techniques and know how for standard molecular biology techniques such cloning of DNA, RNA isolation, western blot analysis, RT-PCR and PCR amplification techniques;

(ii) Virology Methods Manual, edited by Brian W. J. Mahy and Hillar O. Kangro, Academic Press, 1996: describes techniques for the handling and manipulation of viruses;

(iii) Molecular Virology: A Practical Approach, edited by A J Davison and R M Elliott, The Practical Approach Series, IRL Press at Oxford University Press, Oxford 199, Chapter 9, Expression of genes by Vaccinia virus vectors; and (iv) Current Protocols in Molecular Biology, Publisher: John Wiley and Son Inc., 1998, Chapter 16, section IV: Expression of proteins in mammalian cells using Vaccinia viral vector: describes techniques and know-how for the handling, manipulation and genetic engineering of MVA.

In one embodiment, the MVA and derivatives thereof, according to the invention, preferably the MVA deposited at ECACC under deposition number V00083008, is produced by transfecting a cell with a plasmid vector according to the invention, infecting the transfected cell with an MVA and, subsequently, identifying, isolating and, optionally, purifiying the MVA according to the invention.

Exogenous Sequences for Integration into Novel IGRs

Heterologous or exogenous DNA sequences are terms that are used interchangeably herein and refer to sequences which, in nature, are not normally found associated with the poxvirus as used according to the invention.

Thus, according to a further embodiment of the invention, the exogenous DNA sequence comprises at least one coding sequence. The coding sequence is operatively linked to a transcription control element, preferably to a poxviral transcription control element. In another embodiment, further combinations between poxviral transcription control element and, for example, internal ribosomal entry sites are used (for exemplary details, see FIGS. 1-14 and Examples 1-6).

According to another embodiment, the exogenous DNA sequence can comprise two or more coding sequences linked to one or several transcription control elements. Preferably, the coding sequence encodes one or more proteins selected from the group comprising polypeptides, peptides, foreign antigens or antigenic epitopes, especially those of therapeutically interesting genes.

"Therapeutically interesting genes" according to the invention can be genes derived from, or homologous to, genes of pathogenous or infectious microorganisms, which are disease-causing. Accordingly, in the context of the invention, such therapeutically interesting genes are presented to the immune system of an organism in order to affect, or more preferably to induce, a specific immune response and, thereby, vaccinate or prophylactically protect the organism against an infection with the microorganism.

In one embodiment, therapeutically interesting genes according to the invention comprise disease related genes, which have a therapeutic effect on proliferative disorders, cancer, or metabolic diseases. For example, a therapeutically interesting gene regarding cancer could be a cancer antigen that has the capacity to induce a specific anti-cancer immune reaction.

In a further preferred embodiment of the invention, the therapeutically interesting genes are selected from genes of infectious viruses, such as, for example, Dengue virus, Japanese encephalitis virus, Hepatitis virus B or C, or immunodeficiency viruses, such as HIV.

In one embodiment, genes derived from Dengue virus are preferably NS1 and PrM genes, wherein the genes can be derived from one, two, three or from all of the four reported Dengue virus serotypes. The NS1 gene is preferably derived from Dengue virus serotype 2 and is preferably inserted into the IGR between the ORFs 064L-065L (I4L-I5L). PrM genes, preferably derived from all of the four Dengue virus serotypes, are preferably inserted into the IGRs between the ORFs selected from 007R-008L, 044L-045L, 136L-137L, 148R-149L. More preferably, the PrM gene derived from Dengue virus serotype 1 (prM 1) is inserted into IGR 148R-149L, PrM 2 into IGR 007R-008L, PrM 3 into IGR 044L-045L, and PrM 4 into IGR 136L-137L.

According to a further embodiment of the invention, the exogenous DNA sequence comprises a coding sequence, which comprises at least one marker or selection gene.

"Marker gene" or genes, induce a color reaction in transduced cells, which can be used to identify transduced cells. The skilled practitioner is familiar with a variety of marker genes, which can be used in a poxviral system. Among these are the genes encoding, for example, β-Galactosidase (β-gal), β-Glucosidase (β-glu), Enhanced Green Fluorescence protein (EGFP), or Blue Fluorescence Protein (BFP or hbfp).

"Selection gene" or genes, transduce a particular resistance to a cell, whereby a certain method for selecting such cell becomes possible. The skilled practitioner is familiar with a variety of selection genes, which can be used in a poxviral system. Among these are, for example, Neomycin resistance gene (NPT) or Phosphoribosyl transferase gene (gpt).

According to a further embodiment of the invention, the exogenous DNA sequence comprises a spacer or spacing sequence, which separates poxviral transcription control element and/or coding sequence in the exogenous DNA sequence from the stop codon and/or the start codon of the adjacent ORFs.

According to the invention, this spacer or spacing sequence, located between the stop/start codon of the adjacent ORF and the coding sequence inserted in the exogenous DNA, has the advantage of stabilizing the inserted exogenous DNA and, thus, any resulting recombinant virus. The size of a suitable spacer sequence is variable, as long as the sequence is without its own coding or regulatory function.

According to a further embodiment, the spacer sequence, separating the poxviral transcription control element and/or the coding sequence in the exogenous DNA sequence from the stop codon of the adjacent ORF, is at least one nucleotide long.

According to yet another embodiment, the spacing sequence, separating the poxviral transcription control element and/or the coding sequence in the exogenous DNA sequence from the start codon of the adjacent ORF, is at least 30 nucleotides.

In one embodiment, if a typical Vaccinia virus promoter element is upstream of a start codon, the insertion of exogenous DNA might separate the promoter element from the start codon of the adjacent ORF. A spacing sequence of about 30 nucleotides is the preferred distance to secure that, a poxviral promoter located upstream of the start codon of the ORF, is not influenced.

Additionally, according to a further preferred embodiment, the distance between the inserted exogenous DNA and the start codon of the adjacent ORF comprises about 50 nucleotides, and more preferably about 100 nucleotides.

"A typical Vaccinia promoter" element can be identified by scanning for, for example, the sequence "TAAAT" for late promoters (Davison & Moss, J. Mol. Biol. 210: 771-784 [1989]), and for an A/T rich domain for early promoters.

According to a further preferred embodiment, the spacing sequence comprises an additional poxviral transcription control element, which is capable of controlling the transcription of the adjacent ORF.

Recombinant MVA Viruses Expressing HIV Peptides Inserted into IGRs

In a preferred embodiment, the invention relates to recombinant MVA viruses comprising one or a plurality of exogenous sequences in the viral genome, selected from a group consisting of expression cassettes comprising one or more HIV proteins; expression cassettes comprising one or more parts of HIV proteins; and expression cassettes comprising one or more derivatives of HIV proteins.

According to one embodiment, the exogenous sequences comprise HIV peptides selected from a group consisting of the full-length proteins Gag (capsid protein), Pol (polymerase protein), Env (envelope protein), Tat, Vif, Vpu, Vpr, Rev and Nef; and parts or derivatives thereof.

For example, according to one embodiment, the exogenous DNA sequence is derived from HIV and encodes HIV env, wherein the HIV env gene is preferably inserted into the IGR 007R-008L.

In certain embodiments, the recombinant MVA virus, in particular MVA-BN and its derivatives, comprises regulatory/accessory proteins of HIV. The protein can exhibit full biological activity.

The regulatory/accessory proteins of HIV proteins have a biological activity that can have undesired side effects. Thus, it is also within the scope of the invention that, in certain other embodiments, one or more HIV proteins expressed from the recombinant MVA virus has a reduced biological activity compared to the wild-type protein, and thus is said to have reduced activity.

One skilled in the art is familiar with tests suitable to determine whether an HIV protein has reduced activity.

The molecular mechanism of the Vif protein, which is essential for viral replication in vivo, remains unknown, but Vif possesses a strong tendency toward self association. This multimerization was shown to be important for Vif function in viral life cycle (Yang S. et al., J Biol Chem 276: 4889-4893 [2001]). Additionally, vif was shown to be specifically associated with the viral nucleoprotein complex, and this might be functionally significant (Khan M. A. et al., J Virol. 75 (16): 7252-65 [2001]).

Thus, in a preferred embodiment, the exogenous sequence expresses a vif with reduced activity, and the vif shows a reduced multimerization and/or association to the nucleoprotein complex.

The Vpr protein plays an important role in the viral life cycle. Vpr regulates the nuclear import of the viral pre-integration complex and facilitates infection of non dividing cells such as macrophages (Agostini et al., AIDS Res Hum Retroviruses 18(4):283-8 [2002]). Additionally, it has transactivating activity mediated by interaction with the LTR (Vanitharani R. et al., Virology 289 (2):334-42 [2001]).

Thus, in a preferred embodiment, the exogenous sequence expresses a vpr with reduced activity, and said vpr shows either decreased or no transactivation and/or interaction, with the viral preintegration complex.

Vpx, which is highly homologous to Vpr, is also critical for efficient viral replication in non-dividing cells. Vpx is packaged in virus particles via an interaction with the p6 domain of the gag precursor polyprotein. Like Vpr, Vpx is involved in the transportation of the preintegration complex into the nucleus (Mahalingam et al., J. Virol. 75 (1):362-74 [2001]).

Thus, in a preferred embodiment, the exogenous sequence expresses a Vpx with reduced activity, and the Vpx has a decreased ability to associate to the preintegration complex via the gag precursor.

The Vpu protein is known to interact with the cytoplasmic tail of the CD4 and causes CD4 degradation (Bour et al., Virology 69 (3):1510-20 [1995]).

Therefore, in a preferred embodiment, the exogenous sequence expresses a Vpu with reduced activity, and the Vpu has a reduced ability to trigger CD4 degradation.

The relevant biological activity of the well-characterized Tat protein is the transactivation of transcription via interaction with the transactivation response element (TAR). It was demonstrated that Tat is able to transactivate heterologous promoters lacking HIV sequences other than TAR (Han P. et al., Nucleic Acid Res 19 (25):7225-9 [1991]).

Thus, in a preferred embodiment, the exogenous sequence expresses a tat with reduced activity, and the tat shows reduced transactivation of promoters via the TAR element.

In another preferred embodiment, the exogenous sequence expresses a transdominant Tat, and the transdominant Tat can be obtained by making the following substitutions: 22 (Cys>Gly) and 37 (Cys>Ser).

Nef protein is essential for viral replication responsible for disease progression by inducing the cell surface downregulation of CD4 (Lou T et al., J Biomed Sci 4(4):132 [1997]). This downregulation is initiated by direct interaction between CD4 and Nef (Preusser A. et al., Biochem Biophys Res Commun 292 (3):734-40 [2002]). Thus, Nef protein with reduced function shows reduced interaction with CD4.

Thus, in preferred embodiments, the exogenous sequence expresses a Nef with reduced activity, and the Nef is truncated at the amino terminus such as, for example, a Nef in which the 19 N-terminal amino acids are deleted.

The relevant function of Rev is the posttranscriptional transactivation initiated by interaction with the Rev-response element (RRE) of viral RNA (Iwai et al., Nucleic Acids Res 20 (24):6465-72 [1992]).

Thus, in a preferred embodiment, the exogenous sequence expresses a Rev with reduced activity, and the Rev shows a reduced interaction with the RRE.

In certain embodiments, the accessory/regulatory proteins are expressed individually.

In other embodiments, multiple polypeptides are expressed and some or all of the polypeptides are expressed as fusion proteins. In this context reference is made to WO 03/097675, the content of which is herewith incorporated by reference.

In a preferred embodiment, the recombinant MVA virus according to the invention, such as MVA-BN and its derivatives, expresses a fusion protein comprising at least four HIV polypeptides selected from the group consisting of the full-length proteins Vif, Vpr, Vpu, Vpx, Rev, Tat and Nef; and derivatives or parts thereof.

In another embodiment, the recombinant MVA virus according to the invention, such as MVA-BN and its derivatives, expresses at least eight HIV polypeptides selected from the group consisting of the full-length Vif, Vpr, Vpu, Rev, Tat, Nef, Gag and Pol; and derivatives or parts thereof.

In another embodiment, a recombinant MVA virus according to the invention, such as MVA-BN and its derivatives, expresses one or more polypeptides selected from the group consisting of:

(i) a fusion protein comprising Vif-Vpu-Vpr-Rev, ligated in this order, or in a different order, wherein Vif, Vpu, Vpr and Rev stand for full-length proteins, or parts or derivatives of the full-length proteins;

(ii) a Nef, or a part or derivative thereof, in particular a Nef protein in which N-terminal amino acids are deleted, such as the first 19 amino acids;

(iii) a Tat, or a part or derivative thereof, in particular a transdominant Tat; and (iv) a Gag-Pol fusion protein, wherein Gag and Pol stand for full-length proteins, or parts or derivatives of the full-length proteins.

The number of expression cassettes from which the HIV polypeptides are expressed is not critical. In one embodiment, the HIV polypeptides are expressed from two to five expression cassettes comprising a plurality of the following:

(i) an expression cassette expressing a Vif-Vpu-Vpr-Rev fusion protein, wherein Vif, Vpu, Vpr and Rev stand for either full-length proteins, or parts or derivatives of the full-length proteins; arranged in the exemplified order, or in a different order;
(ii) an expression cassette expressing Nef or a part or derivative thereof, in particular a Nef protein in which N-terminal amino acids are deleted, such as a Nef lacking the first 19 amino acids;
(iii) an expression cassette expressing Tat or a part or derivative thereof, in particular a transdominant Tat; and
(iv) an expression cassette expressing a Gag-Pol fusion protein, wherein Gag and Pol stand for either full-length proteins or parts or derivatives of the full-length proteins; arranged in the exemplified order, or in the reverse order (i.e., Pol-Gag).

In a preferred embodiment, the expression of heterologous nucleic acid sequence is preferably, but not exclusively, under the transcriptional control of a poxvirus promoter. An example of a suitable poxvirus promoter is the cowpox ATI promoter (see WO 03/097844, incorporated herein by reference). In certain embodiments, the expression of each expression cassette is controlled by a different promoter. In other embodiments, all expression cassettes are controlled by a copy of the same promoter.

In one embodiment, the invention relates to a recombinant virus in which all HIV expression cassettes, such as the four expression cassettes exemplified above, are controlled by a cowpox ATI promoter or a derivative thereof, as defined in WO 03/097844.

In one embodiment, the expression cassettes can be inserted into 1 to 10 insertion sites in the genome of a recombinant MVA according to the invention, such as MVA-BN and its derivatives.

It was found that recombinant MVA viruses, in particular MVA-BN and its derivatives, used for the expression of at least six HIV proteins, or six parts or derivatives thereof, can be easily obtained if not all expression cassettes are inserted into the same insertion side.

Thus, in certain embodiment, the different expression cassettes are inserted into 2 to 8, or 3 to 5, or into 3 insertion sites in the MVA genome.

The insertion of heterologous nucleic acid sequence can be done into a non-essential region of the virus genome. According to one embodiment, the heterologous nucleic acid sequence is inserted at a naturally occurring deletion site of the MVA genome (disclosed in PCT/EP96/02926, incorporated herein by reference).

According to a further embodiment, one or more heterologous sequences can be inserted into one or more intergenic regions of the MVA genome as described herein.

Methods on how to insert heterologous sequences into the poxviral genome are known to a person skilled in the art.

In a preferred embodiment, the expression cassettes comprising one or more HIV proteins, parts or derivatives thereof, can be inserted into one or more intergenic regions selected from the group consisting of IGR 07-08, IGR I4L-I5L, and IGR 136-137 of the MVA genome, in particular the genome of MVA-BN and its derivatives.

In another embodiment, the recombinant poxvirus is MVA-BN, or a derivative thereof, comprising all the following expression cassettes inserted into the specified insertion sites:

(i) an expression cassette expressing Vif-Vpu-Vpr-Rev as fusion protein in this or a different order, wherein Vif, Vpu, Vpr and Rev stand for either full-length proteins, or parts or derivatives of the full-length proteins; inserted into the intergenic region IGR 07-08;

(ii) a second expression cassette expressing Nef, or a part or derivative thereof, in particular a Nef protein in which N-terminal amino acids are deleted, such as Nef lacking the first 19 amino acids; inserted into-IGR I4L-I5L;

(iii) a third expression cassette that expresses Tat, or a part or derivative thereof, in particular a transdominant Tat, inserted into IGR 136-137; and (iv) a fourth expression cassette that express a Gag-Pol fusion protein, wherein Gag and Pol stand for either full-length proteins or parts or derivatives of the full-length proteins; inserted into IGR 136-137.

Thus, in the latter embodiment, the third and the fourth expression cassettes are inserted into the same integration site. It is to be taken into account that IGR I4L-I5L on the one side, and IGR 136-137 and IGR 07-08 on the other side, belong to two different numbering systems; these numbering or nomenclature systems are explained above.

In a preferred embodiment, the recombinant virus according to the invention can induce a protective immune response. The term "protective immune response" as used herein is intended to mean that the vaccinated subject is able to control in some way an infection with the pathogenic agent against which the vaccination was done. Usually, the animal or subject having developed a "protective immune response" develops milder clinical symptoms than an unvaccinated subject, and/or the progression of the disease is slowed down.

The invention further relates to medicaments and vaccines comprising the recombinant MVA virus of the invention.

In other embodiments, the invention further relates to pharmaceutical compositions and vaccines comprising a recombinant MVA virus as defined above.

In further embodiments, the invention further relates to the use of a recombinant MVA virus as defined above for the preparation of a medicament and/or vaccine for the treatment and/or prevention of AIDS.

In another embodiment, the invention further relates to a method of prevention AIDS comprising the step of administration of a MVA virus as defined above.

It is pointed out that the term "prevention of AIDS" as used in the context of the invention does not mean that the recombinant MVA virus prevents AIDS in all subjects under all conditions. To the contrary, this term as used herein refers to any statistically significant protective effect, even if this effect is considered low.

Possible concentrations and modes of administration are indicated above.

Numerous ways to prepare recombinant MVA formulations are known to the skilled artisan, as are modes of storage. In this context, reference is made to WO 03053463, incorporated herein by reference.

In a further embodiment, the invention relates to a host cell infected with a recombinant MVA virus as defined above. The host cell can be a cell that is not part of an entire living organism.

In another embodiment, the invention further relates to the genome of a recombinant MVA virus according to the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the appended claims.

EXAMPLES

The following examples will further illustrate the invention. It will be understood by any person skilled in the art that the provided examples in no way are to be interpreted in a way that limits the invention to these examples. The scope of the invention is only to be limited by the full scope of the appended claims.

Example 1

Insertion Vectors pBNX39, pBNX70 and pBN84

Figure 1A:
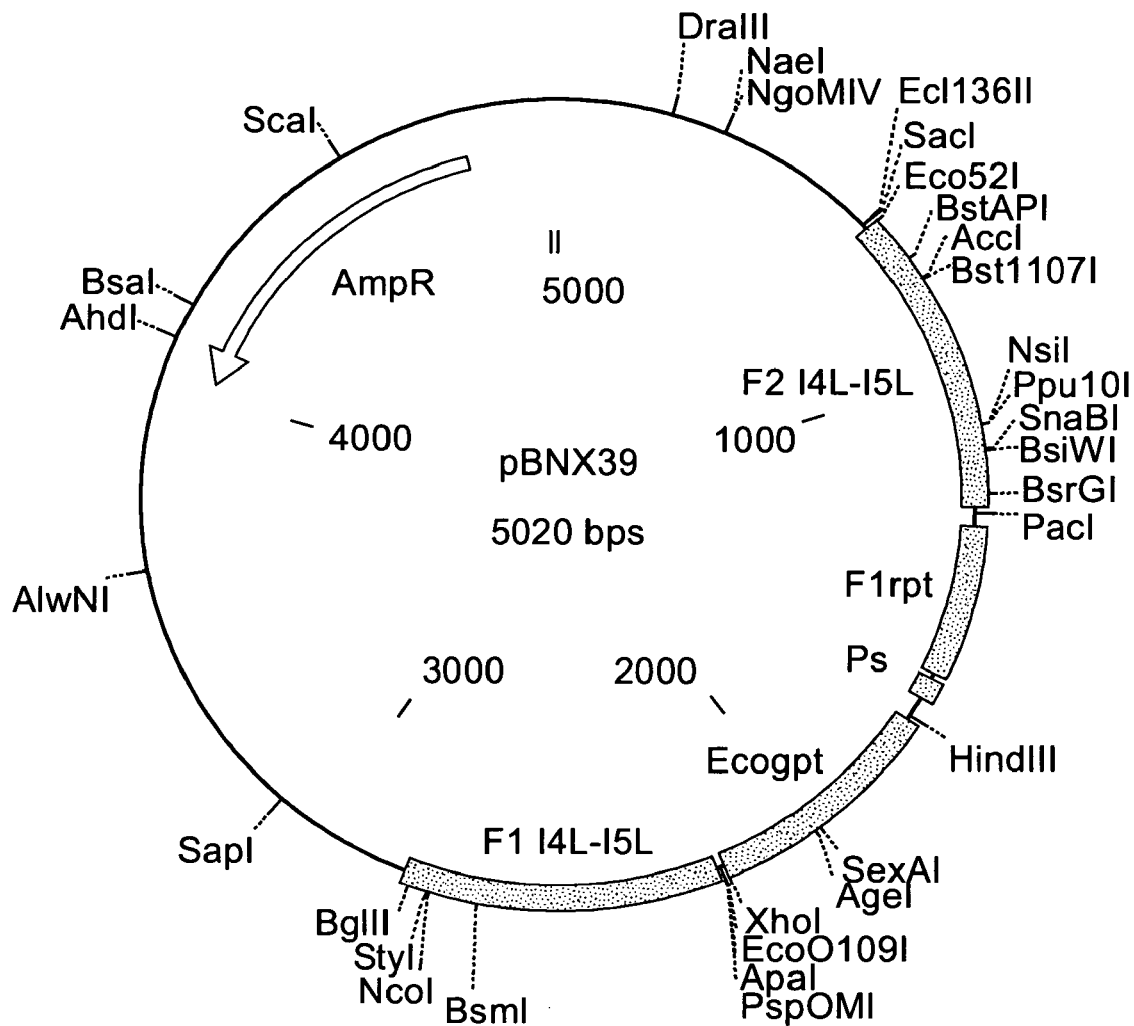
Figure 1B:
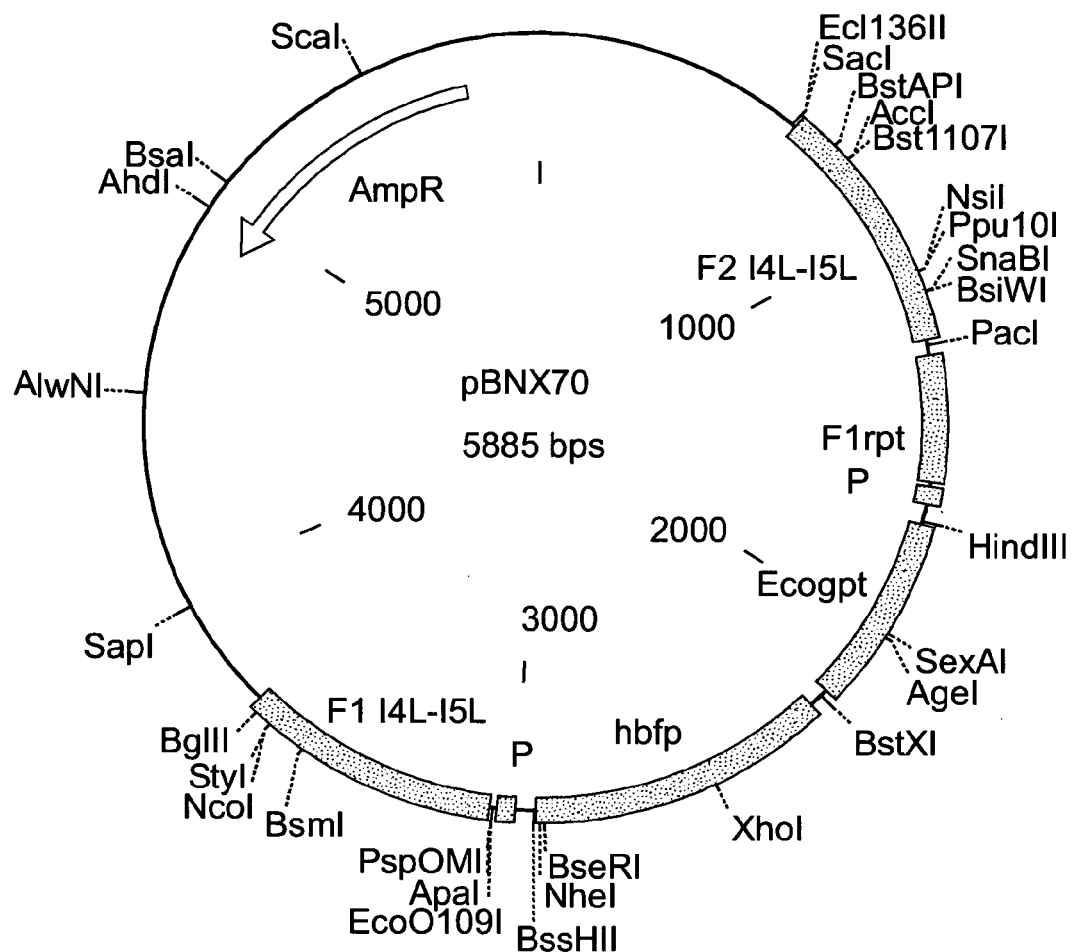
Figure 1C:
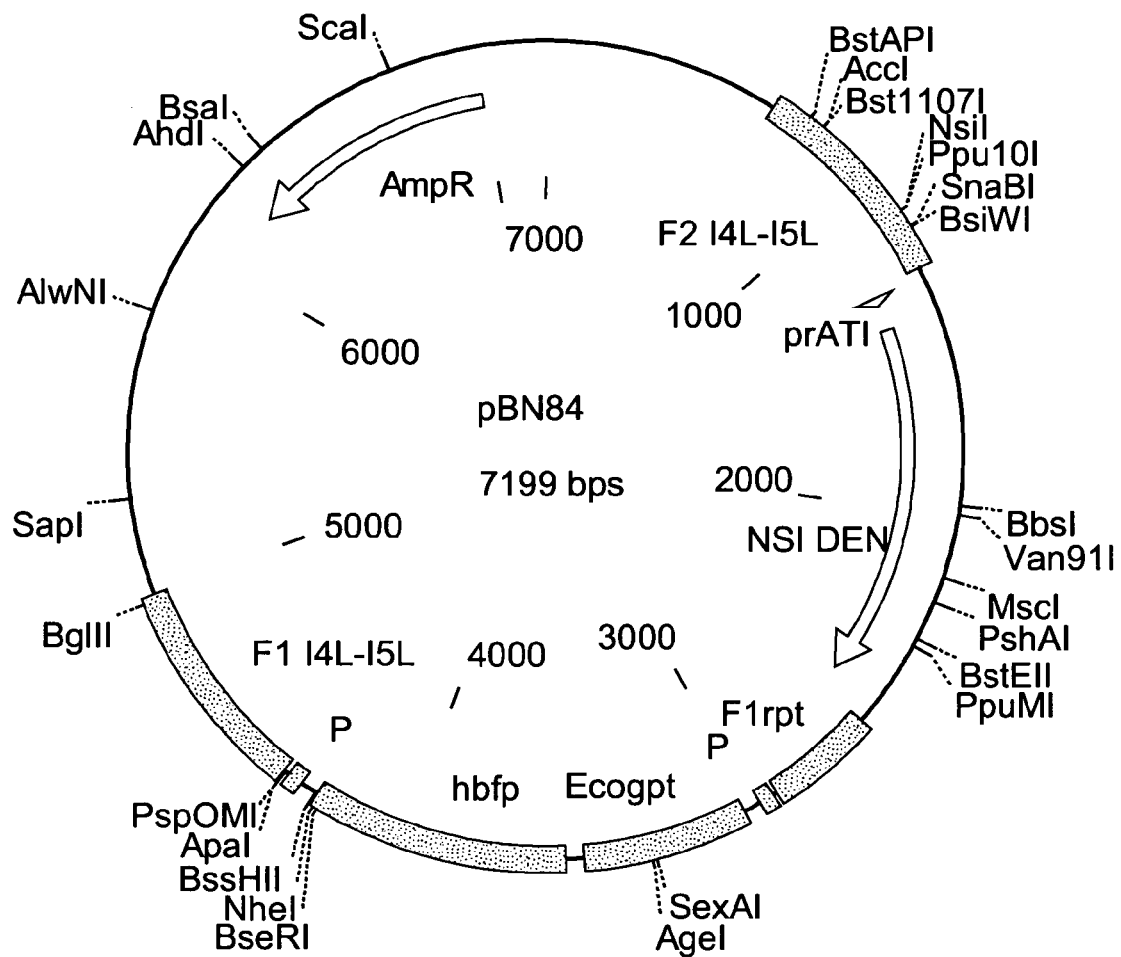

For the insertion of exogenous sequences into the intergenic region adjacent to the 065L ORF (insertion site is at genome position 56760) of MVA, a vector was constructed which comprises about 1200 bp of the flanking sequences adjacent to the insertion site. These flanking sequence are separated into two flanks comprising, on one flank about 610 bp of the 065L ORF (alternative nomenclature: I4L ORF), and on the other flank about 580 bp of the intergenic region be Hind the 065L ORF, as well as parts of the proximate ORF. In between these flanking sequences, there is an Ecogpt gene (gpt stands for phosphoribosyltransferase gene isolated from *E. Coli*) and a BFP (blue fluorescence protein), respectively, under the transcriptional control of a poxviral promoter. Additionally, there is at least one cloning site for the insertion of additional genes or sequences to be inserted into the intergenic region be Hind the I4L ORF. Exemplary vector constructs according to the invention are disclosed in FIGS. 1A and 1B (pBNX39, pBNX70). In vector pBN84 (FIG. 1C) the coding region for Dengue virus NS1 is inserted in the cloning site of pBNX70 (FIG. 1B).

Generation of the Recombinant MVA Via Homologous Recombination

Foreign genes can be inserted into the MVA genome by homologous recombination. For that purpose the foreign gene of interest is cloned into a plasmid vector, as described above. This vector is transfected in MVA infected cells. The recombination takes place in the cytoplasm of the infected and transfected cells. With help of the selection and/or reporter cassette, which is also contained in the insertion vector, cells comprising recombinant viruses are identified and isolated.

For homologous recombination BHK (Baby hamster kidney) cells or CEF (primary chicken embryo fibroblasts) are seeded in 6 well plates using DMEM (Dulbecco's Modified Eagles Medium, Gibco BRL) containing 10% fetal calf serum (FCS), or VP-SFM (Gibco BRL) containing 4 mmol/l L-Glutamine for a serum free production process.

Cells need to be still in the growing phase and therefore should reach 60-80% confluence on the day of transfection. Cells are counted before seeding, as the number of cells has to be known for determination of the multiplicity of infection (moi) for infection.

For the infection, the MVA stock is diluted in DMEM/FCS or VP-SFM/L-Glutamine so that 500 µl dilution contain an appropriate amount of virus that will give a moi of about 0.1-1.0. Cells are assumed to have divided once after seeding. The medium is removed from cells and cells are infected with 500 µl of diluted virus for 1 hour rocking at room temperature. The inoculum is removed and cells are washed with DMEMNP-SFM. Infected cells are left in 1.6 ml DMEM/FCS or VP-SFM/L-Glutamine, respectively, while setting up the transfection reaction (Qiagen Effectene Kit).

For the transfection, the "Effectene" transfection kit (Qiagen) is used. A transfection mix is prepared of 1-2 µg of linearized insertion vector (total amount for multiple transfection) with buffer EC to give a final volume of 100 µl. Then, 3.2 µl of Enhancer are added, the mixture vortexed and incubated at room temperature for 5 min. Then, 10 µl of Effectene are added after vortexing the stock tube, the solution is mixed thoroughly by vortexing, and incubated at room temperature for 10 min. Next, 600 µl of DMEM/FCS or VP-SFM/L-Glutamine, respectively, are added, mixed and subsequently, the whole transfection mix is added to the cells, which are already covered with medium. The dish is rocked gently to mix the transfection reaction. The incubation takes place at 37° C. with 5% $CO_2$ overnight. The next day, the medium is removed and replaced with fresh DMEM/FCS or VP-SFM/L-Glutamine. Incubation is continued until day 3.

For harvesting, the cells are scraped into medium, and then the cell suspension is transferred to an adequate tube and frozen at –20° C. for short-term storage, or at –80° C. for long-term storage.

Insertion of Ecogpt in the I4L Insertion Site of MVA

In a first round, cells were infected with MVA according to the above-described protocol and were additionally transfected with insertion vector pBNX39 (FIG. 1A) containing the Ecogpt gene (Ecogpt, or shortened to gpt, stands for phosphoribosyltransferase gene) as a reporter gene. Resulting recombinant viruses were purified by 3 rounds of plaque purification under phosphribosyl-transferase metabolism selection by addition of mycophenolic acid, xanthin, and hypoxanthin. Mycophenolic acid (MPA) inhibits inosine monophosphate dehydrogenase, and results in blockage of purine synthesis and inhibition of viral replication in most cell lines. This blockage can be overcome by expressing Ecogpt from a constitutive promoter and providing the substrates xanthine and hypoxanthine.

Resulting recombinant viruses were identified by standard PCR assays using a primer pair selectively amplifying the expected insertion site. To amplify the I4L insertion side, the primer pair comprising BN499 (CAA CTC TCT TCT TGA TTA CC, SEQ ID NO.:1) and BN500 (CGA TCA AAG TCA ATC TAT G, SEQ ID NO.:2) was used. When the DNA of the empty vector virus MVA is amplified, the expected PCR fragment is 328 nucleotides (nt) long. However, when a recombinant MVA is amplified, which has incorporated exogenous DNA at the I4L insertion site, the fragment is correspondingly enlarged.

Insertion of NS1 in the IGR064L-065L (I4L-I5L) Insertion Site of MVA

In a first round, cells were infected with MVA according to the above-described protocol, and were additionally transfected with insertion vector pBN84 (FIG. 1C) containing the Ecogpt gene for selection and BFP (Blue fluorescence protein) as a reporter gene. Resulting recombinant viruses were purified by 7 rounds of plaque purification under phosphribosyl-transferase metabolism selection by addition of mycophenolc acid, xanthin and hypoxanthin.

Resulting recombinant viruses were identified by standard PCR assays, using a primer pair selectively amplifying the expected insertion site. To amplify the I4L-I5L insertion site, the primer pair comprising BN499 (CAA CTC TCT TCT TGA TTA CC, SEQ ID NO.:1) and BN500 (CGA TCA AAG TCA ATC TAT G, SEQ ID NO.:2) were used. When the DNA of the empty vector virus MVA is amplified, the expected PCR fragment is 328 nucleotides (nt) long. When a recombinant MVA for NS1 is amplified, which has incorporated Dengue virus NS1 coding region at the I4L insertion site, the PCR fragment is expected to be 1683 bp. The PCR results in FIG.

7 show clearly the stable insertion of NS1 in the I4L insertion site after 17 rounds of virus amplification.

Testing of recMVA Including NS1 (MVA-BN22) In Vitro

T25 flasks with about 80% confluent monolayers of BHK cells were inoculated with 100 μl of the virus stock diluted to 1×10⁷ in MEMα containing 1% FCS, and rocked at room temperature for 30 minutes. 5 ml of MEMα containing 3% FCS were added to each flask and incubated at 30° C. in a CO₂ incubator. The flasks were harvested after 48 hours. The supernatant was removed from each flask, and spun at 260×g for 10 minutes at 4° C. The resulting supernatants were stored in aliquots at −80° C. The pellets were each washed with 5 ml of 1×PBS twice and then resuspended in 1 ml of hypotonic douncing buffer containing 1% Triton X100. The cell lysates were harvested and spun for 5 minutes at 16,000×g, and the resulting supernatants were stored in microcentrifuge tubes at −80° C.

Flasks inoculated with MVA including GFP, MVA including the NS1 gene inserted in a deletion site (MVA-BN07), and mock infected flasks were also treated the same way as described above.

The cell/viral lysate and the supernatant were treated in non-reducing/reducing sample buffer under non-heated/heated conditions, respectively. The proteins were separated by 10% SDS PAGE and transferred to nitrocellulose membranes. The blots were probed overnight with pooled convalescent patients' sera (PPCS) at 1:500 dilution. After washing 3 times with 1× PBS, the blots were incubated with anti-human IgG-HRP (DAKO) for 2 hours at room temperature. After the blots were washed as described before, the color was developed using 4 chloro-1-naphtol.

The western blot results showed that NS1 in MVA-BN22 is expressed in large quantities. NS1 was expressed in the right conformation, i.e., as a dimer under non-heated/non-reducing conditions, and as a monomer under heated/reducing conditions.

The NS1 expression was compared in both MVA-BN22 and MVA-BN07. The BHK cells were inoculated with the same pfu and harvested after 48 hours. The results showed that the expression of NS1 was much higher in BN22 than in BN07. The western blots results also showed that there is more NS1 secreted in the supernatant with the BN22 construct compared to BN07.

The results also showed that NS1 expressed in cells infected with BN22 is antigenic and is recognized by the pooled convalescent patients' sera.

In conclusion, NS1 is expressed in large quantities and in the right confirmation in the BHK cells infected with BN22. Both the dimer and monomer are antigenic, and are recognized by the pooled convalescent patients' sera.

Example 2

Insertion Vectors pBNX67 and pBN27

The MVA sequences adjacent to the new insertion site (at genome position 129940) between the ORF 136L and 137L were isolated by standard PCR amplification of the sequence of interest using the following primers:

oBN543
(TCCCCGCGGAGAGGCGTAAAAGTTAAATTAGAT; SEQ ID NO.:3)
and oBN544
(TGATCTAGAATCGCTCGTAAAAACTGCGGAGGT; SEQ ID NO.:4)

for isolating Flank 1;

oBN578
(CCGCTCGAGTTCACGTTCAGCCTTCATGC; SEQ ID NO.:5)
and oBN579
(CGGGGGCCCTATTTTGTATAATATCTGGTAAG; SEQ ID NO.:6)

for isolating Flank 2.

The PCR fragment comprising Flank 1 was treated with the restriction enzymes SacII and XbaI, and ligated to a SacII/XbaI-digested and dephosphorylated basic vector, pBluescript (Stratagene).

The resulting plasmid was XhoI/ApaI-digested, dephosphorylated and ligated to the XhoI/ApaI-digested PCR fragment comprising Flank 2.

Figure 2A:
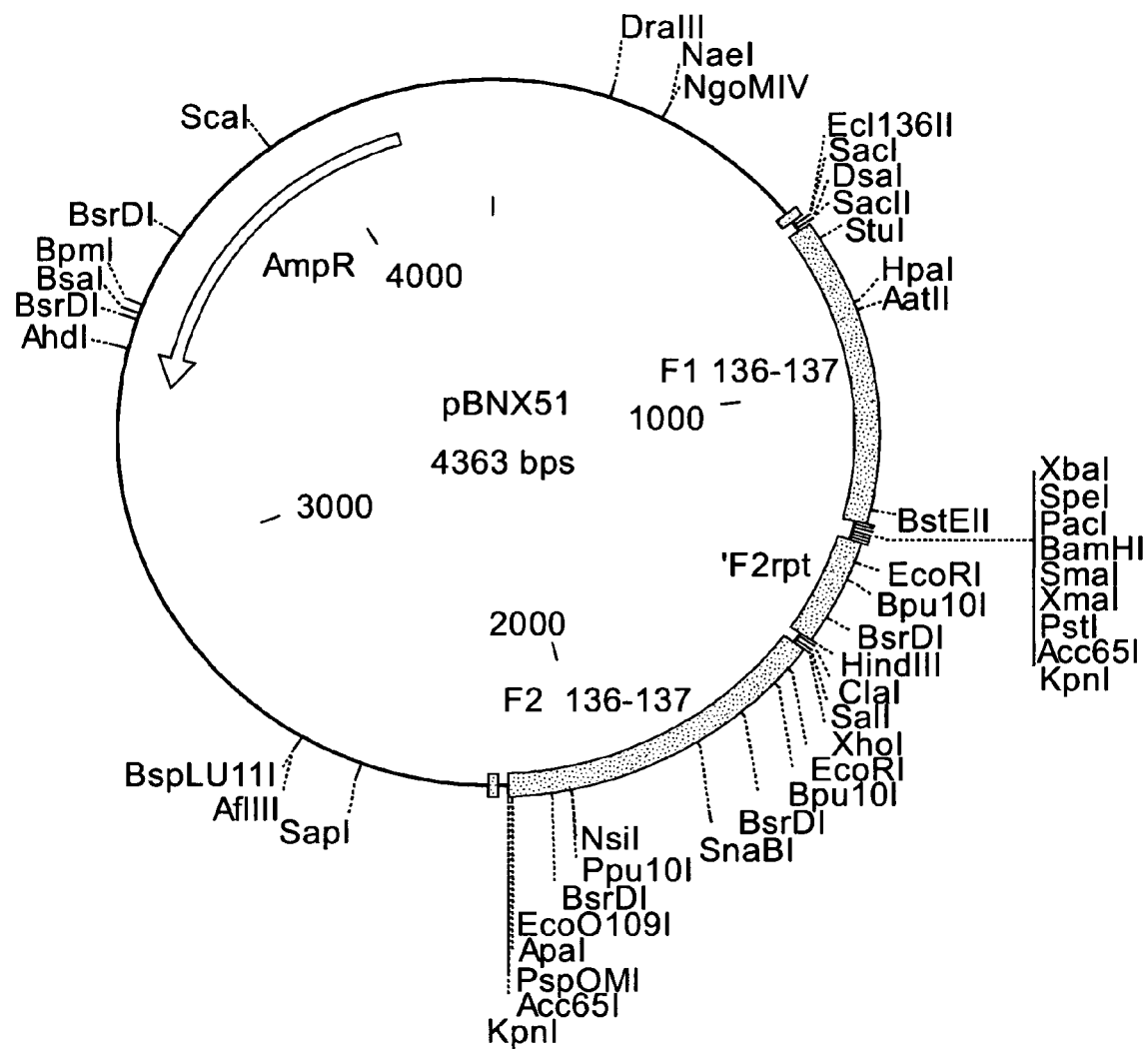
Figure 2B:
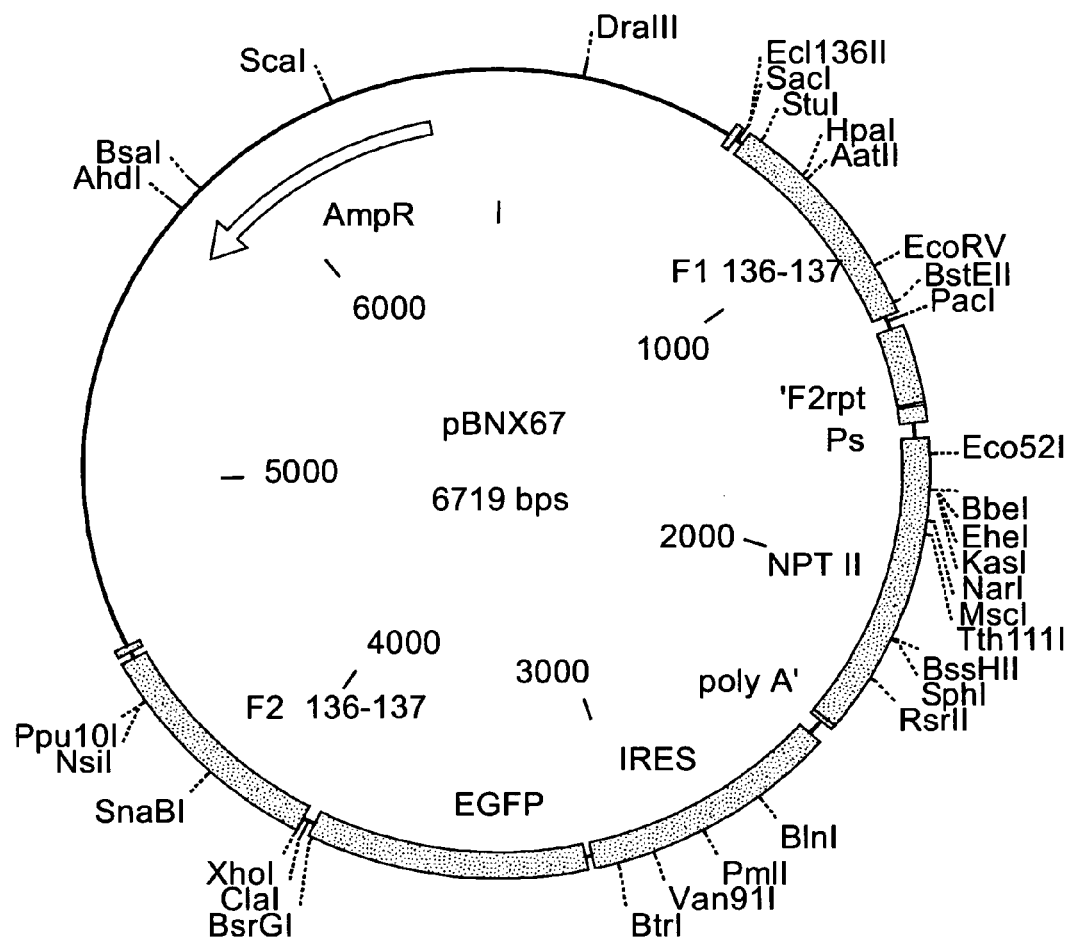
Figure 2C:
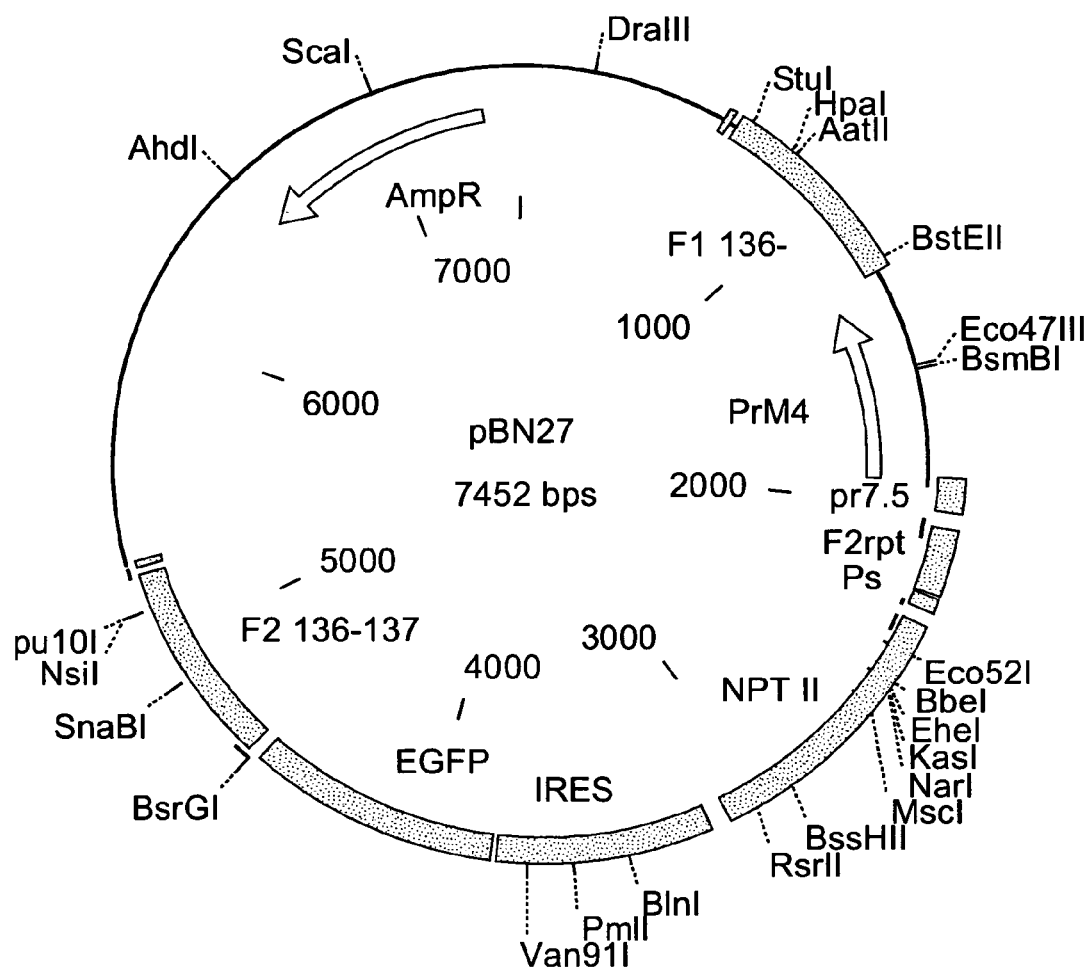

Optionally, a repetitive sequence of Flank 2, which had been isolated by PCR using the primers oBN545 (CGGCTGCAGGGTACCTTCACGTTCAGCCTTCATGC; SEQ ID NO.:7) and oBN546 (CGGAAGCTTTATATGGTTTAGGATATTCTGTTTT; SEQ ID NO.:8), and which became HindIII/PstI-digested, was inserted into the HindIII/PstI site of the resulting vector. FIG. 2A shows the resulting vector (pBNX51).

A reporter cassette comprising a synthetic promoter, NPT II gene (neomycin resistance), poly-A region, IRES, and EGFP gene (Ps-NPTII-polyA-IRES-EGFP) was Ecl136II/XhoI-digested and inserted into the HindIII/XhoI site of the insertion vector, wherein the HindIII site was blunt ended with T4 DNA Polymerase (Roche). A restriction map of an exemplary vector construct according to this example is disclosed in FIG. 2B (pBNX67).

For construction of pBN27 (FIG. 2C) the Dengue virus PrM of serotype 4 was inserted in the single PacI site of pBNX67.

Generation of the Recombinant MVA via Homologous Recombination

The vector pBNX67 (FIG. 2B) can be used to generate a recombinant MVA using the above mentioned protocol. For example, using pBN27 (FIG. 2C) for homologous recombination results in a recombinant MVA carrying Dengue virus PrM4 in the intergenic region between two adjacent ORFs.

Insertion of PrM4 in the IGR136-137 Insertion Site of MVA

In a first round, cells were infected with MVA according to the above-described protocol, and were additionally transfected with insertion vector pBN27 (FIG. 2C) containing the NPT gene for selection, and EGFP (enhanced green fluorescence protein) as a reporter gene. Resulting recombinant viruses were purified by 4 rounds of plaque purification under G418 selection.

Figure 8A:
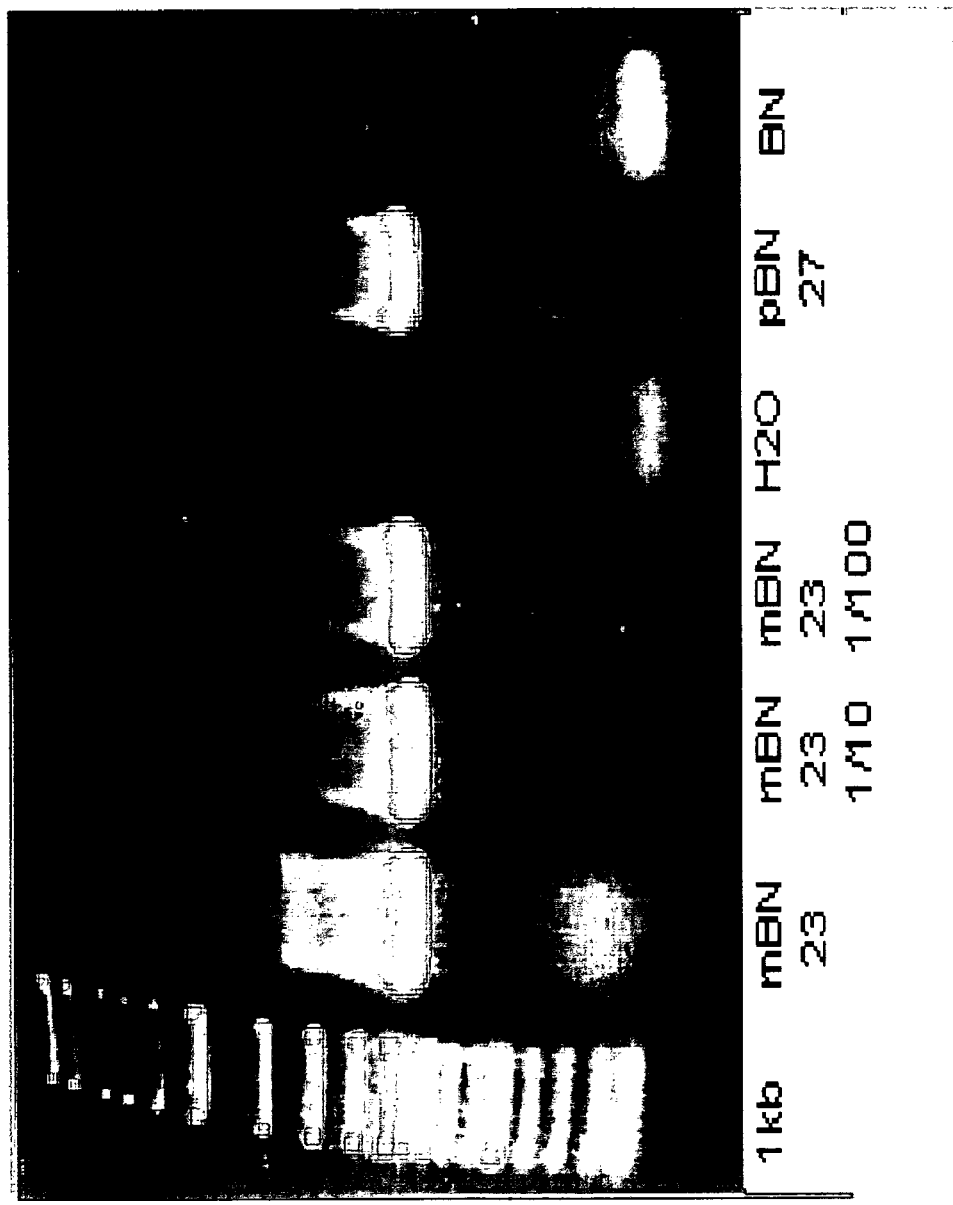
Figure 8B:
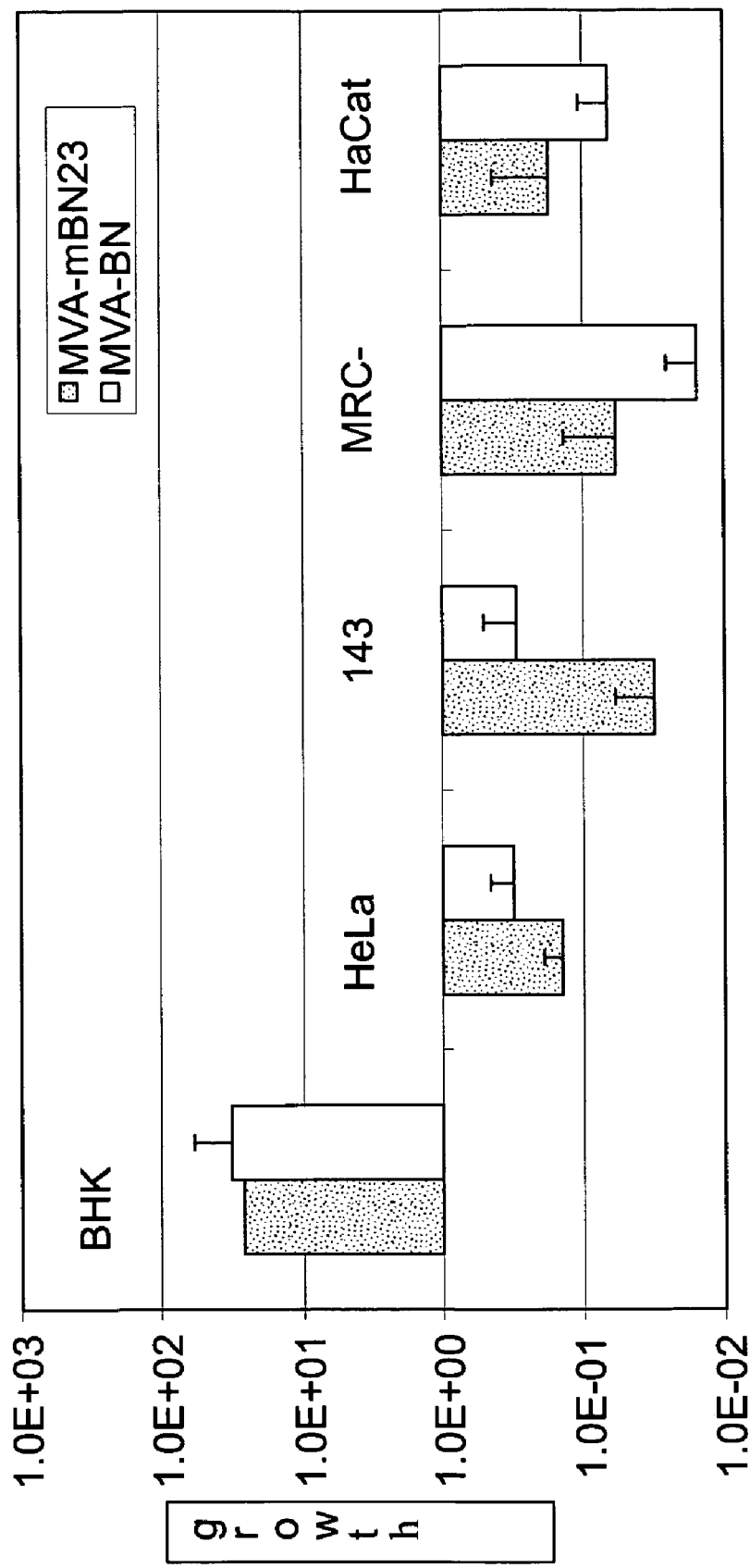

Resulting recombinant viruses were identified by standard PCR assays using a primer pair selectively amplifying the expected insertion site. To amplify the IGR 136-137 insertion site, the primer pair comprising BN900 (cgttcgcatgggttacctcc, SEQ ID NO.:9) and BN901 (gacgcatgaaggctgaac, SEQ ID NO.:10) was used. When the DNA of the empty vector virus MVA is amplified the expected PCR fragment is 88 nucleotides (nt) long. When a recombinant MVA for PrM4 is amplified, which has incorporated Dengue virus PrM4 coding region at the IGR136-137 insertion site, the fragment is expected to be 880 bp. The PCR results in FIG. 8A show clearly the stable insertion of PrM4 in the IGR136-137 insertion site after 22 rounds of virus amplification. The recombinant MVA still shows the same growth characteristics as MVA-BN. It replicates in chicken embryo fibroblasts (CEF cells) and grows attenuated in mammalian cells (FIG. 8B).

Example 3

Insertion vectors pBNX79, pBNX86, pBNX88, pBN34 and pBN56

The MVA sequences adjacent to the new insertion site (at genome position 12800) between the ORF 007R and 008L were isolated by standard PCR amplification of the sequence of interest using the following primers:

```
IGR 07/08 F1up
(CGCGAGCTCAATAAAAAAAAGTTTTAC; SEQ ID NO.:11)
and

IGR 07/08 F1end
(AGGCCGCGGATGCATGTTATGCAAAATAT; SEQ ID NO.:12)
``` for isolating Flank 1;

```
    IGR 07/08 F2up
    (CCGCTCGAGCGCGGATCCCAATATATGGCATAGAAC;
    SEQ ID NO.:13)
    and IGR 07/08 F2end
    (CAGGGCCCTCTCATCGCTTTCATG;
    SEQ ID NO.:14)
``` for isolating Flank 2.

The PCR fragment comprising Flank 1 was treated with the restriction enzymes SacII and SacI, and ligated to a SacII/SacI-digested and dephosphorylated pBluescript plasmid (Stratagene).

The resulting plasmid was XhoI/ApaI-digested, dephosphorylated and ligated to the XhoI/ApaI-digested PCR fragment comprising Flank 2.

Optionally, a repetitive sequence of Flank 2, which had been isolated by PCR using the primers IGR 07/08 F2up (CCGCTCGAGCGCGGATCCCAATATATG-GCATAGAAC; SEQ ID NO.:13) and IGR 07/08 F2mid (TTTCTGCAGTGATATTTATCCAATACTA; SEQ ID NO.:15), and which is BamHI/PstI digested, was inserted into the BamHI/PstI site of the resulting vector.

Figure 3C:
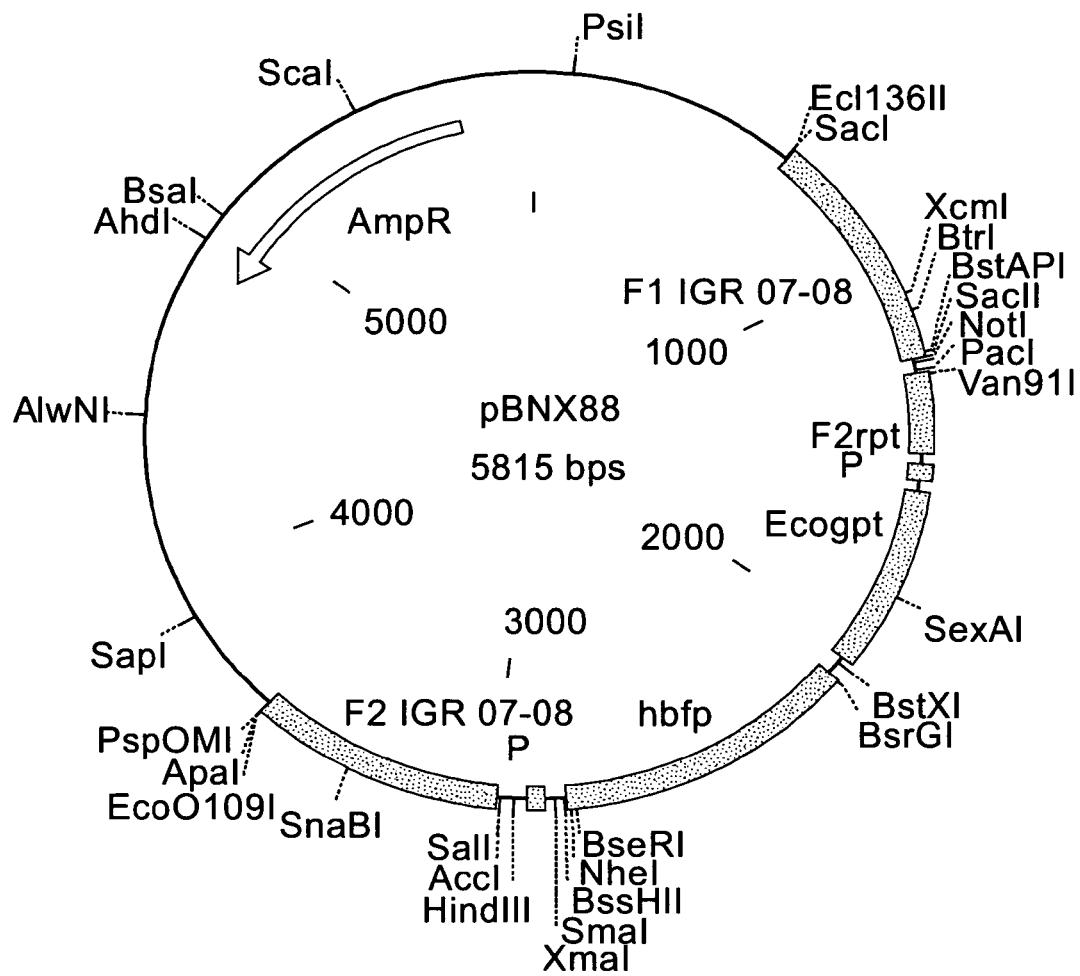
Figure 3D:
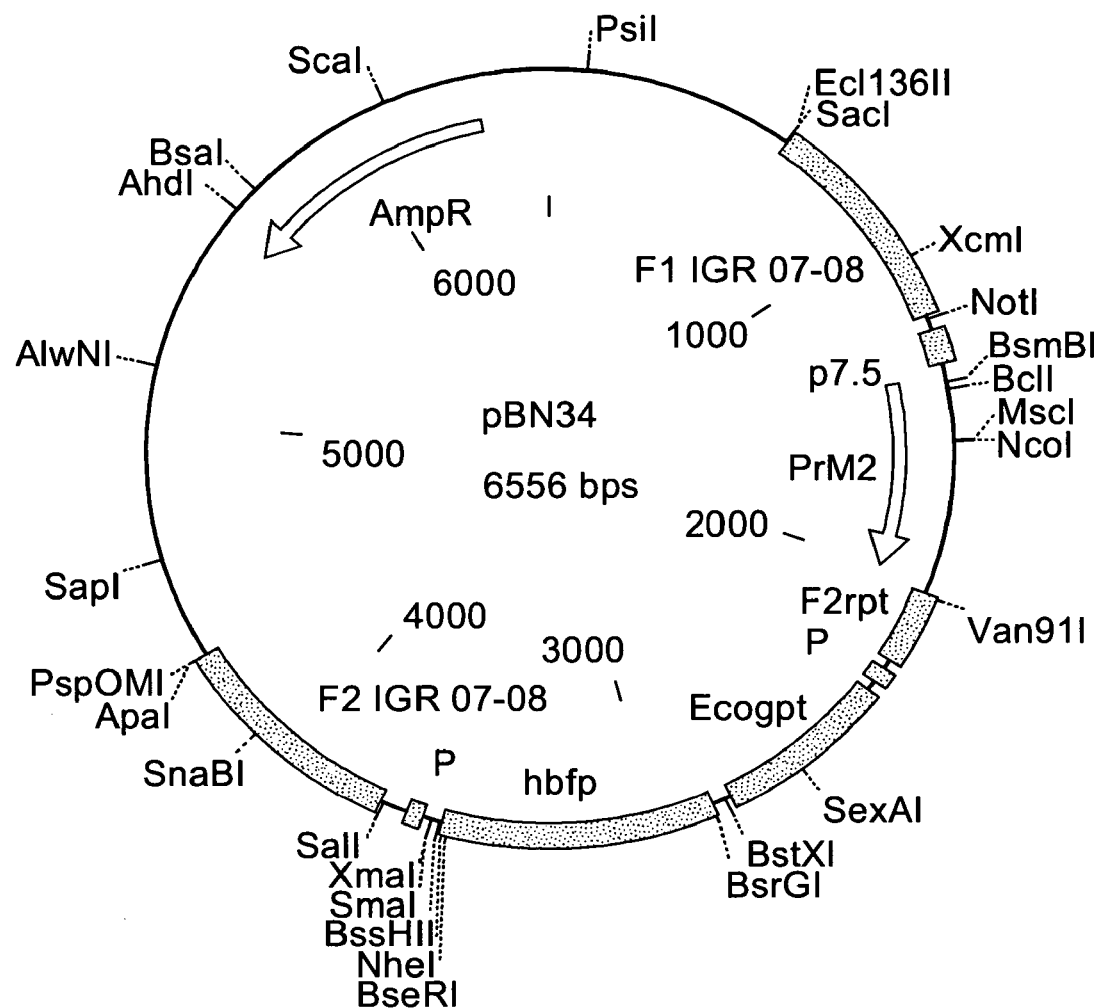
Figure 3E:
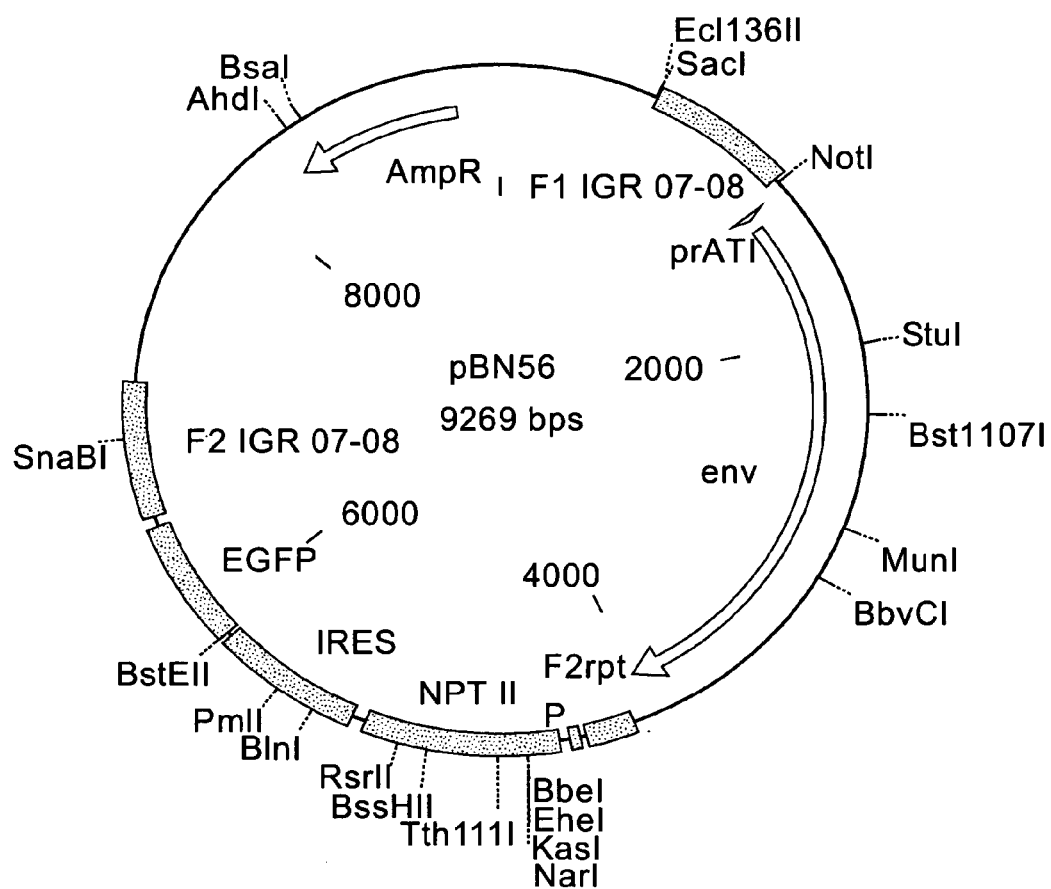

Any reporter or therapeutic gene comprising cassette, having for example a poxviral promoter, a marker gene, a poly-A region and optionally an IRES element, a further gene, for example, one expressing a therapeutically active substance or gene product, can be blunt-ended with T4 DNA Polymerase (Roche) after a restriction digest, and inserted into a suitable cloning site of the plasmid vector. A restriction map of an exemplary vector construct according to this example is disclosed in FIG. 3A (pBNX79). Insertion of the NPT/EGFP selection cassette resulted in vector pBNX86 (FIG. 3B) and insertion of the gpt/BFP selection cassette resulted in vector pBNX88 (FIG. 3C). Considering an expression unit for a therapeutic gene, comprising a therapeutic gene and an operably linked promoter, this expression unit is inserted into the PacI site. For construction of pBN34 (FIG. 3D), the Dengue virus PrM2 was cloned in pBNX88 (FIG. 3C); and for synthesis of pBN56 (FIG. 3E) the HIV env coding region was cloned into the PacI site of pBNX86 (FIG. 3B).

Generation of the Recombinant MVA via Homologous Recombination

The vectors pBNX86 (FIG. 3B) and pBNX88 (FIG. 3C), respectively, can be used to generate a recombinant MVA using the above mentioned protocol. Using pBN34 (FIG. 3D) for homologous recombination results in a recombinant MVA carrying Dengue virus PrM2 in the intergenic region between two adjacent ORFs. Recombination of pBN56 (FIG. 3E) with the MVA-BN genome results in a recombinant MVA, which contains the HIV env gene in the corresponding IGR.

Insertion of PrM2 in the IGR07-08 Insertion Site of MVA

In a first round, cells were infected with MVA according to the above-described protocol, and were additionally transfected with insertion vector pBN34 (FIG. 3D) containing the gpt gene for selection and BFP as reporter gene. Resulting recombinant viruses were purified by 3 rounds of plaque purification under selection by mycophenolic acid, as described in Example 1.

Figure 9A:
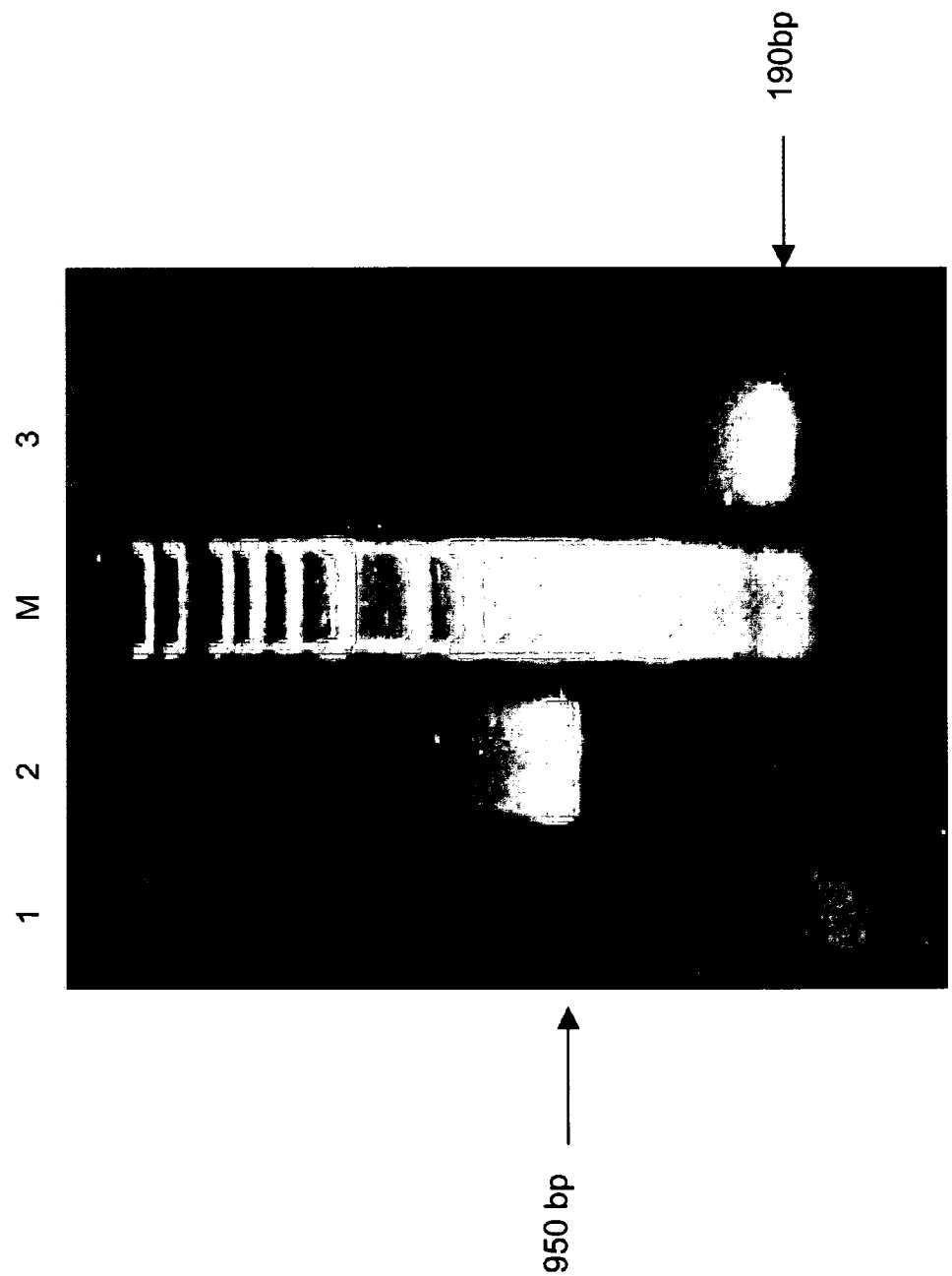
Figure 9B:
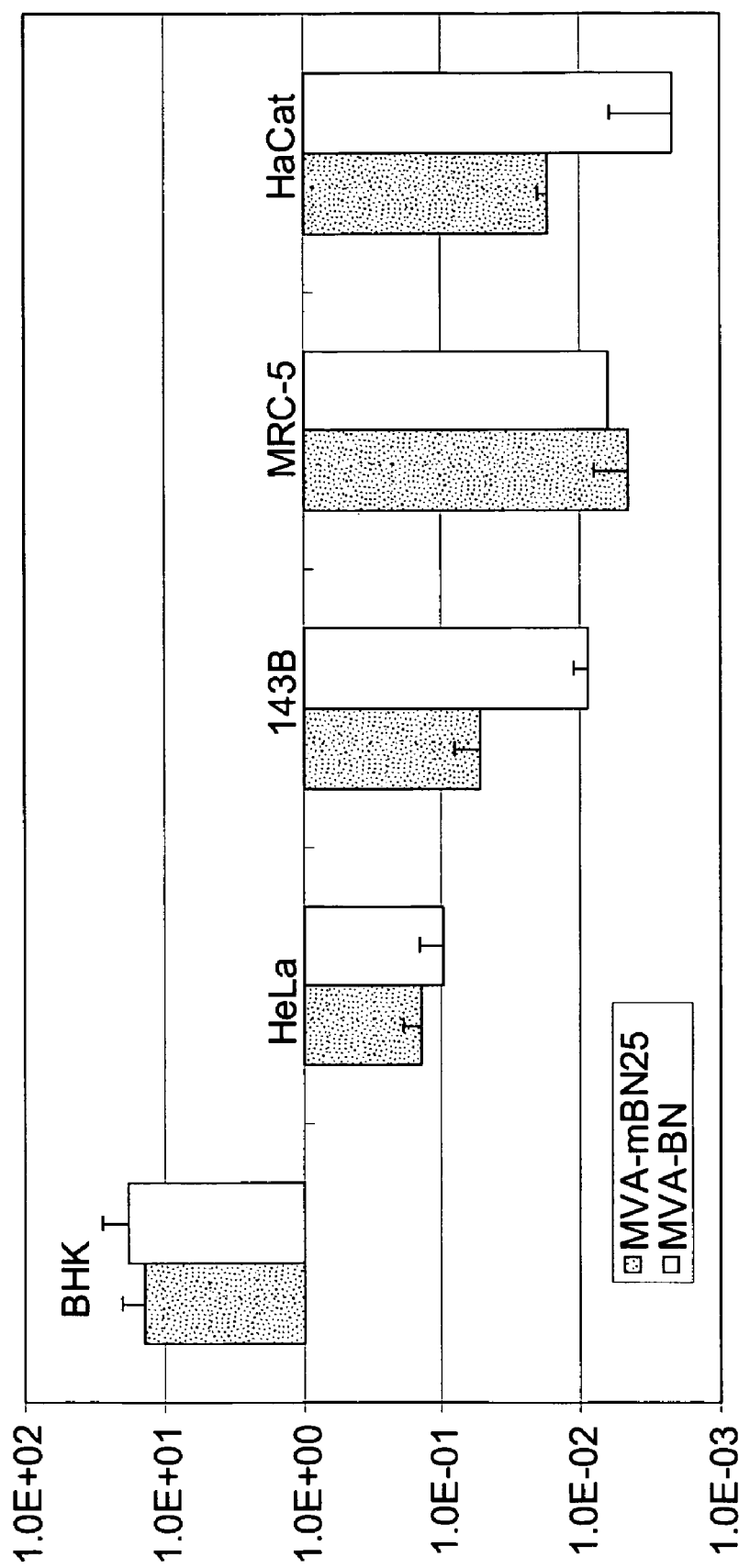

Resulting recombinant viruses were identified by standard PCR assays using a primer pair selectively amplifying the expected insertion site. To amplify the IGR 07-08 insertion site, the primer pair comprising BN902 (ctggataaatacgaggacgtg, SEQ ID NO.:16) and BN903 (gacaattatccgacgcaccg, SEQ ID NO.:17) was used. When the DNA of the empty vector virus MVA is amplified, the expected PCR fragment is 190 nucleotides (nt) long. When a recombinant MVA for PrM2 is amplified, which has incorporated Dengue virus PrM2 coding region at the IGR 07-08 insertion site, the fragment is expected to be 950 bp. The PCR results in FIG. 9A show clearly the stable insertion of PrM2 in the IGR07-08 insertion site after 20 rounds of virus amplification. The recombinant MVA still shows the same growth characteristics as MVA-BN. It replicates in chicken embryo fibroblasts (CEF cells), and grows attenuated in mammalian cells (FIG. 9B).

Insertion of HIV env in the IGR07-08 Insertion Site of MVA

In a first round, cells were infected with MVA according to the above-described protocol and were additionally transfected with insertion vector pBN56 (FIG. 3E) containing the NPT gene for selection and EGFP as reporter gene. Resulting recombinant viruses were purified by 6 rounds of plaque purification under G418 selection.

Figure 10:
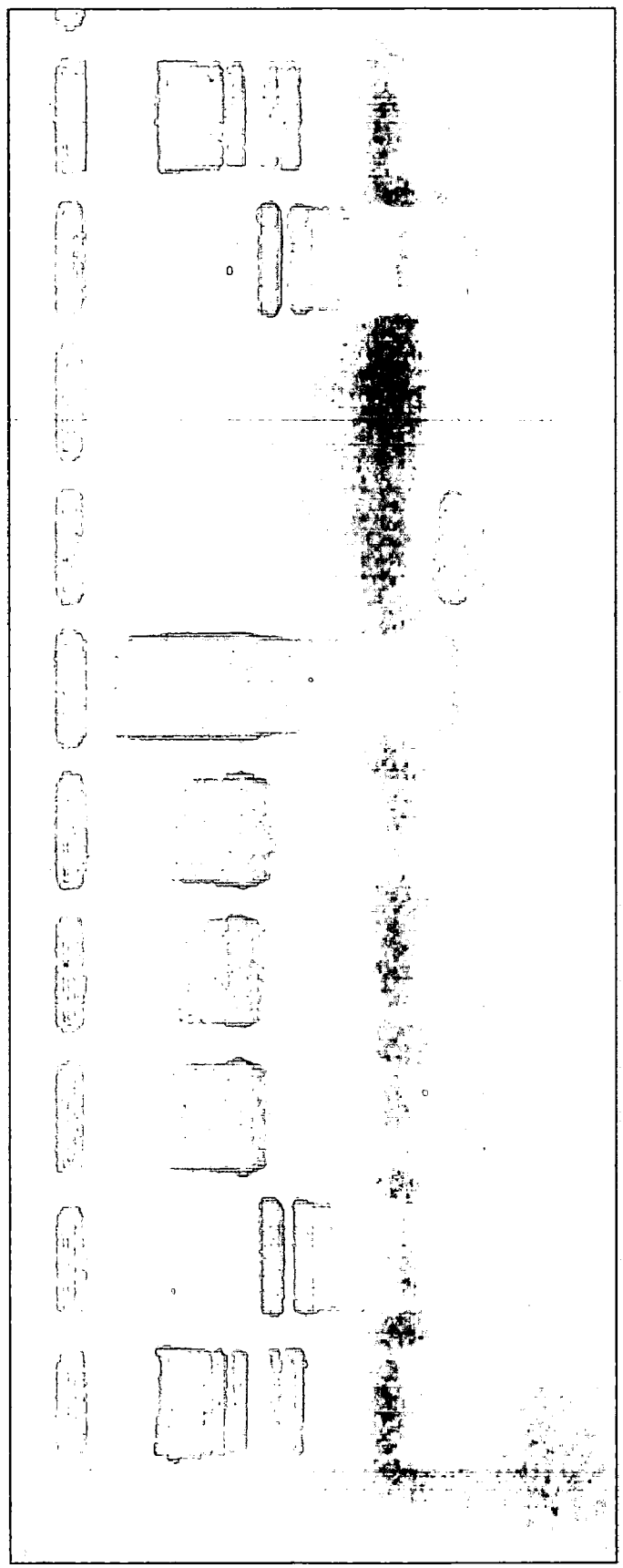

Resulting recombinant viruses were identified by standard PCR assays using a primer pair selectively amplifying the expected insertion site. To amplify the IR 07-08 insertion site, the primer pair comprising BN902 (ctggataaatacgaggacgtg, SEQ ID NO.:16) and BN903 (gacaattatccgacgcaccg, SEQ ID NO.:17) was used. When the DNA of the empty vector virus MVA is amplified the expected PCR fragment is 190 nucleotides (nt) long. When a recombinant MVA for env is amplified, which has incorporated HIV env coding region at the IGR 07-08 insertion site, the fragment is expected to be 2.6 kb. The PCR results in FIG. 10 show clearly the stable insertion of env in the IGR 07-08 insertion site after 20 rounds of virus amplification.

Example 4

Insertion vector pBNX80, pBNX87 and pBN47

The MVA sequences adjacent to the new insertion site (at genome position 37330) between the ORF 044L and 045L were isolated by standard PCR amplification of the sequence of interest using the following primers:

```
IGR44/45F1 up
(CGCGAGCTCATTTCTTAGCTAGAGTGATA; SEQ ID NO.:18)
and

IGR44/45F1 end
(AGGCCGCGGAGTGAAAGCTAGAGAGGG; SEQ ID NO.:19)
``` for isolating Flank 1;

```
    IGR44/45F2up
    (CCGCTCGAGCGCGGATCCTAAACTGTATCGATTATT;
    SEQ ID NO.:20)
    and IGR44/45F2end
    (CAGGGCCCCTAAATGCGCTTCTCAAT;
    SEQ ID NO.:21)
``` for isolating Flank 2.

The PCR fragment comprising Flank 1 was treated with the restriction enzymes SacII and SacI, and ligated to a SacII/SacI-digested and dephosphorylated basic vector, pBluescript (Stratagene).

The resulting plasmid was XhoI/ApaI digested, dephosphorylated and ligated to the XhoI/ApaI-digested PCR fragment comprising Flank 2.

Optionally, a repetitive sequence of Flank 2, which had been isolated by PCR using the primers IGR44/45F2up (CCGCTCGAGCGCGGATCCTAAACTG-TATCGATTATT; SEQ ID NO.:20) and IGR44/45F2mid (TTTCTGCAGCCTTCCTGGGTTTGTATTAACG; SEQ ID NO.:22), and which became BamHI/PstI-digested, was inserted into the BamHI/PstI site of the resulting vector.

Figure 4A:
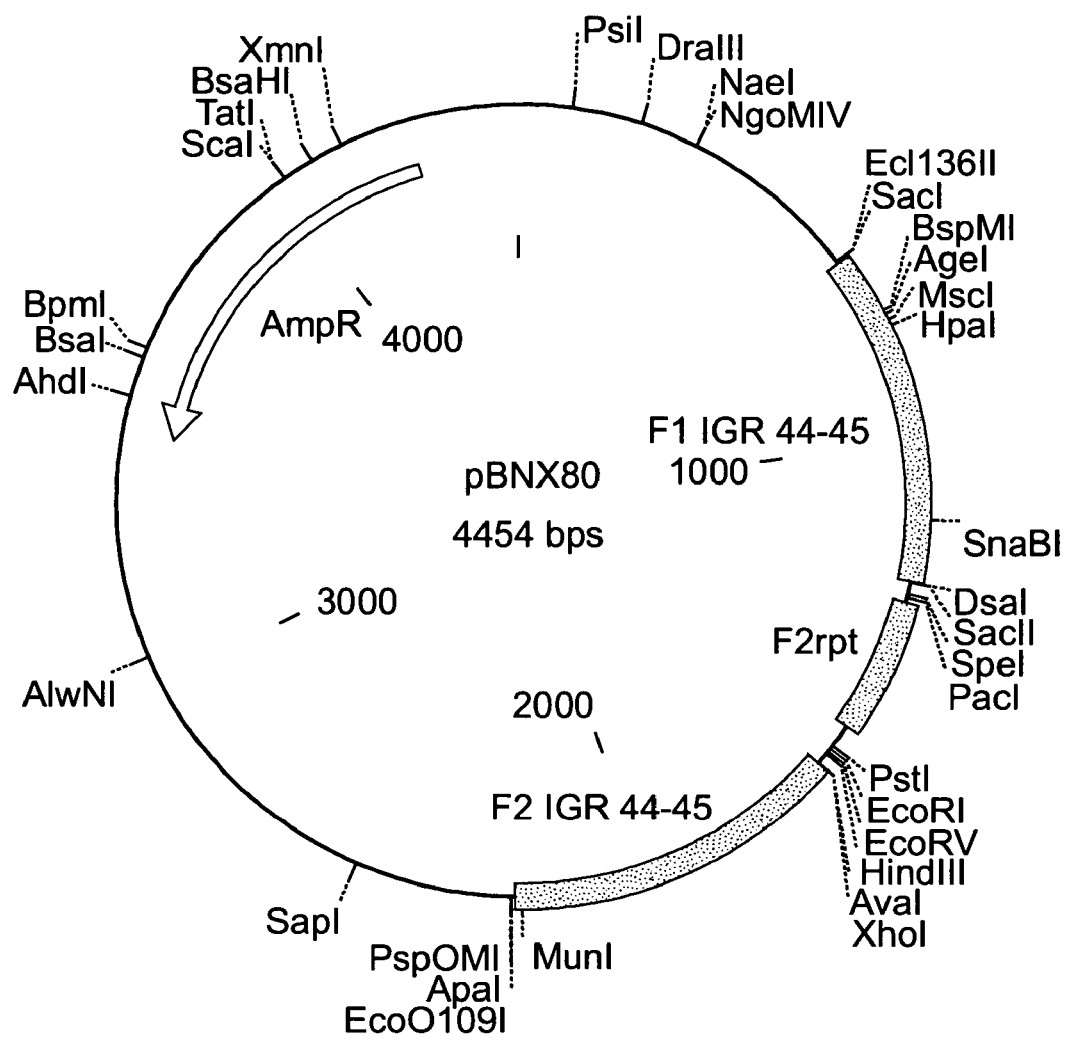

Any reporter or therapeutical gene comprising cassette, having for example a poxviral promoter, a marker gene, a poly-A region and optionally an IRES element, a further gene, for example expressing a therapeutically active substance or gene product, can be blunt ended with T4 DNA Polymerase (Roche) after a restriction digest, and inserted into a suitable cloning site of the plasmid vector. Considering a reporter gene cassette, the PstI, EcoRI, EcoRV, HindIII, AvaI, or XhoI restriction enzyme site between Flank 2 and the Flank-2-repetition is preferred as a cloning site. For the construction of pBNX87 (FIG. 4B), the NPT/EGFP selection cassette was inserted in pBNX80 (FIG. 4A). Considering an expression unit for a therapeutic gene, comprising a therapeutic gene and an operably linked promoter, this expression unit is inserted into the PacI site.

Figure 4B:
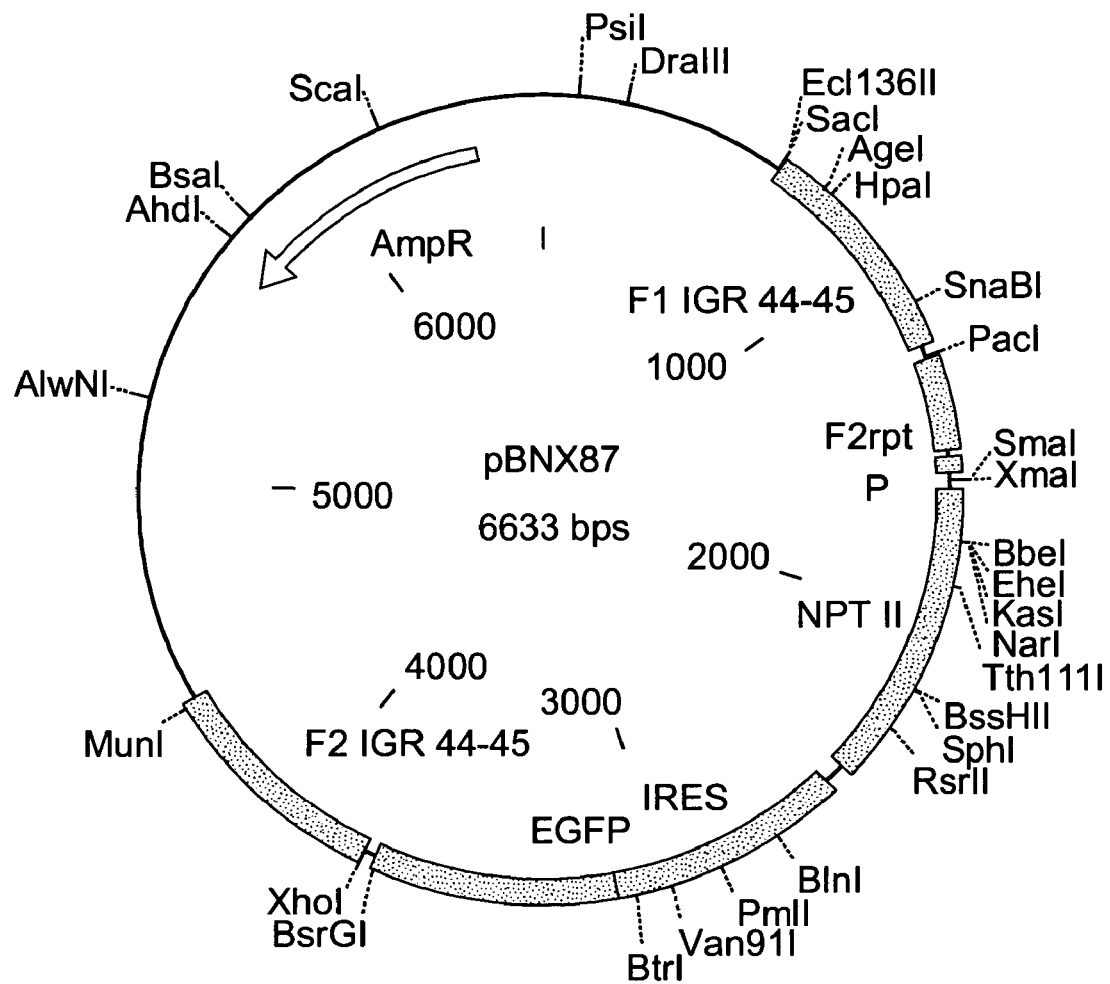
Figure 4C:
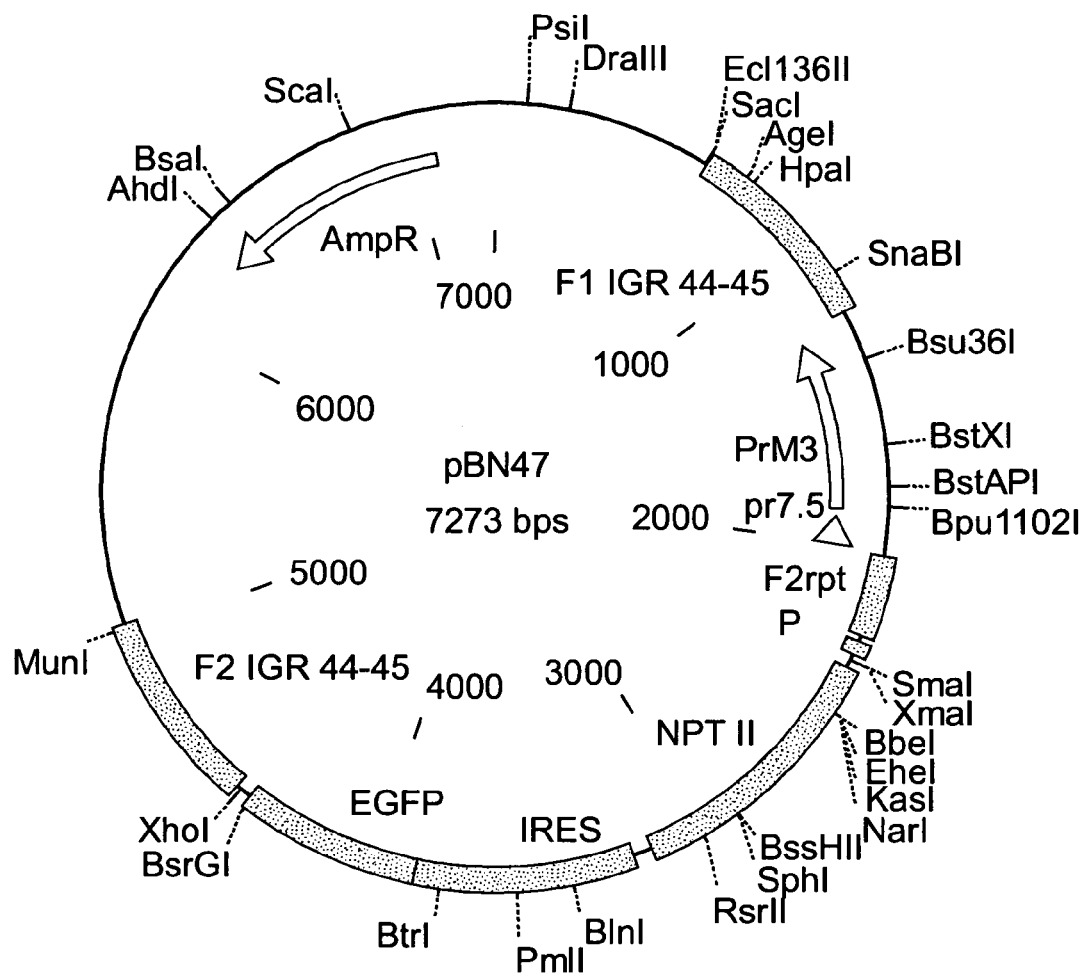

Restriction maps of exemplary vector constructs according to this example are disclosed in FIGS. 4A and 4B (pBNX80, pBNX87).

The vector can be used to generate a recombinant MVA, following the above-mentioned protocol, carrying an exogenous sequence in the intergenic region between two adjacent ORFs.

For the construction of pBN47 (FIG. 4C), the PrM of Dengue virus serotype 3 was cloned into pBNX87 (FIG. 4B).

Insertion of PrM3 in the IGR44-45 Insertion Site of MVA

In a first round, cells were infected with MVA according to the above-described protocol, and were additionally transfected with insertion vector pBN47 (FIG. 4C), containing the NPT gene for selection and EGFP as reporter gene. Resulting recombinant viruses were purified by 3 rounds of plaque purification under G418 selection.

Figure 11A:
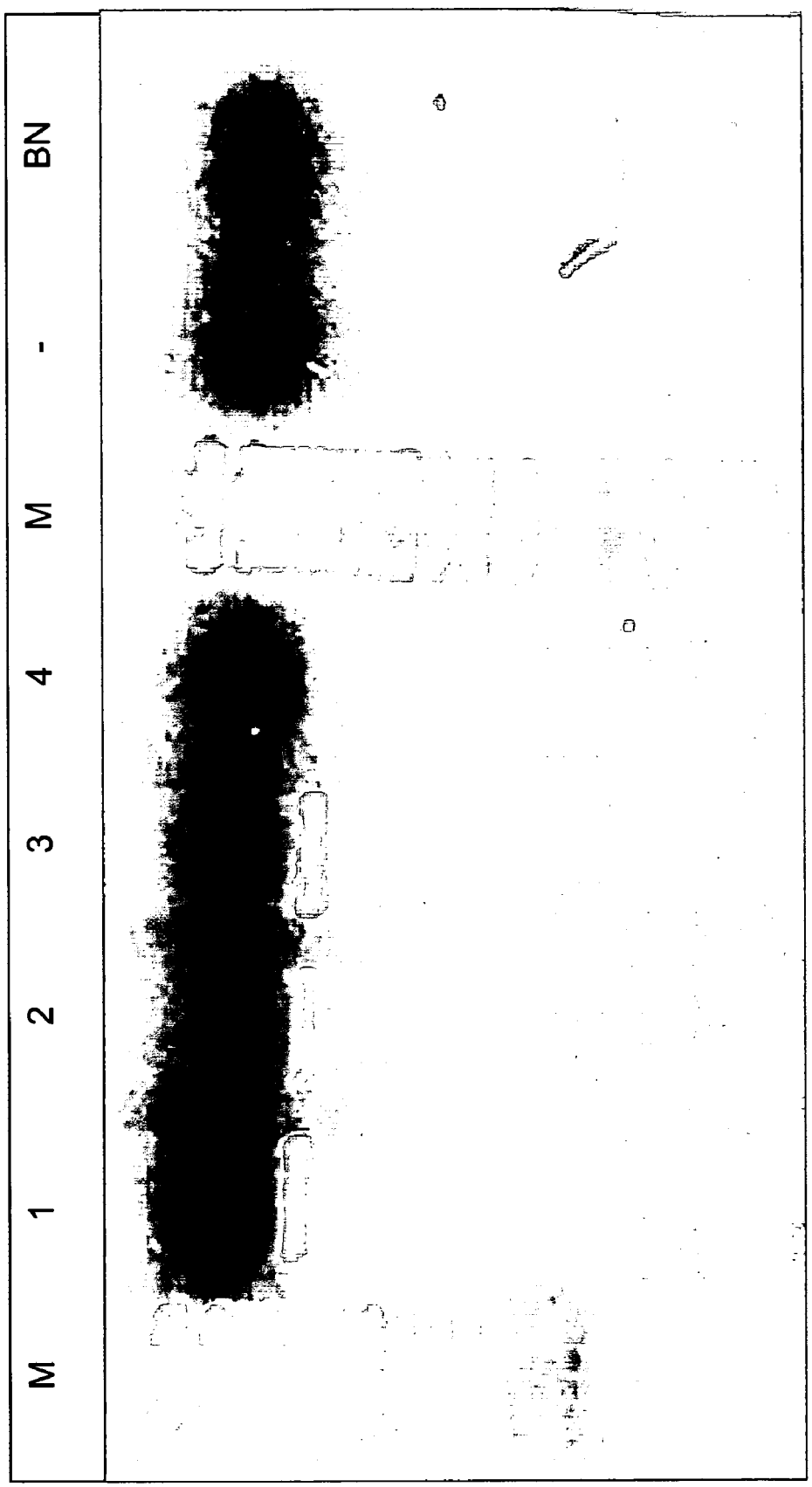
Figure 11B:
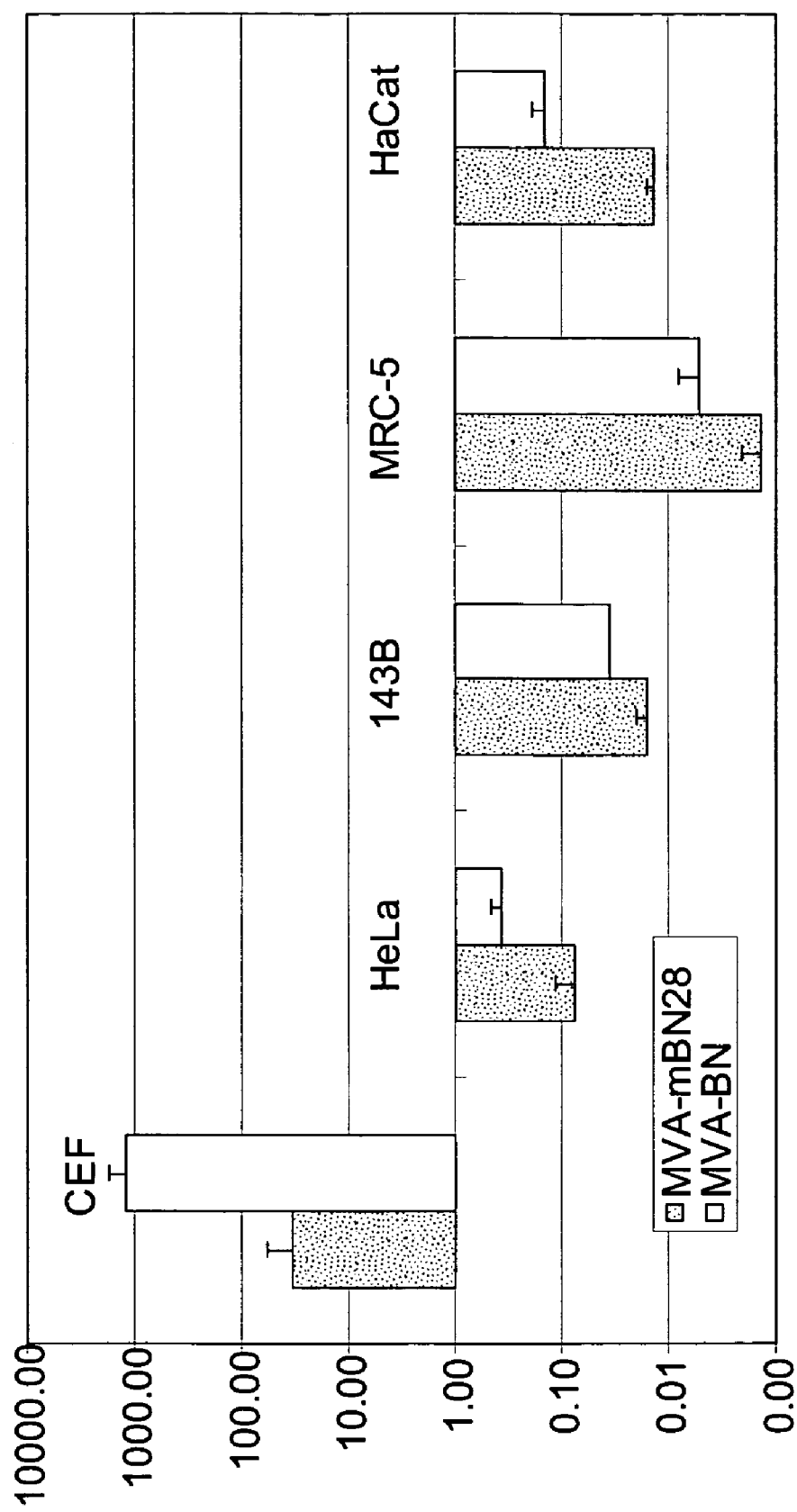

Resulting recombinant viruses were identified by standard PCR assays using a primer pair selectively amplifying the expected insertion site. To amplify the IGR 44-45 insertion site, the primer pair comprising BN904 (cgttagacaacacac-cgacgatgg, SEQ ID NO.:23) and BN905 (cggatgaaaaattttg-gaag, SEQ ID NO.:24) was used. When the DNA of the empty vector virus MVA is amplified, the expected PCR fragment is 185 nucleotides (nt) long. When a recombinant MVA for PrM3 is amplified, which has incorporated Dengue virus PrM3 coding region at the IGR 44-45 insertion site, the fragment is expected to be 850 bp. The PCR results in FIG. 11A show clearly the stable insertion of PrM3 in the IGR44-45 insertion site after 19 rounds of virus amplification. The recombinant MVA (MVA-mBN28) still shows the same growth characteristics as MVA-BN. It replicates in chicken embryo fibroblasts (CEF cells) and grows attenuated in mammalian cells (FIG. 11B).

Example 5

Insertion Vectors pBNX90, pBNX92 and pBN54

The MVA sequences adjacent to the new insertion site (at genome position 137496) between the ORFs 148R and 149L were isolated by standard PCR amplification of the sequence of interest using the following primers:

```
    IGR148/149F1 up
    (TCCCCGCGGGGACTCATAGATTATCGACG;
    SEQ ID NO.:25)
    and IGR148/149F1 end
    (CTAGTCTAGACTAGTCTATTAATCCACAGAAATAC;
    SEQ ID NO.:26)
``` for isolating Flank 1;

```
    IGR148/149F2up
    (CCCAAGCTTGGGCGGGATCCCGTTTCTAGTATGGGGATC;
    SEQ ID NO.:27)
    and IGR148/149F2end
    (TAGGGCCCGTTATTGCCATGATAGAG;
    SEQ ID NO.:28)
``` for isolating Flank 2.

The PCR fragment comprising Flank 1 was treated with the restriction enzymes SacII and XbaI, and ligated to a SacII/XbaI-digested and dephosphorylated basic vector, pBluescript (Stratagene).

The resulting plasmid was HindIII/ApaI digested, dephosphorylated and ligated to the HindIII/ApaI-digested PCR fragment comprising Flank 2.

Optionally, a repetitive sequence of Flank 2, which had been isolated by PCR using the primers IGR148/149F2up (CCCAAGCTTGGGCGGGATC-CCGTTTCTAGTATGGGGATC; SEQ ID NO.:27) and IGR148/149F2mid (TTTCTGCAGTGTATAATACCAC-GAGC; SEQ ID NO.:29) and which became BamHI/PstI-digested, was inserted into the BamHI/PstI site of the resulting vector.

Any reporter or therapeutic gene comprising cassette, having for example a poxviral promoter, a marker gene, a poly-A region, and optionally an IRES element, a further gene, for example, a gene expressing a therapeutically active substance or gene product, can be blunt ended with T4 DNA Polymerase (Roche) after a restriction digest and inserted into a suitable cloning site of the plasmid vector. For construction of pBNX92 (FIG. 5B), the gpt/BFP expression cassette was inserted in this cloning site. Considering a reporter gene cassette, the PstI, EcoRI, EcoRV, and HindIII restriction enzyme site between Flank 2 and the Flank-2-repitition is preferred as a cloning site. Considering an expression unit for a therapeutic gene, comprising a therapeutic gene and an operably linked promoter, this expression unit is inserted into the PacI site. For construction of pBN54 (FIG. 5C) the Dengue virus PrM1 was inserted in this PacI site.

Figure 5A:
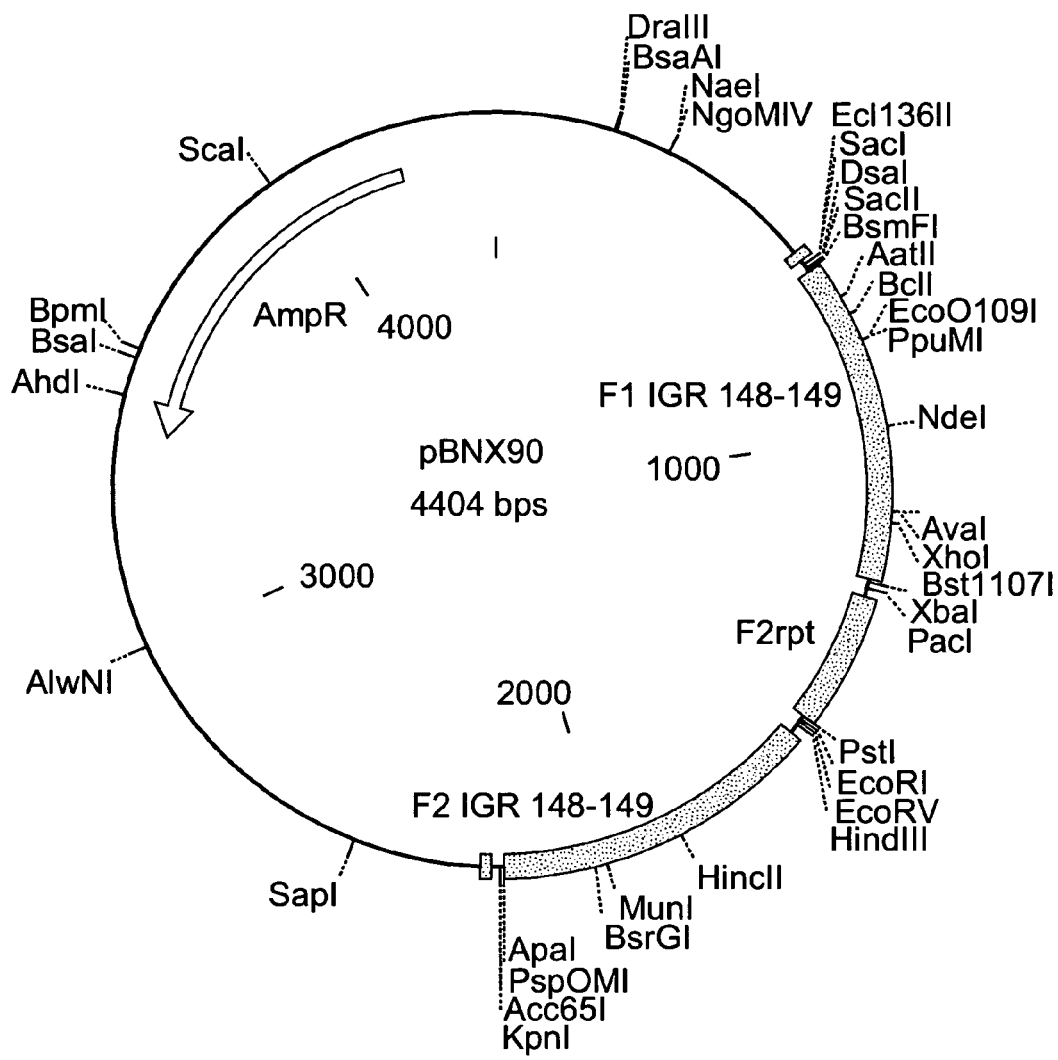
Figure 5B:
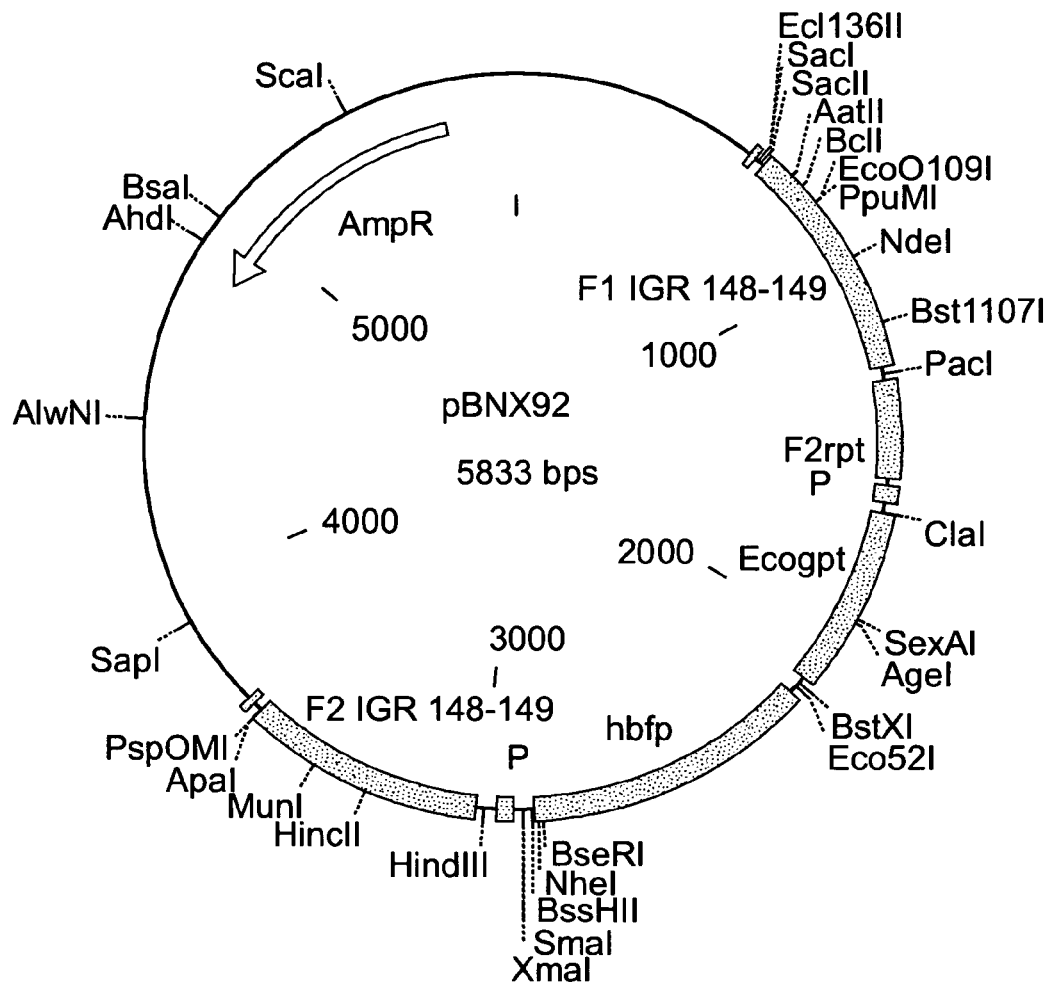
Figure 5C:
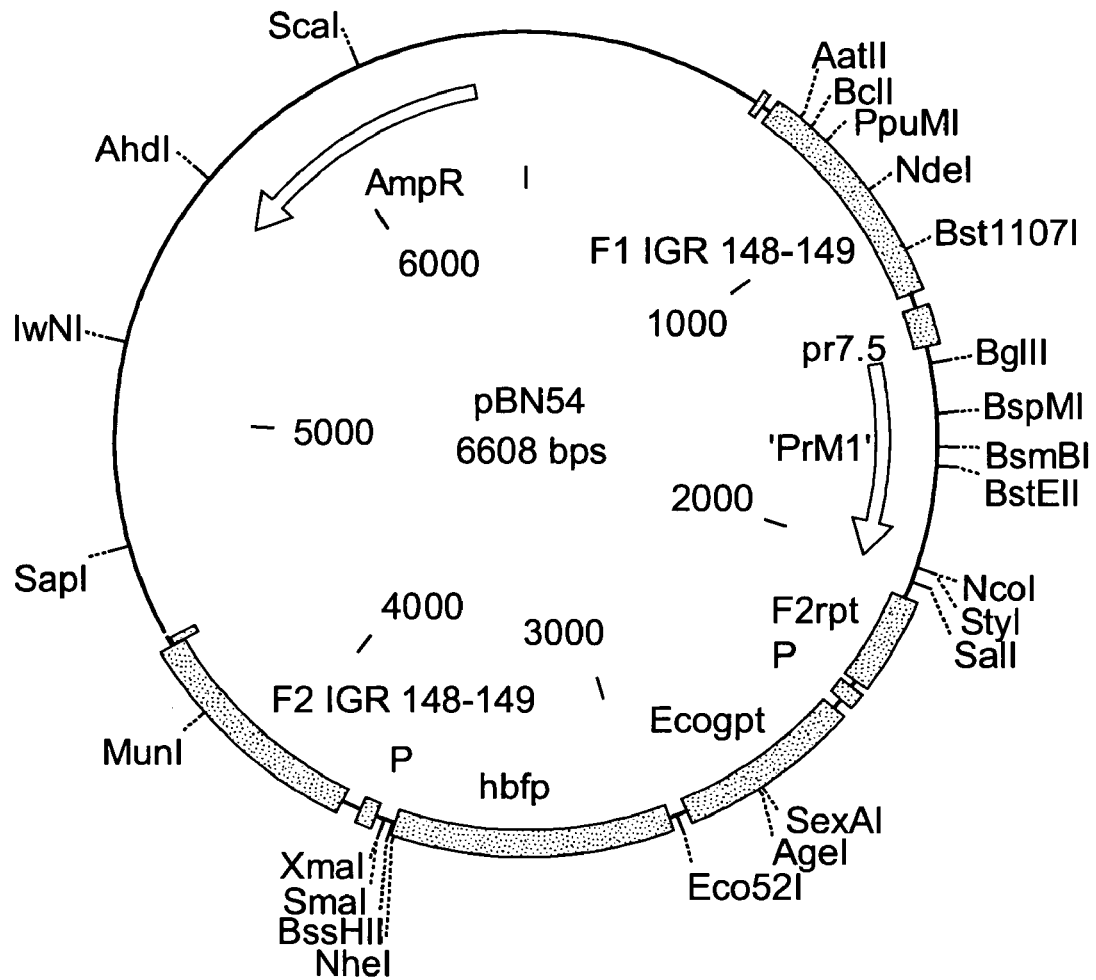
Figure 6:
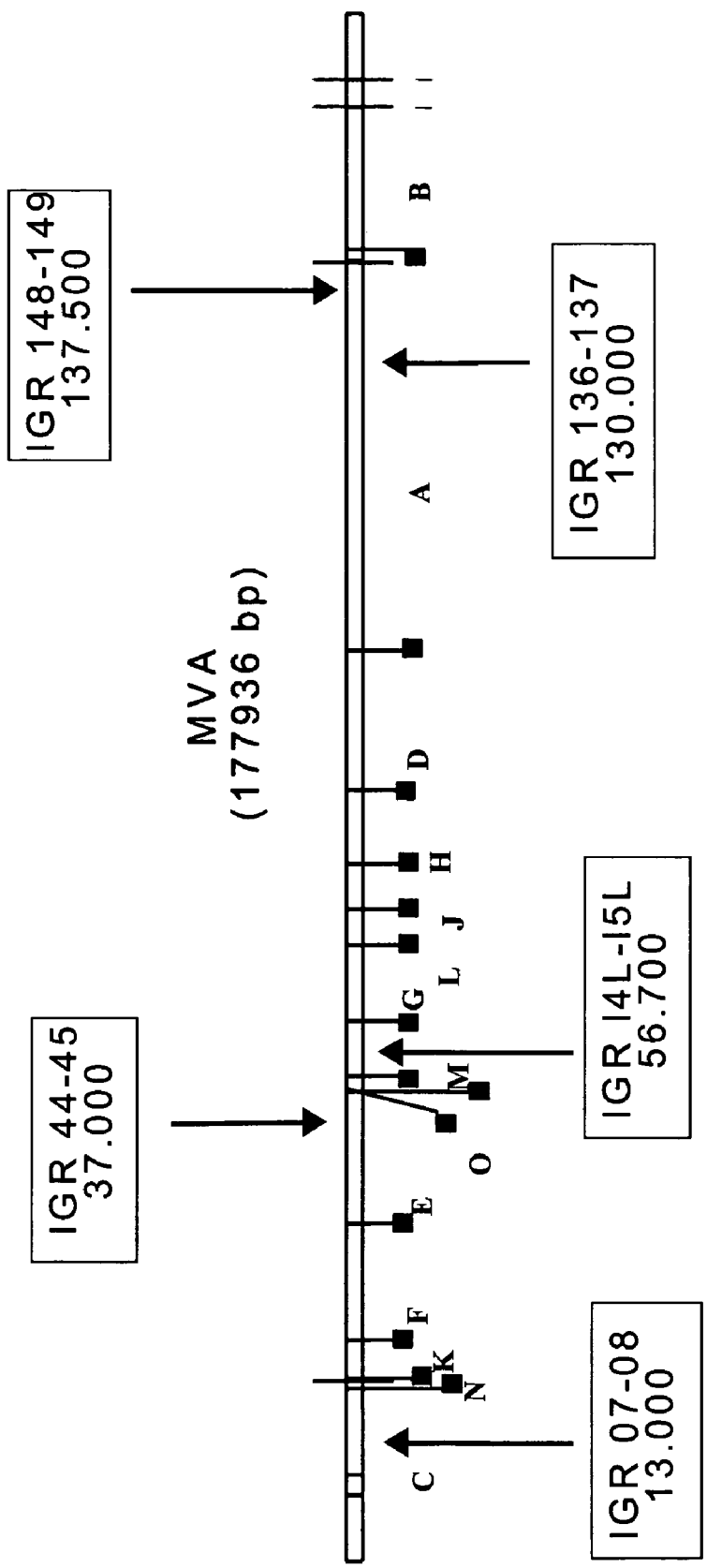
Figure 7:
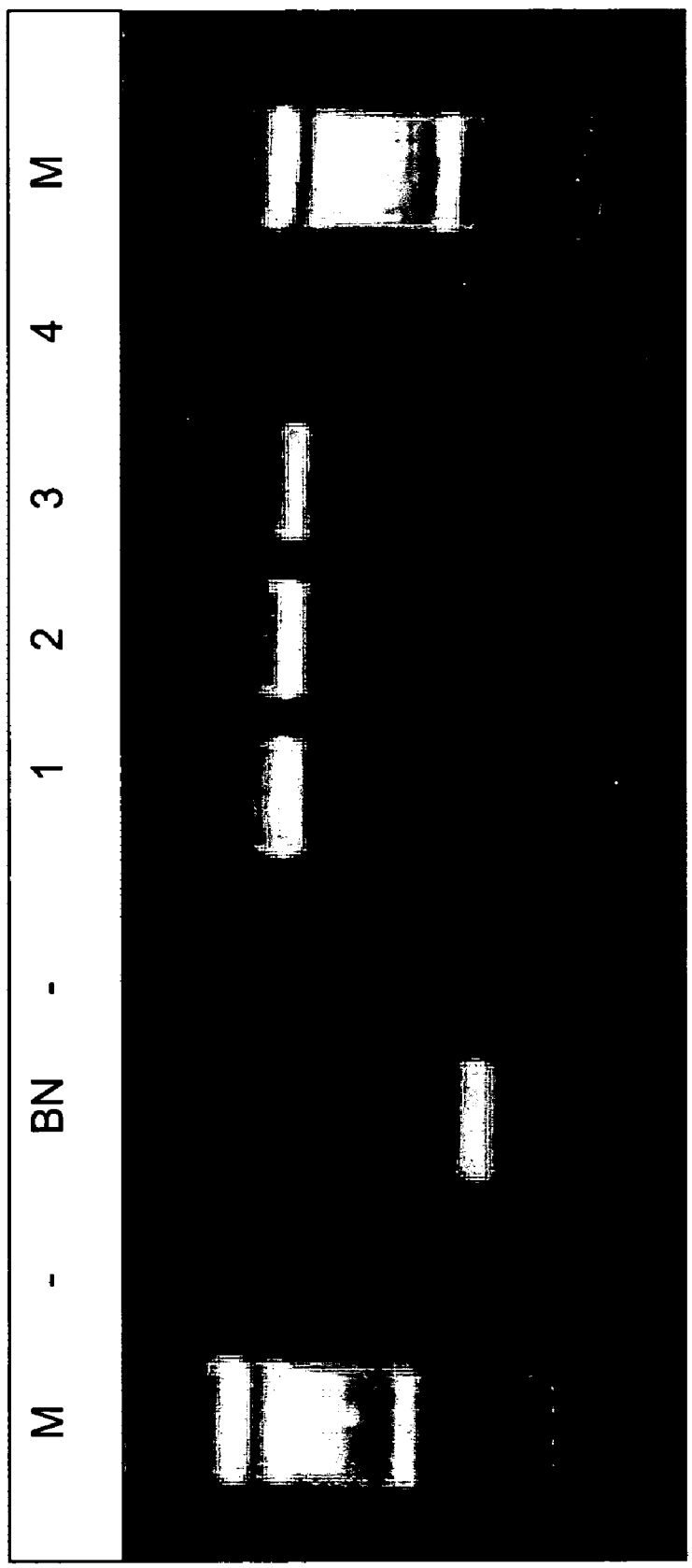

Restriction maps of exemplary vector constructs according to this Example are disclosed in FIGS. 5A and 5B (pBNX90, pBNX92).

The vector can be used to generate a recombinant MVA, following the above-mentioned protocol, carrying an exogenous sequence in the intergenic region between two adjacent ORFs. For the generation of a recombinant MVA expressing the Dengue virus PrM1, pBN54 (FIG. 5C) was used for a homologous recombination.

Insertion of PrM1 in the IGR148-149 Insertion Site of MVA

In a first round, cells were infected with MVA according to the above-described protocol and were additionally transfected with insertion vector pBN54 (FIG. 5C) containing the gpt gene for selection and BFP as reporter gene. Resulting recombinant viruses were purified by 3 rounds of plaque purification under selection with mycophenolic acid.

Figure 12B:
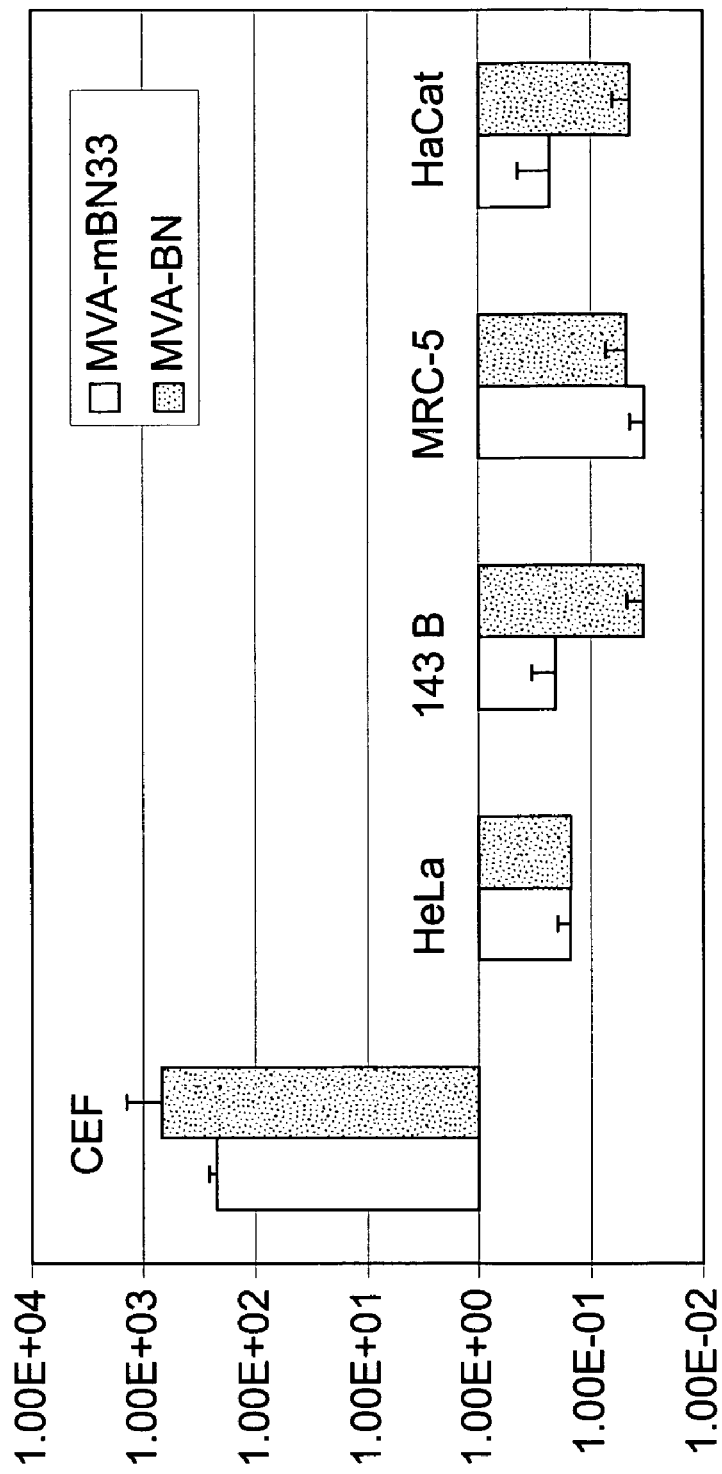
FIG. 12B shows the multiple step growth curve for MVA-BN empty vector and the recombinant MVA with PrM1 inserted in IGR 44-45 (MVA-mBN33).

Resulting recombinant viruses were identified by standard PCR assays using a primer pair selectively amplifying the expected insertion site. To amplify the IGR148-149 insertion site, the primer pair comprising BN960 (ctgtataggtatgtcctct-gcc, SEQ ID NO.:30) and BN961 (gctagtagacgtggaaga, SEQ ID NO.:31) was used. When the DNA of the empty vector virus MVA is amplified the expected PCR fragment is 450 nucleotides (nt) long. When a recombinant MVA for PrM1 is amplified, which has incorporated Dengue virus PrM1 coding region at the IGR148-149 insertion site, the fragment is expected to be 1200 bp. The PCR results in FIG. 12*a* show clearly the stable insertion of PrM1 in the IGR148-149 insertion site after 23 rounds of virus amplification. The recombinant MVA still shows the same growth characteristics as MVA-BN, namely, it replicates in chicken embryo fibroblasts (CEF cells) and grows attenuated in mammalian cells (FIG. 12*b*).

Example 6

Generation of a Recombinant MVA-BN Comprising in the Viral Genome a Truncated nef Gene, a gag-pol Fusion Gene, a Transdominant Tat Gene and a Vif-Vpr-Vpu-Rev Fusion Gene, Each Under the Control of the ATI Promoter Origin of the HIV Genes delta nef, gag-pol, vif-vpr-vpu-rev and tat The Gag-pol fused gene was obtained by PCR from DNA from HXB2 infected cells. The Nef gene was amplified by PCR from DNA of MVA-nef (LAI) to obtain a truncated version. The first 19 aa were deleted resulting in Nef-truncated. The Vif and Vpu genes were generated by RT-PCR from HIV RNA from a primary isolate MvP-899, while the Vpr, Rev and Tat genes were synthesized by oligo annealing based on the sequence of HXB2. The protein tat-mutated was created by introducing two mutations in tat, which are not localized in important epitopes but lead to the loss of trans-activating activity. The mutations are the following substitutions: 22 (Cys>Gly) and 37 (Cys>Ser).

The DNA constructs were cloned into recombinant vectors.

Transfer Vectors pBNX59, pBNX67 and pBNX86 pBNX59, pBN67 and pBNX86 are plasmid vectors containing MVA DNA sequences that are homologous to intergenic regions. When an expression cassette is inserted into such an MVA sequence in a plasmid, it is possible to use the resulting plasmid for homologous recombination of the expression cassettes into the homologous intergenic non-coding region of the MVA genome. pBNX59 directs homologous recombination into IGR I4L-I5L; pBNX67 (see example 2) directs homologous recombination into IGR 136-137, and pBNX86 (see example 3) directs homologous recombination into IGR 07-08 of the MVA genome.

MVA DNA sequences spanning the intergenic regions between coding regions I4L and I5L (i.e. IGR I4L-I5L), 136 and 137 (i.e. IGR 136-137), and 07 and 08 (i.e. IGR 07-08) in the HindIII I fragment of the MVA genome, were amplified and cloned into pBluescript KS+. The coding sequence for the *E. coli* gpt gene under the control of a strong synthetic Vaccinia virus promoter was inserted between I4l and I5L flanks to generate the plasmid pBNX59.

The coding sequences for NPTII and a further marker gene (EGFP) under the control of a vaccinia virus promoter (Ps) were inserted between 136 and 137 flanks of MVA DNA to generate the recombination vector pBNX67 (for details, see FIG. 2B and Example 2) that allows the selection of recombinant viruses.

The coding sequences for NPTII and a further marker gene (EGFP) under the control of a strong Vaccinia virus promoter (P) were inserted between 07 and 08 flanks of MVA DNA to generate the plasmid pBNX86 (for details, see FIG. 3B and Example 3).

Sequence repeats of flank 2 were inserted in order to allow the deletion of the selection cassettes after isolation of recombinant viruses.

Cloning and Generation of MVA-mBN87B Comprising in the Viral Genome a Truncated nef Gene, a gag-pol Fusion Gene, a Transdominant Tat GBene and a Vif-Vpr-Vpu-Rev Fusion Gene, Each Under the Control of the ATI Promoter To create a recombinant MVA-BN strain which expresses the several multiantigen constructs, the recombination plasmids pBN108, pBN131 and pBN175 were created (see below).

Plasmid pBN108 (FIG. 13A) was obtained as described below. It comprises a gag-pol fusion gene and a transdominant Tat, each under the control of the ATI promoter. pBN108 was then transfected into primary CEF cells infected with mBN67B. The double recombinant MVA virus mBN78A, which carried gpt, a further marker gene, truncated nef, and the transdominant tat and gag-pol fusion coding region, was obtained after multiple plaque purifications under selective conditions of recombinant MVA from fluorescing plaques. Then, the selection cassette was deleted, by leaving out selection conditions, and mBN78B was obtained.

pBN131 (FIG. 13B), obtained as described below, was transfected into primary CEF cells infected with MVA-BN. The resulting recombinant MVA virus mBN67A, which carried the NPTII, a further marker gene (EGFP), and the truncated nef coding region, was obtained after multiple plaque purifications, under selective conditions of recombinant MVA, from fluorescing plaques (the fluorescence being conferred by the presence of the EGFP marker). Then, the selection cassette was deleted, by leaving out selection conditions, and mBN67B was obtained.

In parallel, plasmid pBN175 (FIG. 13C) was generated as described below. It comprises the vif-vpr-vpu-rev coding region under the control of the ATI promoter. pBN175 was then transfected into primary CEF cells infected with mBN78B. The triple recombinant MVA virus mBN87A, which carried a marker gene and gpt and the vif-vpr-vpu-rev coding region, was obtained after multiple plaque purifications under selective conditions of recombinant MVA from fluorescing plaques. After amplification and plaque purification under non-selective conditions the recombinant virus MVA-mBN87B, devoid of the selection cassettes, was isolated.

Cloning of the Recombination Plasmid pBN131 Comprising a Truncated Nef Gene Under the Control of the ATI Promoter The nef gene was generated by PCR out of a recombinant MVA comprising the nef gene, and the purified PCR product was cloned into TOPO TA vector from Invitrogen. The first 19 amino acids were truncated by PCR, and the resulting truncated nef was restricted with BamHI and XhoI, and purified by gel extraction. Vector pBNX65, which contains an ATI promoter, was restricted with BamHI and XhoI, gel extracted and dephosphorylated, and ligated with the truncated nef. Positive clones were selected by HindIII digestion. The resulting plasmid pBN29, and the recombination vector pBNX59 (IGR I4L-I5L) were restricted with PacI; the insert was gel purified, while the vector was dephosphorylated before ligation. Positive clones of the resulting plasmid pBN31 were selected by SalI and ScaI digestion. The ATI-truncated nef gene clone #11 was used for homologous recombination.

Generation of a Recombinant MVA (mBN67A) Comprising a Truncated nef Gene Under the Control of the ATI Promoter Primary CEF cells were prepared in serum-free medium containing 4 mM L-Glutamine and seeded in six-well plates. Cells were incubated for 24-48 h until about 60 to 80% confluence. Cells were infected with MVA-BN at a MOI of 1.0. At about 60 min after infection, cells were transfected with 0.5 µg of plasmid DNA (pBN131) per well using Effectene (Qiagen). The transfected cells were harvested after 2 days. The virus was released by three cycles of freeze thawing. Tenfold dilutions of the virus-containing supernatant were used to infect freshly prepared CEF cells at 90% confluence in VP-SFM serum-free medium containing L-Glutamine, and Xanthine, Hypoxanthine, and Mycophenolic acid (Sigma) were added. The cells were incubated for another 48 h.

To select recombinant single clones, cells were seeded in 96-well plates and tenfold dilutions of the virus-containing supernatant were used to infect the cells. Plaque purification was performed after 48 h. Single virus-plaques detected in the highest dilution were selected, and harvested in VP-SFM. Virus-plaques were stored at −20° C., or directly used for infection of new CEF cells.

After 4 rounds of plaque purification, the insertion of the foreign DNA (truncated nef) and absence of wild-type virus was confirmed by PCR. The resulting recombinant virus clone was named mBN67A. After 2 plaque-purifications under non selective conditions the recombinant virus MVA-mBN67B, mostly devoid of the selection cassette, was isolated.

Cloning of the Recombination Plasmid pBN108 Comprising a gag-pol Fusion Gene and a Transdominant Tat, Each Under the Control of the ATI Promoter The gag-pol fusion protein was generated by PCR including restriction sites. The PCR product was restricted with BamHI and XhoI. This fragment was ligated to the BamHI and XhoI-restricted and dephosphorylated vector pBNX65 (containing ATI promoter), resulting in pBN73. Positive pBN73 clones were screened by XbaI restriction. To create a necessary frameshift between gag and pol one nucleotide (T) was inserted, resulting in pBN97.

Positive pBN97 clones were screened by specific PCR for the fusion site. To insert transdominant tat into pBN97, tat was generated by oligoannealing and PCR including appropriate restriction sites, and was inserted after restriction with Acc65I into pBNX65 (containing ATI promoter), also restricted with Acc65I and dephosphorylated. To identify positive clones of the resulting vector, preparations of DNA were screened with HindIII. Further, to obtain transdominant tat, 2 amino acid exchanges, at positions 22 (Cys>Gly) and 37 (Cys>Ser), were done, and the resulting vector pBN59 was obtained.

Next, transdominant tat was amplified out of pBN59 by PCR including restriction sites and ATI promoter. The PCR product was restricted with XbaI, and ligated to XbaI-restricted and dephosphorylated pBN97, resulting in pBN98. Positive right orientated clones were identified by digest with Acc65I. ATI-td tat and ATI-gag-pol were restricted with PacI, gel extracted, and then ligated with PacI-linearized and dephosphorylated recombination vector pBNX67 (IGR 136-137), resulting in pBN108. Positive clones were selected by PacI restriction, and for proper orientation they were also checked by sequencing. The ATI-td tat and ATI-gag-pol positive clone #8 was used for homologous recombination.

Generation of a Recombinant MVA (mBN78A) Comprising a Truncated nef Gene, a gag-pol Fusion Gene and a Transdominant Tat Gene, Each Under the Control of the ATI Promoter Primary CEF cells were prepared in serum-free medium containing 4 mM L-Glutamine and seeded in six-well plates. Cells were incubated for 24-48. h until about 60 to 80% confluence. Cells were infected with MVA-mBN67B at a MOI of about 1.0. About 60 min after infection, cells were transfected with 0.5 µg plasmid DNA (pBN108) per well using Effectene (Qiagen). The transfected cells were harvested after 2 days. Virus was released by three cycles of freeze thawing. Tenfold dilutions of the virus-containing supernatant were used to infect freshly prepared CEF cells at 90% confluence, VP-SFM serum-free medium containing L-Glutamine and G418 (Gibco/Invitrogen) was added, and the cells were incubated for another 48 h.

To select recombinant single clones, cells were seeded in 96-well plates and tenfold dilutions of the virus containing supernatant were used to infect the cells. Plaque purification was performed after 48 h. Single virus-plaques detected in the highest dilution plates were selected, and harvested in VP-SFM. Virus-plaques were stored at −20° C., or directly used for infection of new CEF cells.

After 5 rounds of plaque purification, the insertion of the foreign DNA and absence of wild-type virus was confirmed by PCR. The resulting recombinant virus clone was named mBN78A. After 4 plaque-purifications under non selective conditions the recombinant virus MVA-mBN78 B, mostly devoid of the selection cassette, was isolated.

Cloning of the Recombination Plasmid pBN175 Comprising a Vif-Vpr-Vpu-Rev Fusion Gene Under the Control of the ATI Promoter The accessory genes vif, vpr, vpu and rev were generated as a fusion protein by oligoannealing followed by PCR, and included restriction sites within the primers. After restriction of the PCR products with BamHI and XhoI, the genes were inserted into the BamHI/XhoI-restricted, purified and dephosphorylated pBNX65 vector (containing ATI promoter), resulting in pBN32. Clones were analysed by BamHI restriction and sequencing. Five mutations noticed in the vif-vpr-vpu-rev sequence were corrected by in vitro mutagenesis. The corrected pBN32 was then restricted with KpnI, blunted with T4-polymerase, and then cut with NotI. The recombination vector pBNX86 (IGR 07/08) was restricted with PacI, blunted and restricted with NotI, and then ligated with ATI-vif-vpr-vpu-rev. Positive clones of the resulting plasmid pBN175 were selected by restriction analysis with SphI.

Generation of a Recombinant MVA (mBN87B) Comprising a Truncated nef Gene, a gag-pol Fusion Gne, a Transdominant Tat Gene, and a Vif-Vpr-Vpu-Rev Fusion Gene, Each Under the Control of the ATI Promoter Primary CEF cells were prepared in serum-free medium containing 4 mM L-Glutamine and seeded in six-well plates. Cells were incubated for 24-48 h until about 60 to 80% confluence. The cells were infected with MVA-mBN78B at a MOI of about 1.0. At 60 min after infection cells were transfected with 0.5 µg of plasmid DNA (pBN175) per well using Effectene (Qiagen). The transfected cells were harvested after 2 days. Virus was released by three cycles of freeze thawing. Tenfold dilutions of the virus-containing supernatant were used to infect freshly prepared CEF cells at about 90% confluence. VP-SFM serum-free medium containing L-Glutamine and G418 (Gibco BRL) was added, and the cells were incubated for another 48 h.

To select recombinant single clones, cells were seeded in 96-well plates and tenfold dilutions of the virus-containing supernatant were used to infect the cells. Plaque purification was performed after 48 h. Single virus-plaques detected in the highest dilution plates were selected, and harvested in VP-SFM. Virus-plaques were stored at −20° C., or directly used for infection of new CEF cells.

After 5 rounds of plaque purification, the insertion of the foreign DNA (truncated nef gene, a gag-pol fusion gene, a transdominant Tat gene, and a Vif-Vpr-Vpu-Rev fusion gene) and absence of wild-type virus was confirmed by PCR. The resulting recombinant virus clone was named mBN87A. After 5 plaque-purifications under non selective conditions the recombinant virus MVA-mBN87 B devoid of the selection cassette could be isolated. The identity of the recombinant vector was confirmed by standard methods.

We claim:

1. A recombinant Modified Vaccinia Ankara Virus (MVA) comprising one or more human immunodeficiency virus DNA coding sequences inserted into an intergenic region (IGR) of the viral genome, wherein the IGR is selected from the group consisting of IGRs:

001L-002L, 002L-003L, 005R-006R, 006L-007R, 007R-008L, 008L-009L, 017L-018L, 018L-019L, 019L-020L, 020L-021L, 023L-024L, 024L-025L, 025L-026L, 028R-029L, 030L-031L, 031L-032L, 032L-033L, 035L-036L, 036L-037L, 037L-038L, 039L-040L, 043L-044L, 044L-045L, 046L-047R, 049L-050L, 050L-051L, 051L-052R, 052R-053R, 053R-054R, 054R-055R, 055R-056L, 061L-062L, 064L-065L, 065L-066L, 066L-067L, 077L-078R, 078R-079R, 080R-081R, 081R-082L, 082L-083R, 085R-086R, 086R-087R, 088R-089L, 089L-090R, 092R-093L, 094L-095R, 096R-097R, 097R-098R, 101R-102R, 103R-104R, 105L-106R, 107R-108L, 108L-109L, 109L-110L, 110L-111L, 113L-114L, 114L-115L, 115L-116R, 117L-118L, 118L-119R, 122R-123L, 123L-124L, 124L-125L, 125L-126L, 133R-134R, 134R-135R, 137L-138L, 141L-142R, 143L-144R, 144R-145R, 145R-146R, 146R-147R, 147R-148R, 148R-149L, 152R-153L, 153L-154R, 154R-155R, 156R-157R, 157L-158R, 159R-160L, 160L-161R, 162R-163R, 163R-164R, 164R-165R, 165R-166R, 166R-167R, 167R-168R, 170R-171R, 173R-174R, 175R-176R, 176R-177R, 178R-179R, 179R-180R, 180R-181R, 183R-184R, 184R-185L, 185L-186R, 186R-187R, 187R-188R, 188R-189R, 189R-190R, and 192R-193R.

2. The recombinant MVA of claim 1, wherein the IGR is 007R-008L.

3. The recombinant MVA of claim 1, wherein the IGR is 018L-019L.

4. The recombinant MVA of claim 1, wherein the IGR is 044L-045L.

5. The recombinant MVA of claim 1, wherein the IGR is 064L-065L.

6. The recombinant MVA of claim 1, wherein the IGR is 148R-149L.

7. The recombinant MVA of claim 1, wherein the MVA comprises multiple human immunodeficiency virus DNA coding sequences inserted into multiple intergenic regions (IGR) of the viral genome.

8. The recombinant MVA of claim 1, wherein the coding sequences are placed under the transcriptional control of one or more poxviral transcription control elements.

9. The recombinant MVA virus of claim 1, wherein one or more of the human immunodeficiency virus DNA coding sequences is an HIV Env sequence.

10. The recombinant MVA virus of claim 8, wherein the poxviral transcription control element is the ATI promoter.

11. The recombinant MVA virus of claim 8, wherein the poxviral transcription control element is the p7.5 promoter.

12. An isolated host cell comprising the recombinant MVA of claim 1, wherein the host cell is a prokaryotic cell.

13. An isolated host cell comprising the recombinant MVA of claim 1, wherein the host cell is a eukaryotic cell.

14. The host cell of claim 13, wherein said cell is a human cell.

15. The host cell of claim 13, wherein said cell is a nonhuman mammalian cell.

16. The host cell of claim 13, wherein said cell is an insect cell.

17. The host cell of claim 13, wherein said cell is a fish cell.

18. The host cell of claim 13, wherein said cell is a plant cell.

19. The host cell of claim 13, wherein said cell is a fungal cell.

\* \* \* \* \*

SEQUENCE LISTING

```
<160> NUMBER OF SEQ ID NOS: 37

<210> SEQ ID NO 1
<211> LENGTH: 20
<212> TYPE: DNA
<213> ORGANISM: Artificial
<220> FEATURE:
<223> OTHER INFORMATION: primer

<400> SEQUENCE: 1
caactctctt cttgattacc                                              20

<210> SEQ ID NO 2
<211> LENGTH: 19
<212> TYPE: DNA
<213> ORGANISM: artificial
<220> FEATURE:
<223> OTHER INFORMATION: primer

<400> SEQUENCE: 2
cgatcaaagt caatctatg                                               19

<210> SEQ ID NO 3
<211> LENGTH: 33
<212> TYPE: DNA
<213> ORGANISM: artificial
<220> FEATURE:
<223> OTHER INFORMATION: primer

<400> SEQUENCE: 3
tccccgcgga gaggcgtaaa agttaaatta gat                               33

<210> SEQ ID NO 4
<211> LENGTH: 33
<212> TYPE: DNA
<213> ORGANISM: artificial
<220> FEATURE:
<223> OTHER INFORMATION: primer

<400> SEQUENCE: 4
tgatctagaa tcgctcgtaa aaactgcgga ggt                               33
```

```
<210> SEQ ID NO 5
<211> LENGTH: 29
<212> TYPE: DNA
<213> ORGANISM: artificial
<220> FEATURE:
<223> OTHER INFORMATION: primer

<400> SEQUENCE: 5
ccgctcgagt tcacgttcag ccttcatgc                                29

<210> SEQ ID NO 6
<211> LENGTH: 32
<212> TYPE: DNA
<213> ORGANISM: artificial
<220> FEATURE:
<223> OTHER INFORMATION: primer

<400> SEQUENCE: 6
cgggggccct attttgtata atatctggta ag                            32

<210> SEQ ID NO 7
<211> LENGTH: 35
<212> TYPE: DNA
<213> ORGANISM: artificial
<220> FEATURE:
<223> OTHER INFORMATION: primer

<400> SEQUENCE: 7
cggctgcagg gtaccttcac gttcagcctt catgc                         35

<210> SEQ ID NO 8
<211> LENGTH: 34
<212> TYPE: DNA
<213> ORGANISM: artificial
<220> FEATURE:
<223> OTHER INFORMATION: primer

<400> SEQUENCE: 8
cggaagcttt atatggttta ggatattctg tttt                          34

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
cgttcgcatg ggttacctcc                                          20

<210> SEQ ID NO 10
<211> LENGTH: 18
<212> TYPE: DNA
<213> ORGANISM: artificial
<220> FEATURE:
<223> OTHER INFORMATION: primer

<400> SEQUENCE: 10
gacgcatgaa ggctgaac                                            18

<210> SEQ ID NO 11
<211> LENGTH: 27
<212> TYPE: DNA
<213> ORGANISM: artificial
<220> FEATURE:
```

```
<223> OTHER INFORMATION: primer

<400> SEQUENCE: 11
cgcgagctca ataaaaaaaa gttttac                                    27

<210> SEQ ID NO 12
<211> LENGTH: 29
<212> TYPE: DNA
<213> ORGANISM: artificial
<220> FEATURE:
<223> OTHER INFORMATION: primer

<400> SEQUENCE: 12
aggccgcgga tgcatgttat gcaaaatat                                  29

<210> SEQ ID NO 13
<211> LENGTH: 36
<212> TYPE: DNA
<213> ORGANISM: artificial
<220> FEATURE:
<223> OTHER INFORMATION: primer

<400> SEQUENCE: 13
ccgctcgagc gcggatccca atatatggca tagaac                          36

<210> SEQ ID NO 14
<211> LENGTH: 24
<212> TYPE: DNA
<213> ORGANISM: artificial
<220> FEATURE:
<223> OTHER INFORMATION: primer

<400> SEQUENCE: 14
cagggccctc tcatcgcttt catg                                       24

<210> SEQ ID NO 15
<211> LENGTH: 28
<212> TYPE: DNA
<213> ORGANISM: artificial
<220> FEATURE:
<223> OTHER INFORMATION: primer

<400> SEQUENCE: 15
tttctgcagt gatatttatc caatacta                                   28

<210> SEQ ID NO 16
<211> LENGTH: 21
<212> TYPE: DNA
<213> ORGANISM: artificial
<220> FEATURE:
<223> OTHER INFORMATION: primer

<400> SEQUENCE: 16
ctggataaat acgaggacgt g                                          21

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
gacaattatc cgacgcaccg                                            20
```

<210> SEQ ID NO 18
<211> LENGTH: 29
<212> TYPE: DNA
<213> ORGANISM: artificial
<220> FEATURE:
<223> OTHER INFORMATION: primer

<400> SEQUENCE: 18
cgcgagctca tttcttagct agagtgata                               29

<210> SEQ ID NO 19
<211> LENGTH: 27
<212> TYPE: DNA
<213> ORGANISM: artificial
<220> FEATURE:
<223> OTHER INFORMATION: primer

<400> SEQUENCE: 19
aggccgcgga gtgaaagcta gagaggg                                 27

<210> SEQ ID NO 20
<211> LENGTH: 36
<212> TYPE: DNA
<213> ORGANISM: artificial
<220> FEATURE:
<223> OTHER INFORMATION: primer

<400> SEQUENCE: 20
ccgctcgagc gcggatccta aactgtatcg attatt                       36

<210> SEQ ID NO 21
<211> LENGTH: 26
<212> TYPE: DNA
<213> ORGANISM: artificial
<220> FEATURE:
<223> OTHER INFORMATION: primer

<400> SEQUENCE: 21
cagggcccct aaatgcgctt ctcaat                                  26

<210> SEQ ID NO 22
<211> LENGTH: 31
<212> TYPE: DNA
<213> ORGANISM: artificial
<220> FEATURE:
<223> OTHER INFORMATION: primer

<400> SEQUENCE: 22
tttctgcagc cttcctgggt ttgtattaac g                            31

<210> SEQ ID NO 23
<211> LENGTH: 24
<212> TYPE: DNA
<213> ORGANISM: artificial
<220> FEATURE:
<223> OTHER INFORMATION: primer

<400> SEQUENCE: 23
cgttagacaa cacaccgacg atgg                                    24

<210> SEQ ID NO 24
<211> LENGTH: 21
<212> TYPE: DNA
<213> ORGANISM: artificial
<220> FEATURE:
<223> OTHER INFORMATION: primer

```
<400> SEQUENCE: 24
cggatgaaaa atttttggaa g                                          21

<210> SEQ ID NO 25
<211> LENGTH: 29
<212> TYPE: DNA
<213> ORGANISM: artificial
<220> FEATURE:
<223> OTHER INFORMATION: primer

<400> SEQUENCE: 25
tccccgcggg gactcataga ttatcgacg                                  29

<210> SEQ ID NO 26
<211> LENGTH: 35
<212> TYPE: DNA
<213> ORGANISM: artificial
<220> FEATURE:
<223> OTHER INFORMATION: primer

<400> SEQUENCE: 26
ctagtctaga ctagtctatt aatccacaga aatac                           35

<210> SEQ ID NO 27
<211> LENGTH: 39
<212> TYPE: DNA
<213> ORGANISM: artificial
<220> FEATURE:
<223> OTHER INFORMATION: primer

<400> SEQUENCE: 27
cccaagcttg ggcgggatcc cgtttctagt atggggatc                       39

<210> SEQ ID NO 28
<211> LENGTH: 26
<212> TYPE: DNA
<213> ORGANISM: artificial
<220> FEATURE:
<223> OTHER INFORMATION: primer

<400> SEQUENCE: 28
tagggcccgt tattgccatg atagag                                     26

<210> SEQ ID NO 29
<211> LENGTH: 26
<212> TYPE: DNA
<213> ORGANISM: artificial
<220> FEATURE:
<223> OTHER INFORMATION: primer

<400> SEQUENCE: 29
tttctgcagt gtataatacc acgagc                                     26

<210> SEQ ID NO 30
<211> LENGTH: 22
<212> TYPE: DNA
<213> ORGANISM: artificial
<220> FEATURE:
<223> OTHER INFORMATION: primer

<400> SEQUENCE: 30
ctgtataggt atgtcctctg cc                                         22

<210> SEQ ID NO 31
<211> LENGTH: 18
```

```
<212> TYPE: DNA
<213> ORGANISM: artificial
<220> FEATURE:
<223> OTHER INFORMATION: primer

<400> SEQUENCE: 31
gctagtagac gtggaaga                                                   18

<210> SEQ ID NO 32
<211> LENGTH: 1192
<212> TYPE: DNA
<213> ORGANISM: vaccinia virus
<220> FEATURE:
<221> NAME/KEY: Fragment of ORF C 64L
<222> LOCATION: (1)..(526)
<220> FEATURE:
<221> NAME/KEY: IGR 64-65
<222> LOCATION: (527)..(608)
<220> FEATURE:
<221> NAME/KEY: Fragment of ORF C 65L
<222> LOCATION: (609)..(1190)

<400> SEQUENCE: 32
caccttctat agatctgaga atggatgatt ctccagtcga acatattct accatggatc      60
cgtttaattt gttgatgaag atggattcat ccttaaatgt tttctctgta atagtttcca    120
ccgaaagact atgcaaagaa tttggaatgc gttccttgtg cttaatgttt ccatagacgg    180
cttctagaag ttgatacaac ataggactag ccgcggtaac tttatttttt agaaagtatc    240
catcgcttct atcttgttta gatttatttt tataaagttt agtctctcct tccaacataa    300
taaaagtgga agtcatttga ctagataaac tatcagtaag ttttatagag atagacgaac    360
aattagcgta ttgagaagca tttagtgtaa cgtattcgat acattttgca ttagatttac    420
taatcgattt tgcatactct ataacacccg cacaagtctg tagagaatcg ctagatgcag    480
taggtcttgg tgaagtttca actctcttct tgattacctt actcatgatt aaacctaaat    540
aattgtactt tgtaatataa tgatatatat tttcactttta tctcatttga gaataaaaat    600
gttttttgttt aaccactgca tgatgtacag atttcggaat cgcaaaccac cagtggtttt    660
attttatcct tgtccaatgt gaattgaatg ggagcggatg cgggtttcgt acgtagatag    720
tacattcccg ttttagacc gagactccat ccgtaaaaat gcatactcgt tagtttggaa     780
taactcggat ctgctatatg gatattcata gattgacttt gatcgatgaa ggctcccctg    840
tctgcagcca ttttatgat cgtctttgt ggaatttccc aaatagtttt ataaactcgc      900
ttaatatctt ctggaaggtt tgtattctga atggatccac catctgccat aatcctattc    960
ttgatctcat cattccataa ttttctctcg gttaaaactc taaggagatg cggattaact   1020
acttgaaatt ctccagacaa tactctccga gtgtaaatat tactggtata cggttccacc   1080
gactcattat ttcccaaaat ttgagcagtt gatgcagtcg gcataggtgc caccaataaa   1140
ctatttctaa gaccgtatgt tctgatttta tctttttagag gttcccaatt cc           1192

<210> SEQ ID NO 33
<211> LENGTH: 1200
<212> TYPE: DNA
<213> ORGANISM: vaccinia virus
<220> FEATURE:
<221> NAME/KEY: Fragment of ORF 135R
<222> LOCATION: (1)..(96)
<220> FEATURE:
<221> NAME/KEY: ORF C 136L
<222> LOCATION: (101)..(298)
<220> FEATURE:
<221> NAME/KEY: IGR 136-137
```

<220> FEATURE:
<221> NAME/KEY: Fragment of ORF C 137L
<222> LOCATION: (884)..(1198)

<400> SEQUENCE: 33

```
agaggcgtaa aagttaaatt agatttcgaa cgaaggcctc cttcgtttta taaaccatta    60
gataaagttg atctcaaacc gtcttttctg gtgtaatatt ctagtttggt agtagataca   120
tatcaatatc atcaaattcg agatccgaat tataaaatgg gcgtggattg ttaactatag   180
aatcggacgt ctgatattcg aaaatctgtg gagttttagg ttttggtgga ggtgtaactg   240
ctacttggga tactgaagtc tgatattcag aaagctgggg gatgttctgg ttcgacatcc   300
accgatggtg tcacatcact aatcggttcg gtaacgtctg tggacgatgg aggcaccact   360
tctacaggtt ctggttcttt atcctcagtc atcaacggag ctacttcaat gcgaggaaat   420
gtataatttg gtaatggttt ctcatgtgga tctgaagaag aggtaagata tctactagaa   480
agataccgat cacgttctag ttctcttttg tagaacttaa cttttctttt ctccgcatct   540
agttgatatt ccaacctctt cacgttcgca tgggttacct ccgcagtttt tacgagcgat   600
ttcacgttca gccttcatgc gtcttatagc atgaattcgc ttatcgttat cgggtttagc   660
ttctgtcacc ttagcaattc ctttttttatt aaactctaca taatcatatc catttctatt   720
gtttgttcta atataaacga gtatagcatc attgctaaat ttttcaatag tatcgaaaac   780
agaatatcct aaaccatata atatatattc aggaacactc aaactaaatg tccaggattc   840
tcctaaatac gtaaacttta atagtgcgaa atcattcaaa aatctaccac ttatagatag   900
atagatagta cataaatgcg tatagtagtc tacctatctc tttattatga aaaccggcat   960
tacgatcata tatgtcgtga atacctgtg atccgtttac gttaaccat aaatacatgg   1020
gtgatcctat aaacatgaat ttatttctaa ttctcagagc tatagttaat tgaccgtgta  1080
atatttgctt acatgcatac ttgatacgat cattaataag atttttatca ttgctcgtta  1140
tttcagaatc gtatatataa ggagtaccat cgtgattctt accagatatt atacaaaata  1200
```

<210> SEQ ID NO 34
<211> LENGTH: 1200
<212> TYPE: DNA
<213> ORGANISM: vaccinia virus
<220> FEATURE:
<221> NAME/KEY: Fragment of ORF 07R
<222> LOCATION: (1)..(338)
<220> FEATURE:
<221> NAME/KEY: IGR 07-08
<222> LOCATION: (339)..(852)
<220> FEATURE:
<221> NAME/KEY: Fragment of ORF C 08L
<222> LOCATION: (853)..(1200)

<400> SEQUENCE: 34

```
aataaaaaaa agttttacta atttaaaatt atttacattt ttttcactgt ttagtcgcgg    60
atatggaatt cgatcctgcc aaaatcaata catcatctat agatcatgta acaatattac   120
aatacataga tgaaccaaat gatataagac taacagtatg cattatcaca aaaataaatc   180
cacatttggc taatcaattt cgggcttgga aaaacgtat cgccggaagg gactatatga   240
ctaacttatc tagagataca ggaatacaac aatcaaaact tactgaaact gtcaaaaaaa   300
tagaaacata tatggtctat atatacacta caatttagtt attaattgga taaccgatgt   360
gattatcaat caatattaag aaggttggta aattggtaca tagctaataa tacctataca   420
cccaataata caacaaccat ttctgagttg gatatcatca aaatactgga taaatacgag   480
```

```
gacgtgtata gagtaagtaa agaaaaagaa tgtgaaattt gctatgaagt tgtttactca      540
aaacgataga tactttggtt tattggattc gtgtaatcat atattttgca taacatgcat      600
caatatatgg catagaacac gaagagaaac cggtgcgtcg gataattgtc ctatatgtcg      660
tacccgtttt agaaacataa caatgagcaa gttaactaat aaataaaaag tttaatttgt      720
tgacgacgta tgtcgttatt ttttctcgta taaaagatta atttgattct aatataatct      780
ttagtattgg ataaatatca attcaaatta attccattag attatatcat aaataaaaat      840
agtagcacgc actacttcag ccaaatattc tttttgaaa cgccatctat cgtagtgagg       900
acacaagtga acctataatg agcaaattta ttagtatcgg ttacatgaag gactttacgt      960
agagtggtga ttccactatc tgtggtacga acggtttcat cttctttgat gccatcaccc     1020
agatgttcta taaacttggt atcctttgcc aaccaataca tatagctaaa ctcaggcata     1080
tgttccacac atcctgaaca atgaaattct ccagaagatg ttacaatgtc tagatttgga     1140
catttggttt caaccgcgtt aacatatgag tgaacacacc catacatgaa agcgatgaga     1200

<210> SEQ ID NO 35
<211> LENGTH: 1200
<212> TYPE: DNA
<213> ORGANISM: vaccinia virus
<220> FEATURE:
<221> NAME/KEY: Fragment of ORF C 44L
<222> LOCATION: (1)..(375)
<220> FEATURE:
<221> NAME/KEY: IGR 44-45
<222> LOCATION: (376)..(647)
<220> FEATURE:
<221> NAME/KEY: Fragment of ORF C 45L
<222> LOCATION: (648)..(1200)

<400> SEQUENCE: 35
atttcttagc tagagtgata atttcgttaa acattcaaa tgttgttaaa tgatcggatc        60
taaaatccat attttctggt agtgtttcta ccagcctaca ttttgctccc gcaggtaccg      120
gtgcaaatgg ccacatttag ttaacataaa aacttataca tcctgttcta tcaacgattc      180
tagaatatca tcggctatat cgctaaaatt ttcatcaaag tcgacatcac aacctaactc      240
agtcaatata ttaagaagtt ccatgatgtc atcttcgtct atttctatat ccgtatccat      300
tgtagattgt tgaccgatta tcgagtttaa atcattacta atactcaatc cttcagaata      360
caatctgtgt tcattgtaa atttataggc ggtgtattta agttggtaga ttttcaatta      420
tgtatcaata tagcaacagt agttcttgct cctccttgat tctagcatcc tcttcattat     480
tttcttctac gtacataaac atgtccaata cgttagacaa cacaccgacg atggcggccg      540
ccacagacac gaatatgact aaaccgatga ccatttaaaa accctctct agctttcact      600 taaactgtat cgattattct tttagaacat gtataatata aaaacattat tctatttcga     660
atttaggctt ccaaaaattt ttcatccgta aaccgataat aatatatata gacttgttaa      720
tagtcggaat aaatagatta atgcttaaac tatcatcatc tccacgatta gagatacaat      780
atttacattt tttttgctgt ttcgaaactt tatcaataca cgttaataca aacccaggaa      840
ggagatattg aaactgaggc tgttgaaaat gaaacggtga atacaataat tcagataatg      900
taaaatcatg attccgtatt ctgatgatat tagaactgct aatggatgtc gatggtatgt      960
atctaggagt atctattta acaaagcatc gatttgctaa tatacaatta tcattttgat      1020
taattgttat tttattcata ttcttaaaag gtttcatatt tatcaattct tctacattaa     1080
aaatttccat ttttaattta tgtagccccg caatactcct cattacgttt cattttttgt     1140
```

```
ctataatatc cattttgttc atctcggtac atagattatc caattgagaa gcgcatttag    1200
```

<210> SEQ ID NO 36
<211> LENGTH: 1200
<212> TYPE: DNA
<213> ORGANISM: vaccinia virus
<220> FEATURE:
<221> NAME/KEY: Fragment of ORF 148R
<222> LOCATION: (1)..(596)
<220> FEATURE:
<221> NAME/KEY: IGR 148-149
<222> LOCATION: (597)..(855)
<220> FEATURE:
<221> NAME/KEY: Fragment of ORF C 149L
<222> LOCATION: (856)..(1200)

<400> SEQUENCE: 36

```
ctcatagatt atcgacgatt atactctgta ttagttctgt cggaggatgt gttatctcta     60
tagataatga cgtcaatggc aaaaatattc taacctttcc cattgatcat gctgtaatca    120
tatccccact gagtaaatgt gtcgtagtta gcaagggtcc tacaaccata ttggttgtta    180
aagcggatat acctagcaaa cgattggtaa catcgtttac aaacgacata ctgtatgtaa    240
acaatctatc actgattaat tattcgccgt tgtctgtatt cattattaga cgagttaccg    300
actatttgga tagacacata tgcgatcaga tatttgcgaa taataagtgg tattccatta    360
taaccatcga caataagcag tttcctattc catcaaactg tataggtatg tcctctgcca    420
agtacataaa ttctagcatc gagcaagata ctttaataca tgtttgtaac ctcgagcatc    480
cattcgactt agtatacaaa aaaatgcagt cgtacaattc tgtacctatc aaggaacaaa    540
tattgtacgg tagaattgat aatataaata tgagcattag tatttctgtg gattaataga    600
tttctagtat ggggatcatt aatcatctct aatctctaaa tacctcataa aacgaaaaaa    660
aagctattat caaatactgt acggaatgga ttcattctct tctcttttta tgaaactctg    720
ttgtatatct actgataaaa ctggaagcaa aaaatctgat aaaaagaata agaataagat    780
caaggattat tataaaataa caatagttcc tggttcctct tccacgtcta ctagctcgtg    840
gtattataca catgcctagt aatagtctct ttgcgttgac ggaaagcaga ctagaaataa    900
caggctaaaa tgttcagaca ccataatagt tcccaaccca gataataaca gagtaccatc    960
aacacattcc tttaaactca atcccaaacc caaaaccgtt aaaatgtatc cggccaattg   1020
atagtagata atgaggtgta cagcgcatga tgatttacac agtaaccaaa atgaaaatac   1080
tttagtaatt ataagaaata tagatggtaa cgtcatcatc aacaatccaa taatatgccg   1140
gagagtaaac attgacggat aaaacaaaaa tgctccgcat aactctatca tggcaataac   1200
```

<210> SEQ ID NO 37
<211> LENGTH: 1200
<212> TYPE: DNA
<213> ORGANISM: vaccinia virus
<220> FEATURE:
<221> NAME/KEY: Fragment of ORF 018L
<222> LOCATION: (1)..(399)
<220> FEATURE:
<221> NAME/KEY: IGR 018L-019L
<222> LOCATION: (400)..(607)
<220> FEATURE:
<221> NAME/KEY: Fragment of ORF C 019L
<222> LOCATION: (608)..(1081)
<220> FEATURE:
<221> NAME/KEY: non-coding region
<222> LOCATION: (1082)..(1200)

<400> SEQUENCE: 37

```
ggatgagtag ttttcttctt taactttata cttttttacta atcatattta gactgatgta        60
tgggtaatag tgtttaaaga gttcgttctc atcatcagaa taaatcaata tctctgtttt       120
tttgttatac agatgtatta cagcctcata tattacgtaa tagaacgtgt catctacctt       180
attaactttc accgcatagt tgtttgcaaa tacggttaat cctttgacct cgtcgatttc       240
cgaccaatct gggcgtataa tgaatctaaa ctttaatttc ttgtaatcat tcgaaataat       300
ttttagtttg catccgtagt tatcccctttt atgtaactgt aaatttctca acgcgatatc       360
tccattaata atgatgtcga attcgtgctg tatacccata ctgaatggat gaacgaatac       420
cgacggcgtt aatagtaatt tacttttttca tctttacata ttgggtacta gttttactat       480
cataagttta taaattccac aagctactat ggaataagcc aaccatctta gtataacaca       540
catgtcttaa agtttattaa ttaattacat gttgttttat atatcgctac gaatttaaac       600
agagaaatca gtttaggaaa aaaaaatatc tatctacatc atcacgtctc tgtattctac       660
gatagagtgc tactttaaga tgagacatat ccgtgtcatc aaaaatatac tccattaaaa       720
tgattattcc ggcagcgaac ttgatattgg atatatcaca acctttgtta atatctacga       780
caatagacag cagtcccatg gttccataaa cagtgagttt atctttcttt gaagagatat       840
tttgtagaga tcttataaaa ctgtcgaatg acatcgcatt tatatcttta gctaaatcgt       900
atatgttacc atcgtaatat ctaaccgcgt ctatcttaaa cgtttccatc gctttaaaga       960
cgtttccgat agatggtctc atttcatcag tcatactgag ccaacaaata taatcgtgta      1020
taacatcttt gatagaatca gactctaaag aaaacgaatc ggctttatta tacgcattca      1080
tgataaactt aatgaaaaat gtttttcgtt gtttaagttg gatgaatagt atgtcttaat      1140
aattgttatt atttcattaa ttaatattta gtaacgagta cactctataa aaacgagaat      1200
```